US009050120B2

(12) United States Patent
Swarup et al.

(10) Patent No.: US 9,050,120 B2
(45) Date of Patent: *Jun. 9, 2015

(54) APPARATUS AND METHOD OF USER INTERFACE WITH ALTERNATE TOOL MODE FOR ROBOTIC SURGICAL TOOLS

(75) Inventors: Nitish Swarup, Sunnyvale, CA (US); Scott Manzo, Shelton, CT (US)

(73) Assignee: INTUITIVE SURGICAL OPERATIONS, INC., Sunnyvale, CA (US)

(*) Notice: Subject to any disclaimer, the term of this patent is extended or adjusted under 35 U.S.C. 154(b) by 1366 days.

This patent is subject to a terminal disclaimer.

(21) Appl. No.: 12/028,750

(22) Filed: Feb. 8, 2008

(65) Prior Publication Data

US 2009/0088774 A1 Apr. 2, 2009

Related U.S. Application Data

(60) Provisional application No. 60/976,460, filed on Sep. 30, 2007.

(51) Int. Cl.
*A61B 19/00* (2006.01)
*A61B 18/14* (2006.01)
*A61B 17/00* (2006.01)

(52) U.S. Cl.
CPC ......... *A61B 19/2203* (2013.01); *A61B 18/1445* (2013.01); *A61B 19/5212* (2013.01); *A61B 19/56* (2013.01); *A61B 2019/2223* (2013.01); *A61B 2019/2234* (2013.01); *A61B 2019/2242* (2013.01); *A61B 2019/2246* (2013.01); *A61B 2017/00477* (2013.01)
USPC ............................ 606/130; 700/245; 700/260

(58) Field of Classification Search
CPC .................. A61B 19/2203; A61B 2019/2223; A61B 19/22; A61B 19/28
USPC ........................................ 700/245; 606/1, 130
See application file for complete search history.

(56) References Cited

U.S. PATENT DOCUMENTS

| 4,464,652 A | 8/1984 | Lapson et al. |
| 4,772,882 A | 9/1988 | Mical |
| 5,327,529 A | 7/1994 | Fults et al. |
| 5,562,655 A | 10/1996 | Mittelstadt et al. |
| 5,611,040 A | 3/1997 | Brewer et al. |
| 5,914,718 A | 6/1999 | Chiu et al. |

(Continued)

OTHER PUBLICATIONS

Rockall, Timothy A., "The da Vinci Telerobotic Surgical System," Chapter 8 in Primer of Robotic and Telerobotic Surgery, Eds. Garth H. Ballantyne et al., Pub. By Lippincott Williams and Wilkins, Philadelphia, 2004, pp. 57-60.

(Continued)

*Primary Examiner* — Redhwan K Mawari
*Assistant Examiner* — Rodney P King

(57) ABSTRACT

In one implementation, a method is disclosed in which a lock sensing mode is entered for a robotic surgical instrument. In the lock sensing mode, the degrees of freedom of movement in the robotic surgical instrument are switchably reduced. Further in the lock sensing mode, one or more end effectors of the robotic surgical instrument are switchably clamped together in the robotic surgical instrument. An increased level of torque may also be applied to the end effectors to increase a gripping force applied by the one or more end effectors in response to the reduced degrees of freedom of movement in the robotic surgical instrument.

21 Claims, 32 Drawing Sheets

(56) References Cited

U.S. PATENT DOCUMENTS

| | | | |
|---|---|---|---|
| 5,923,139 A * | 7/1999 | Colgate et al. | 318/566 |
| 6,184,868 B1 | 2/2001 | Shahoian et al. | |
| 6,459,926 B1 | 10/2002 | Nowlin et al. | |
| 6,493,608 B1 | 12/2002 | Niemeyer | |
| 6,714,839 B2 | 3/2004 | Salisbury, Jr. et al. | |
| 6,799,065 B1 | 9/2004 | Niemeyer | |
| 8,224,484 B2 | 7/2012 | Swarup et al. | |
| 2002/0032451 A1 * | 3/2002 | Tierney et al. | 606/130 |
| 2002/0032452 A1 | 3/2002 | Tierney et al. | |
| 2003/0195664 A1 * | 10/2003 | Nowlin et al. | 700/260 |
| 2004/0015079 A1 | 1/2004 | Berger et al. | |
| 2005/0043719 A1 * | 2/2005 | Sanchez et al. | 606/1 |
| 2005/0215866 A1 * | 9/2005 | Kim | 600/233 |
| 2005/0222587 A1 * | 10/2005 | Jinno et al. | 606/130 |
| 2006/0060630 A1 * | 3/2006 | Shelton et al. | 227/175.2 |
| 2008/0033240 A1 | 2/2008 | Hoffman et al. | |
| 2008/0046122 A1 * | 2/2008 | Manzo et al. | 700/245 |
| 2009/0088775 A1 | 4/2009 | Swarup et al. | |
| 2012/0179169 A1 | 7/2012 | Swarup et al. | |
| 2013/0006268 A1 | 1/2013 | Swarup et al. | |

OTHER PUBLICATIONS

U.S. Appl. No. 12/028,755, not published, Swarup; Nitish et al.

Taylor, Russell H. et al., "A Telerobotic Assistant for Laparoscopic Surgery," IEEE Engineering in Medicine and Biology, May/Jun. 1995, pp. 279-288, vol. 14, Issue 3, IEEE.

Vertut, Jean et al., *Robot Technology: Teleoperation and Robotics Evolution and Development*, 1986, vol. 3A, 332 pages, English translation Prentice-Hall, Inc., Inglewood Cliffs, NJ, USA.

U.S. Appl. No. 12/028,755 Final Office Action mailed Sep. 27, 2011, 12 pages.

U.S. Appl. No. 12/028,755 Office Action, mailed Mar. 29, 2011, 12 pages.

Office Action Jul. 11, 2012, U.S. Appl. No. 13/429,745 by Rodney P. King, 8 pages.

* cited by examiner

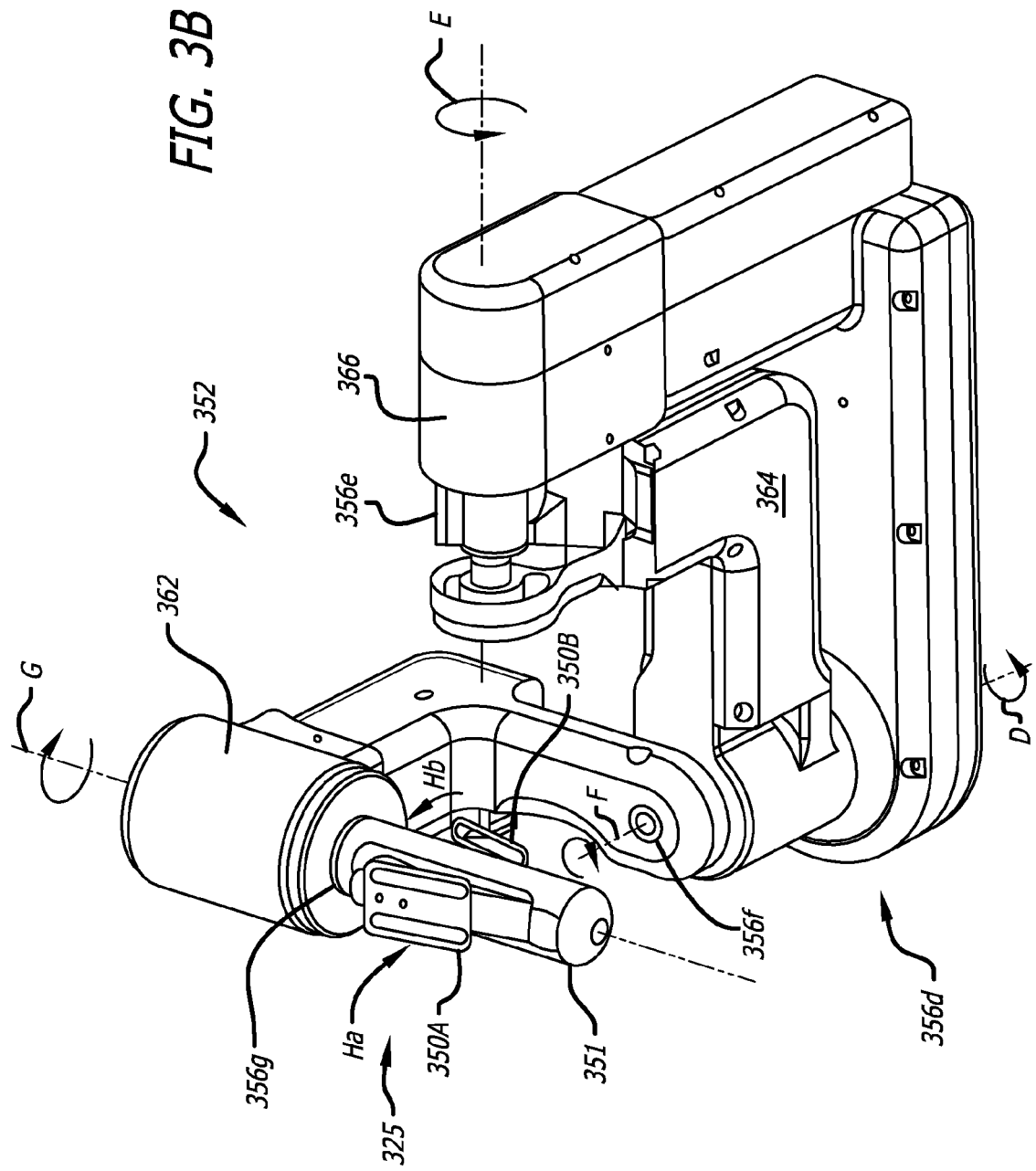

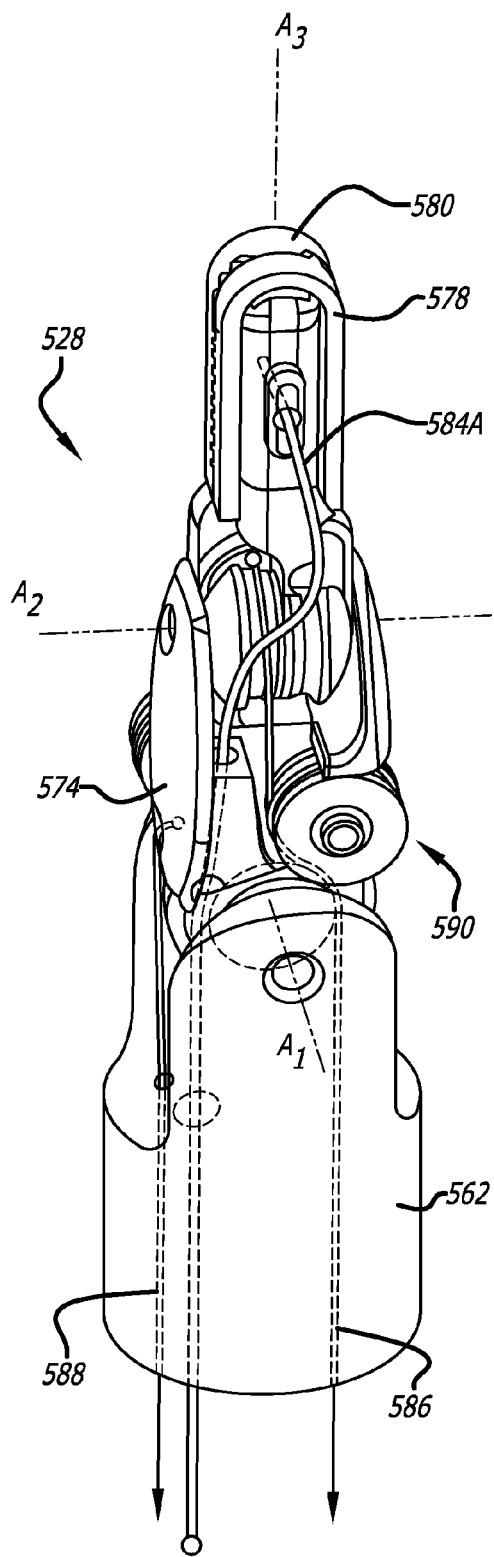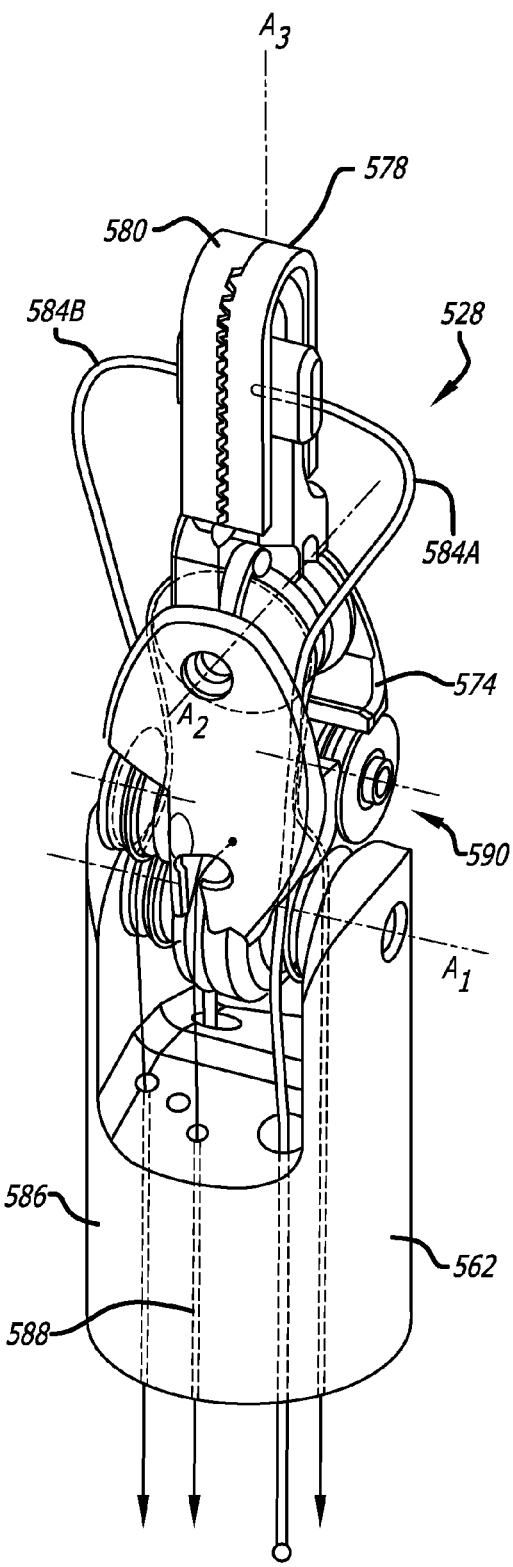
FIG. 5A
FIG. 5B

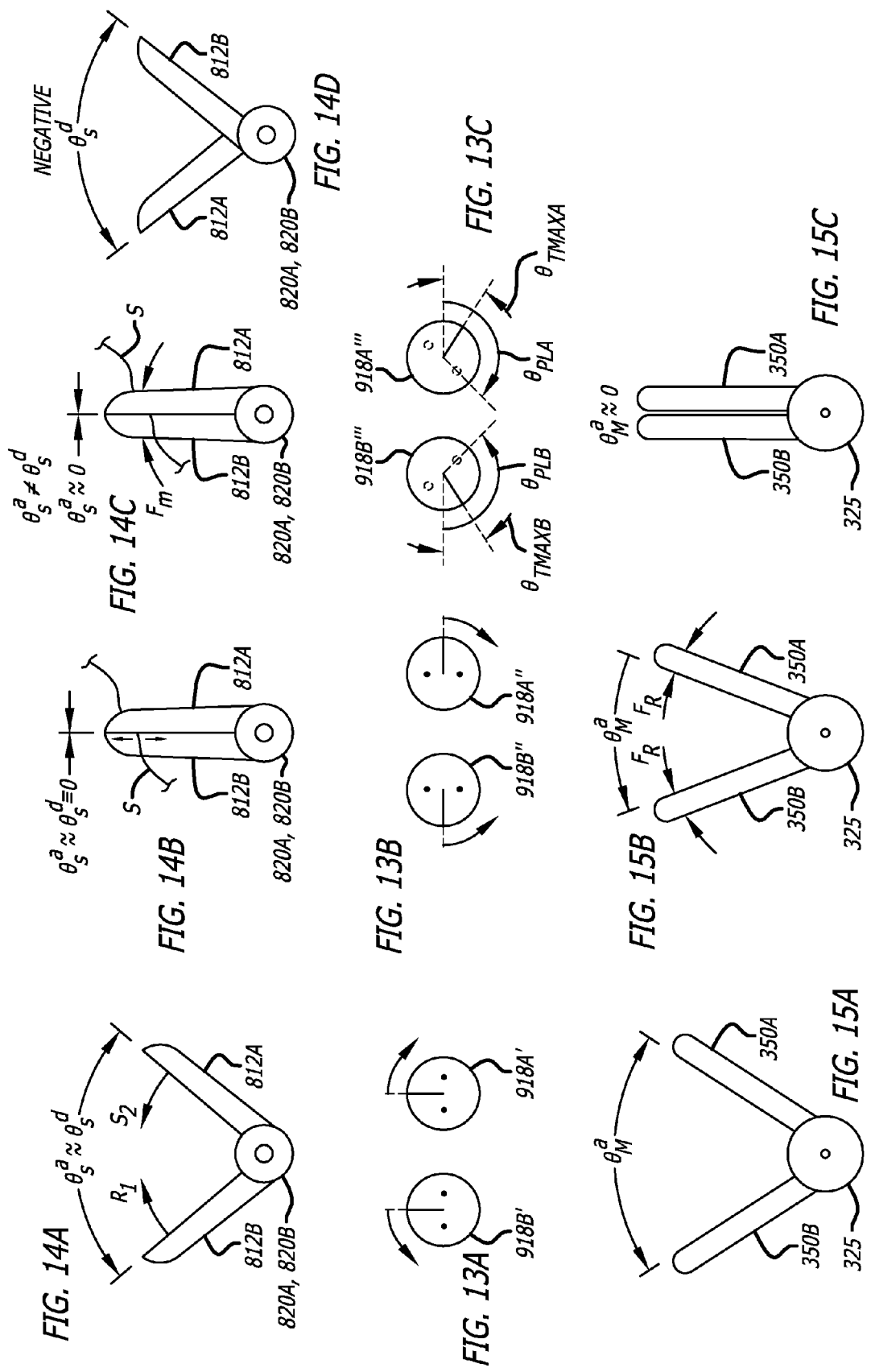

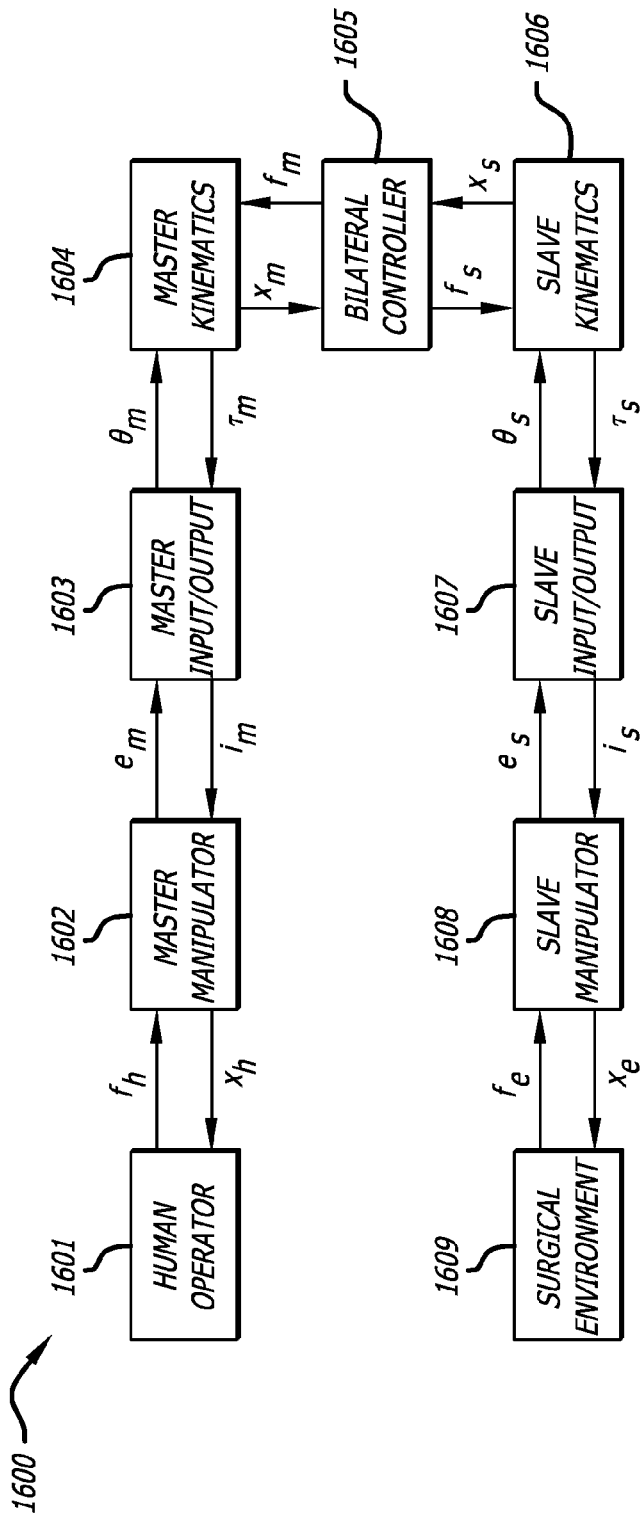
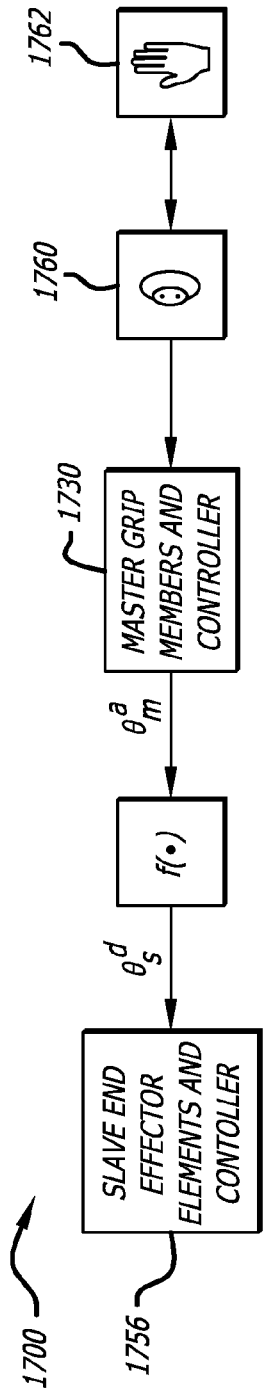
FIG. 16A
FIG. 17

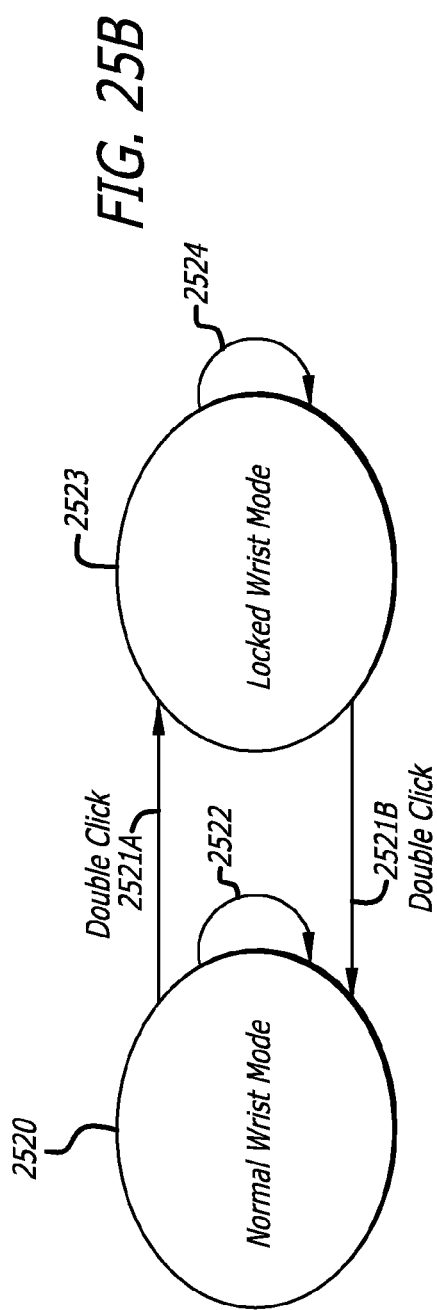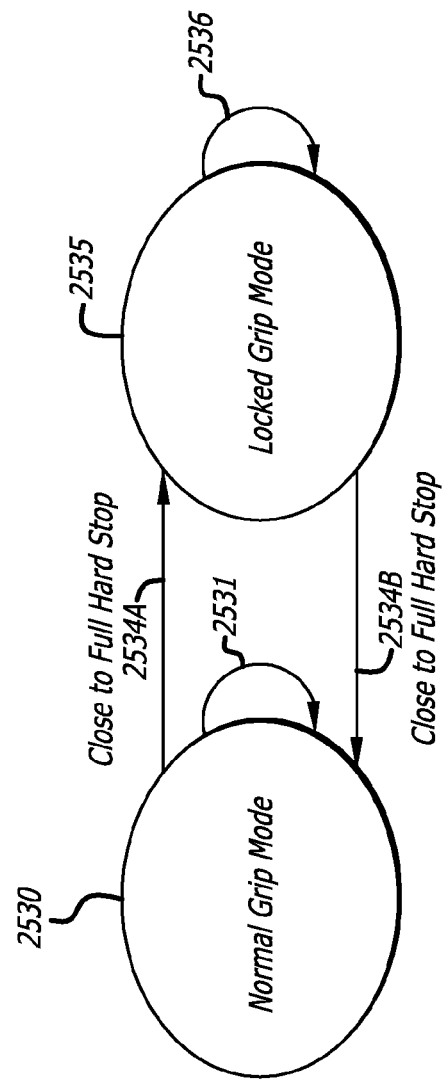
FIG. 25B
FIG. 25C

APPARATUS AND METHOD OF USER INTERFACE WITH ALTERNATE TOOL MODE FOR ROBOTIC SURGICAL TOOLS

CROSS-REFERENCE TO RELATED APPLICATIONS

This patent application claims the benefit of U.S. Provisional Patent Application No. 60/976,460 filed on Sep. 30, 2007 by inventors Nitish Swarup, et al., entitled USER INTERFACE WITH ALTERNATE TOOL MODE FOR ROBOTIC SURGICAL TOOLS.

FIELD

The embodiments of the invention are generally related to robotic surgical instruments or tools and robotic surgical systems.

BACKGROUND

Minimally invasive surgery typically limits the size of incisions into a human body so that the recovery from surgical procedures may be quick and the odds of infection reduced. However, only a few tools may be concurrently used by the same surgeon during minimally invasive surgery. Sometimes a tool change may occur to place the proper tool within the surgical site. A tool change may extend out the time of a minimally invasive surgical procedure.

Moreover, minimally invasive surgery may be burdensome on a surgeon, particularly when manually operating surgical controls for long periods of time.

BRIEF SUMMARY

The embodiments of the invention are summarized by the claims that follow below.

BRIEF DESCRIPTIONS OF THE DRAWINGS

FIG. 3B is a perspective view of an exemplary gimbaled device pivotally supporting a touch sensitive handle for the robotic surgical master control console of FIG. 3A to control robotic surgical tools including a robotic electro-surgical tool.

FIGS. 5A-5B are magnified views of a distal end of the robotic electro-surgical tool illustrated in FIG. 4A with gripping end effectors in a closed position.

FIG. 9 shows a schematic side view of the cable drive system of FIG. 8 in the robotic surgical tool and the robotic surgical arm with an interface there between.

FIGS. 13A-13C illustrate a variety of input disk positions to drive the end effectors.

FIGS. 14A-14C illustrate exemplary actual positions of the end effectors respectively corresponding to the input disk positions of FIGS. 13A-13C.

FIG. 14D illustrates a desired position of the end effectors that is not reached.

FIGS. 15A-15C illustrate exemplary positions of the master grips respectively corresponding to the input disk positions of FIGS. 13A-13C, the exemplary actual positions of the end effectors of FIGS. 14A-14C, and the desired position of the end effectors of FIG. 14D.

FIG. 16A schematically illustrates a high level control architecture model of a master/slave surgical robotic system.

Figure 16B:
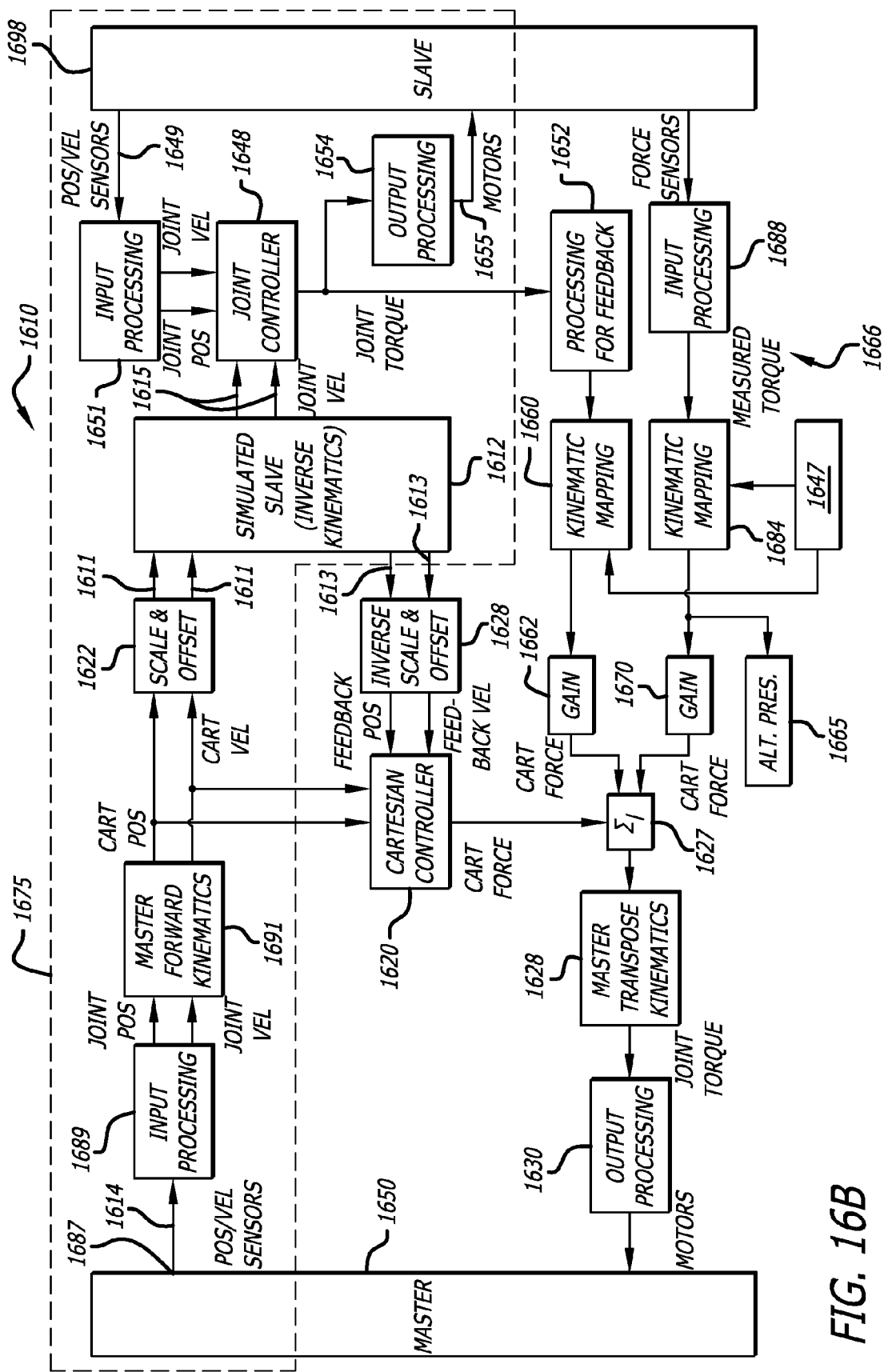

FIG. 16B shows a block diagram representing control steps followed by the control system of the minimally invasive surgical apparatus in effecting control between master positional and orientational movement and slave end effector positional and orientational movement.

FIG. 17 is a functional block diagram schematically illustrating an enhanced grip force master/slave arrangement in which a mechanical biasing mechanism provides tactile feedback to the system operator.

Figure 18A:
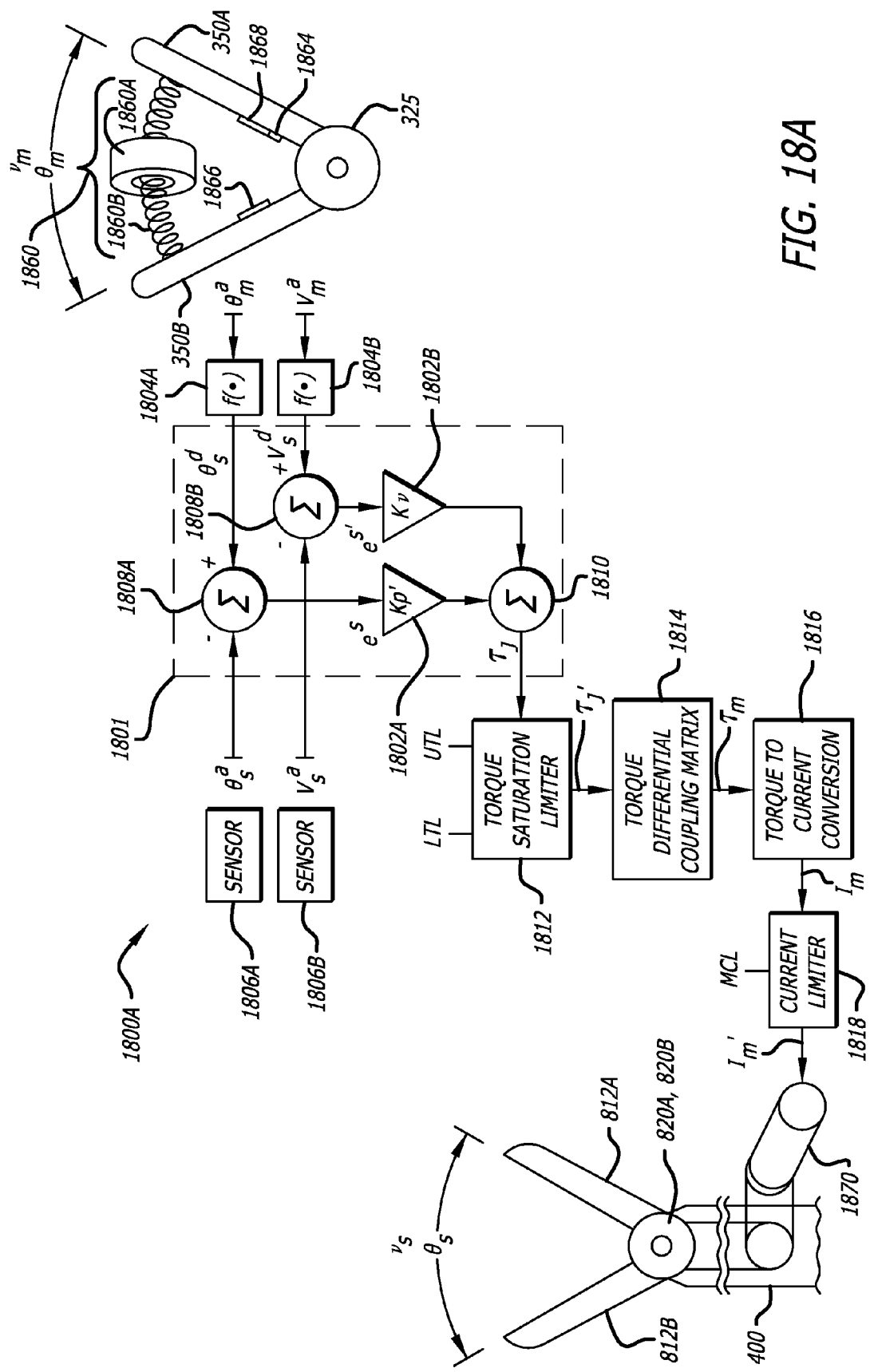
Figure 18B:
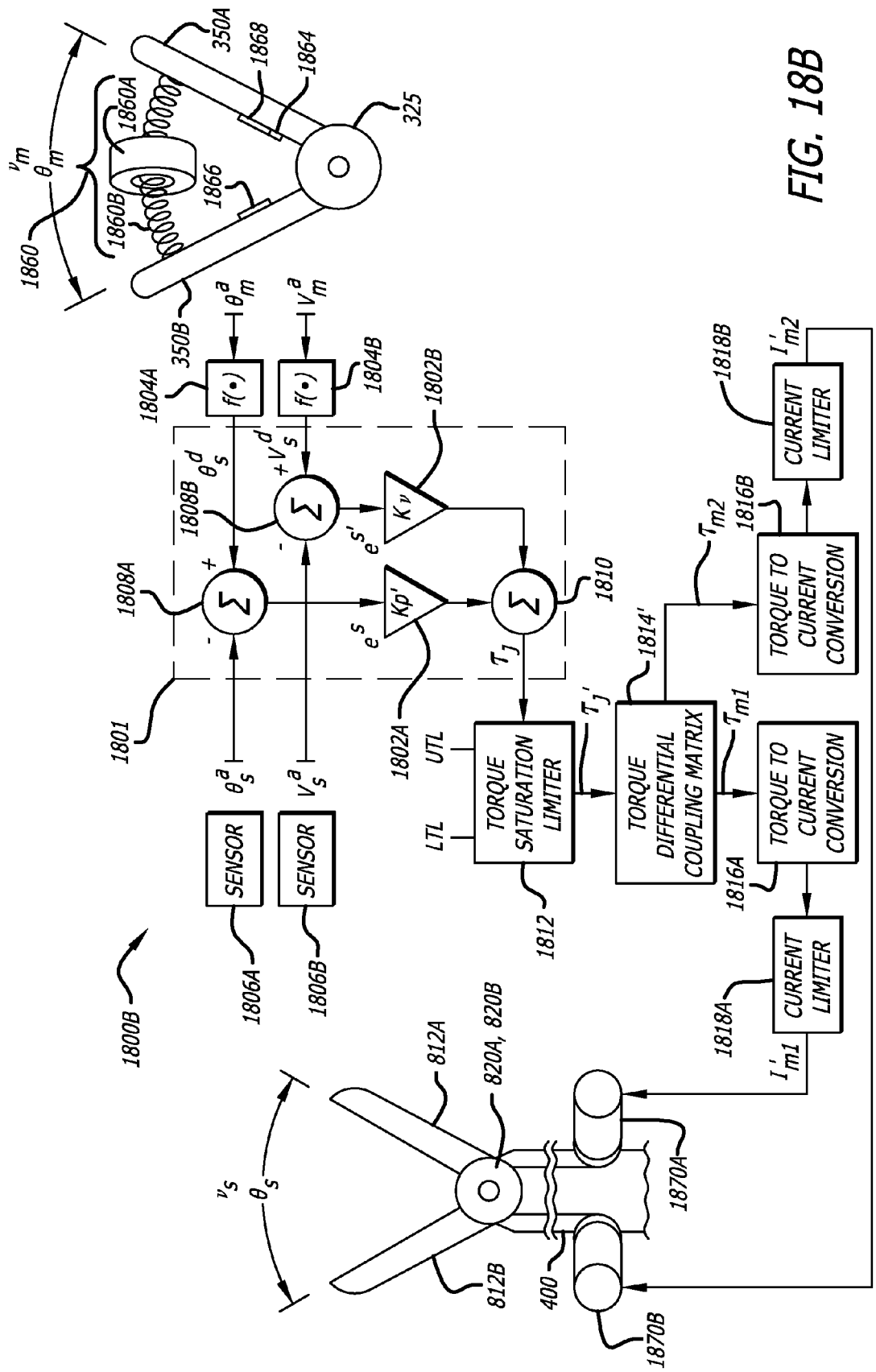

FIGS. 18A-18B schematically illustrate simplified master/slave control systems to provide a maximum joint torque limit at the joint of the end effectors.

Figure 19:
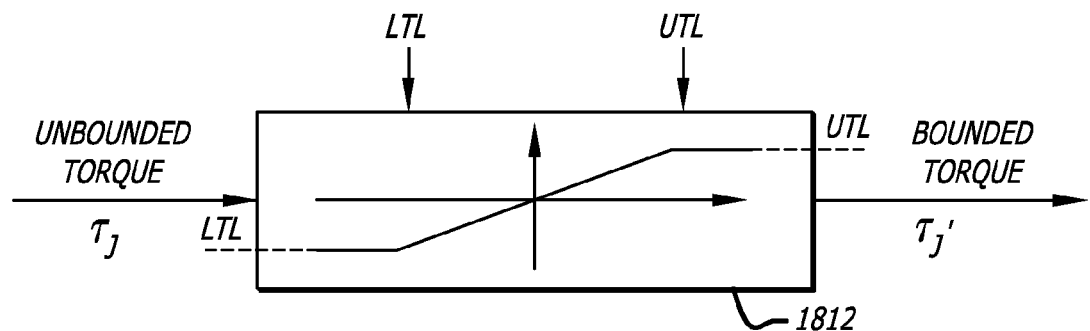

FIG. 19 illustrates a functional block diagram of the torque saturation limiter illustrated in FIGS. 18A-18B.

Figure 20:
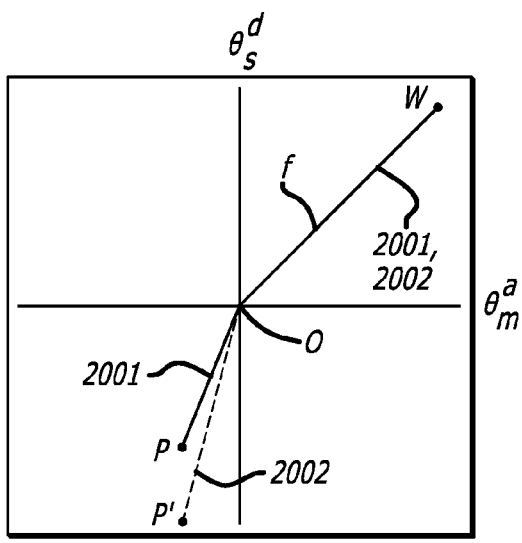

FIG. 20 graphically illustrates a function for enhancing an error signal by modifying the gain so that the master grip members can apply the maximum joint torque up to the maximum joint torque limits at the joint of the end effectors.

Figure 21A:
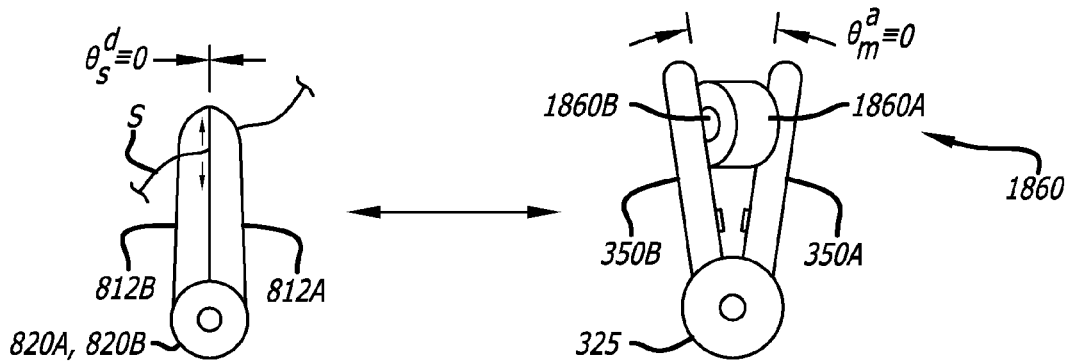
Figure 21B:
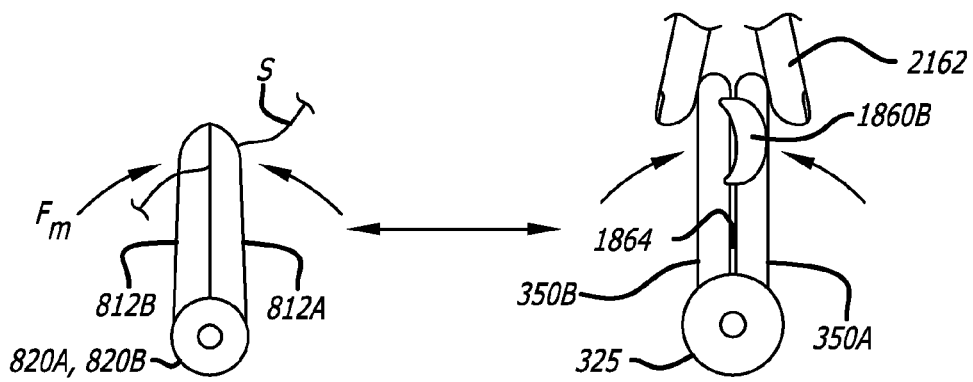

FIGS. 21A-21B schematically illustrate the use of the master grip members to apply the maximum joint torque limit to the joint at the end effectors.

Figure 22A:
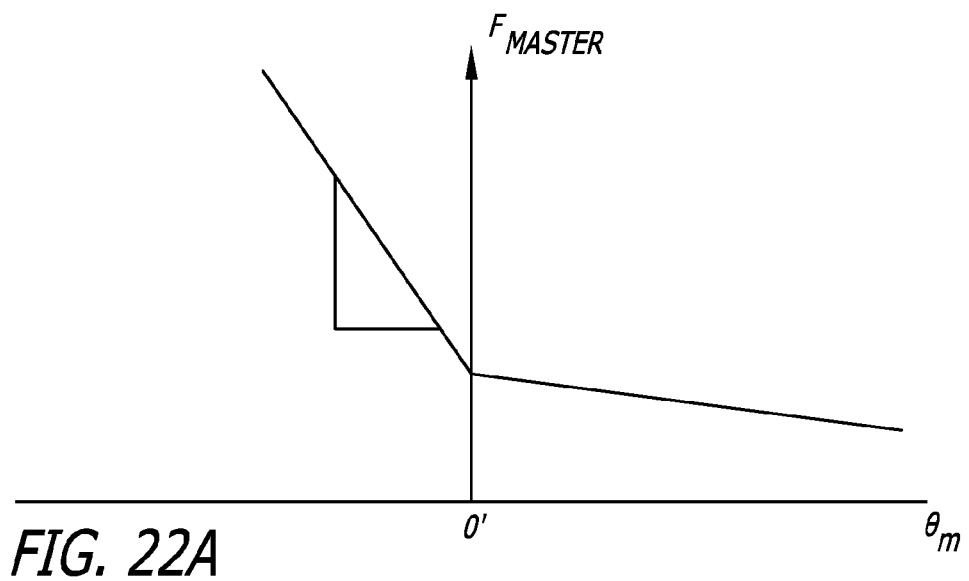

FIG. 22A graphically illustrates end effector forces.

Figure 22B:
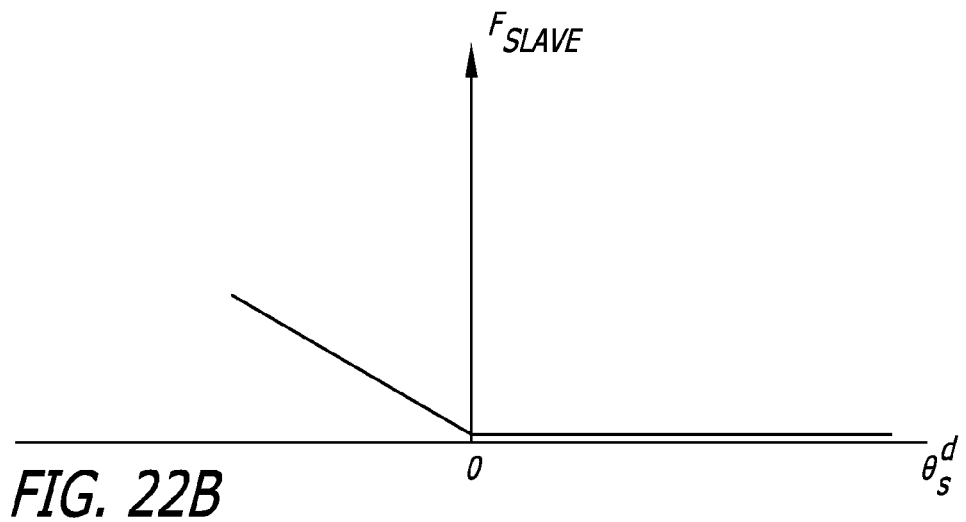

FIG. 22B graphically illustrates master grip forces corresponding to the end effector forces illustrated in FIG. 22A.

Figure 23:
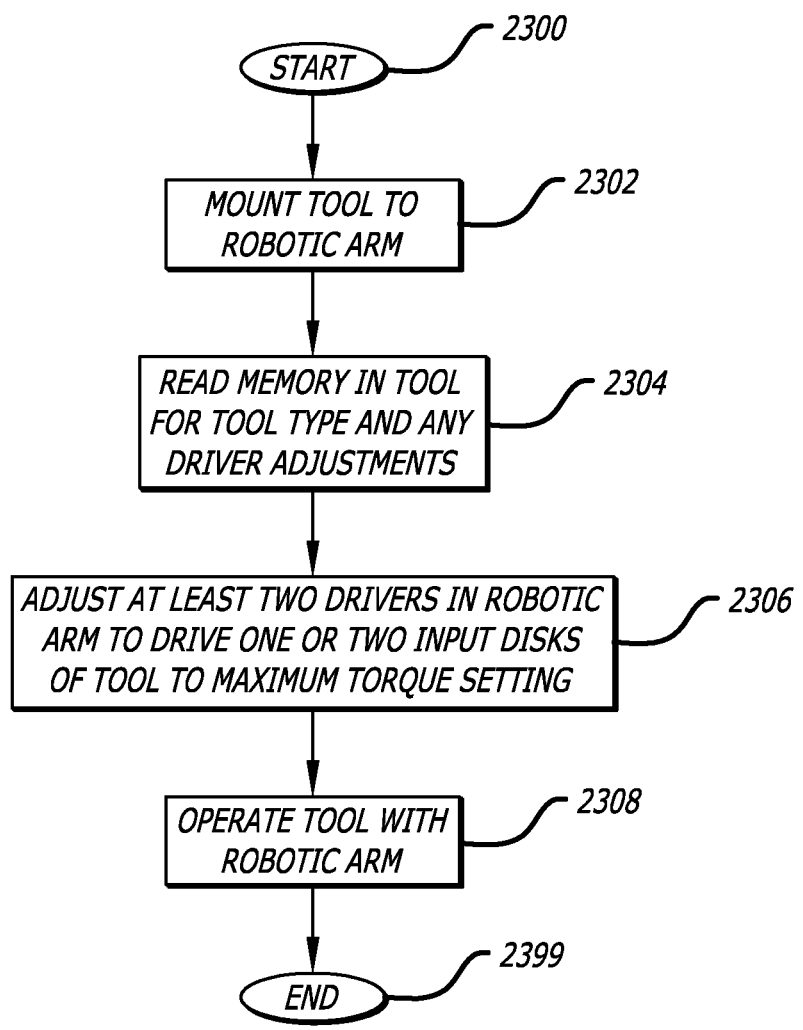

FIG. 23 is a flow chart that illustrates an exemplary method of system setup with torque limited drivers for robotic surgical tools.

Figure 24:
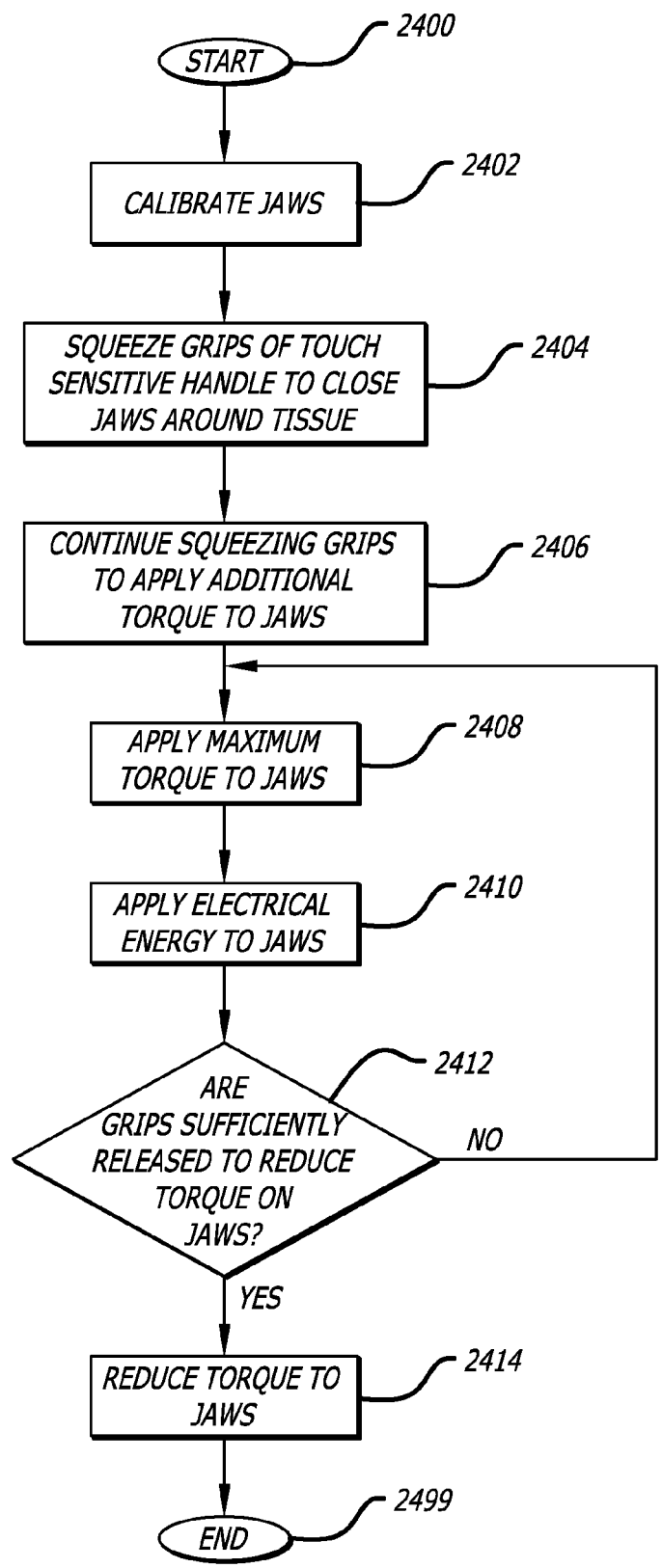

FIG. 24 is a flow chart that illustrates an exemplary method of operation of robotic surgical tools with torque limited drivers.

Figure 25A:
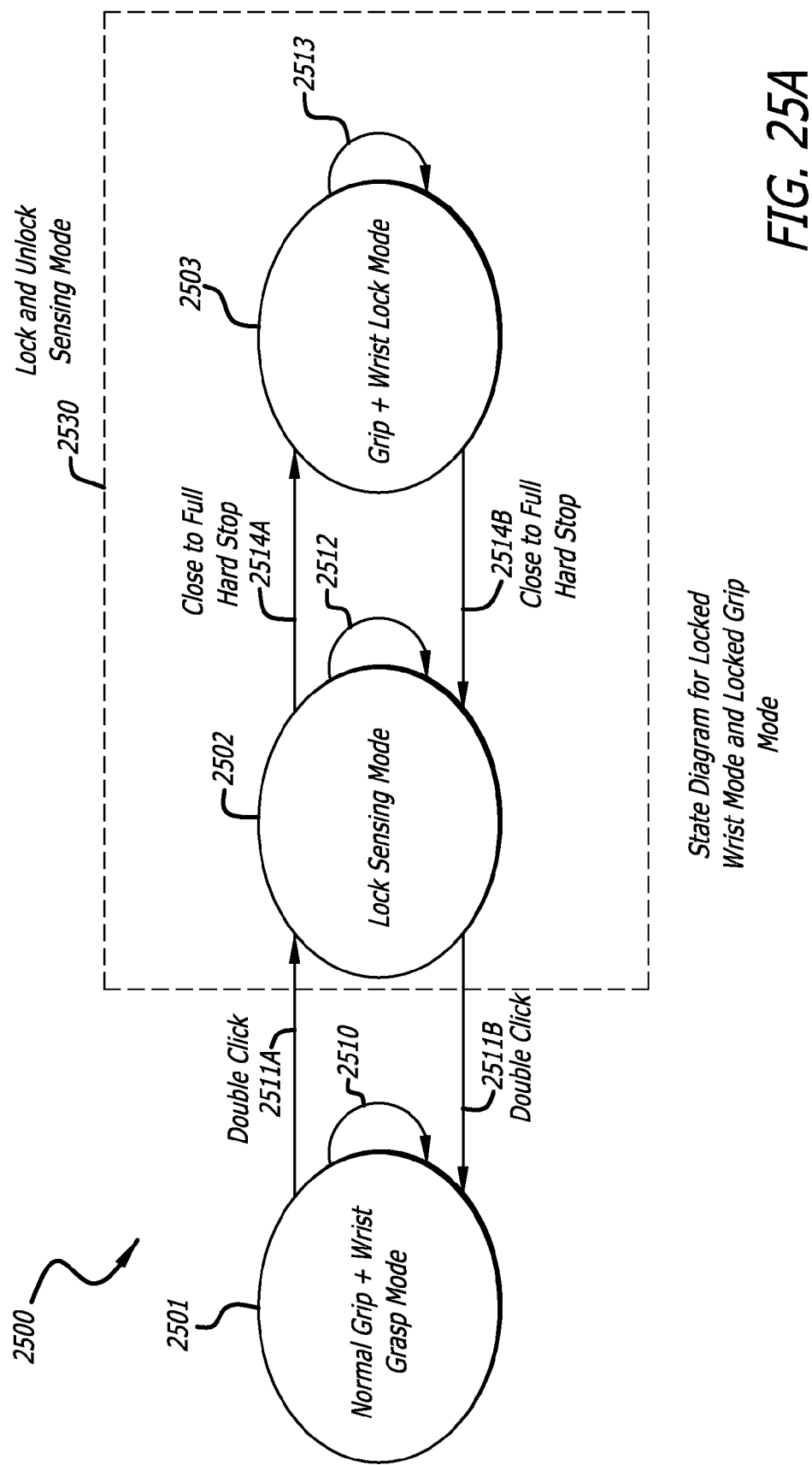

FIG. 25A is a state diagram for one implementation of a state machine.

FIG. 25B is a state diagram for another implementation of a state machine.

FIG. 25C is a state diagram for another implementation of a state machine.

Figure 25D:
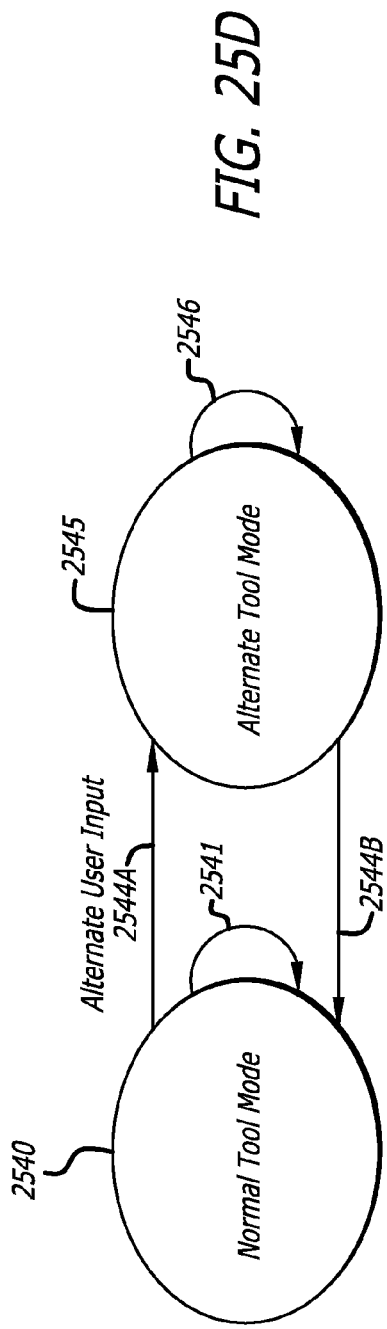

FIG. 25D is a state diagram for an implementation of a state machine with an alternate user input and sensing thereof.

Figure 25E:
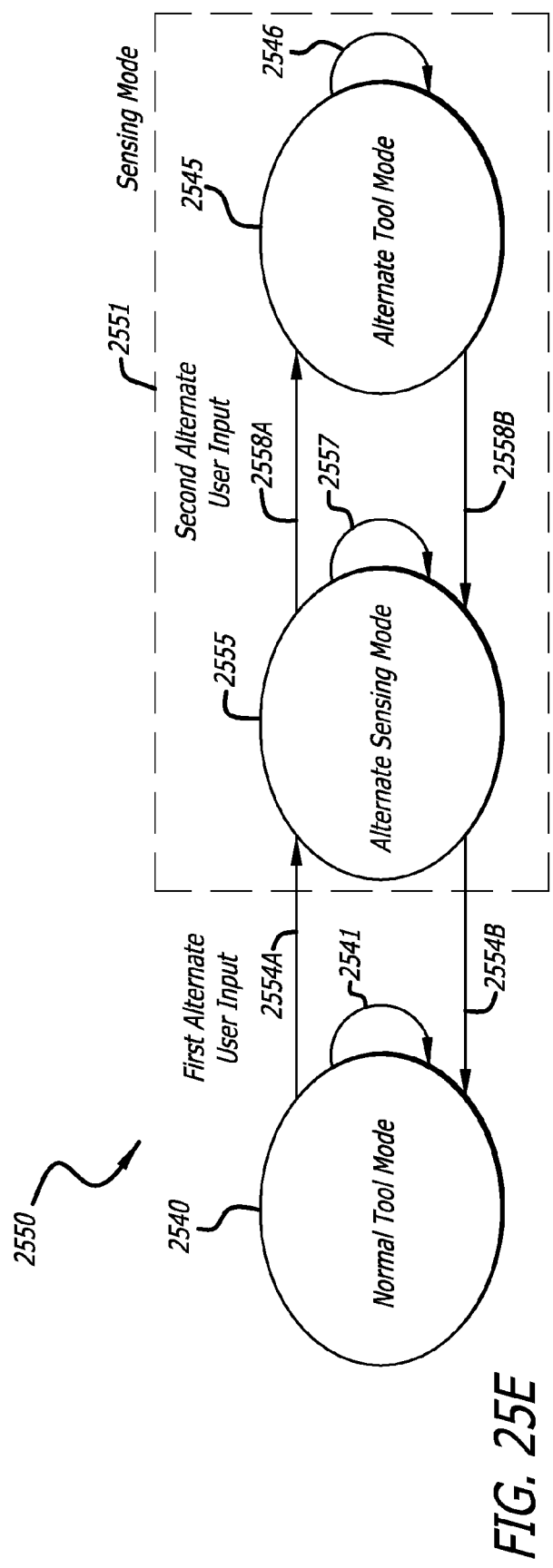

FIG. 25E is a state diagram for another implementation of a state machine with an alternate user input and sensing thereof.

Figure 26A:
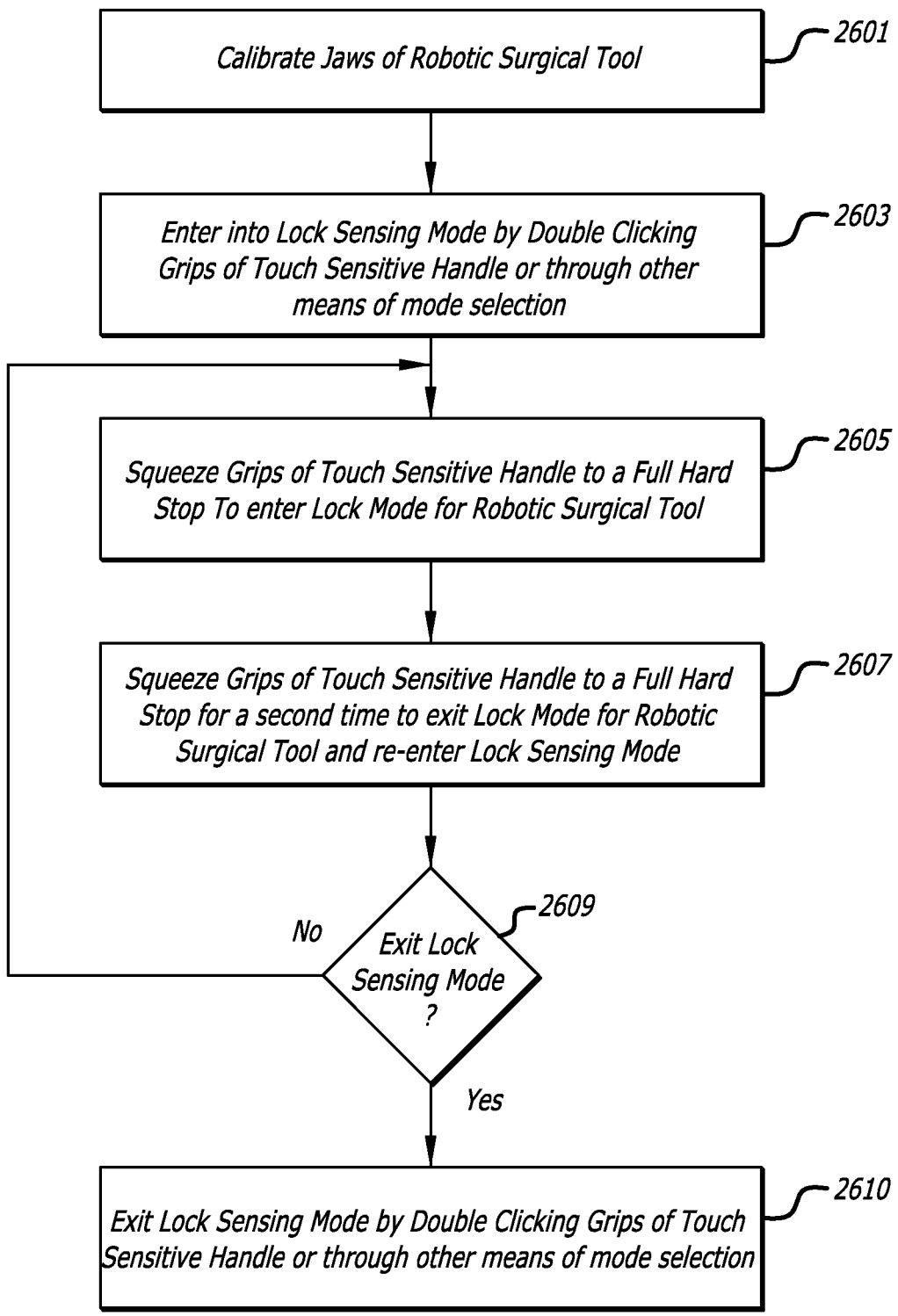

FIG. 26A is a flow chart of a method of using a double click user interface.

Figure 26B:
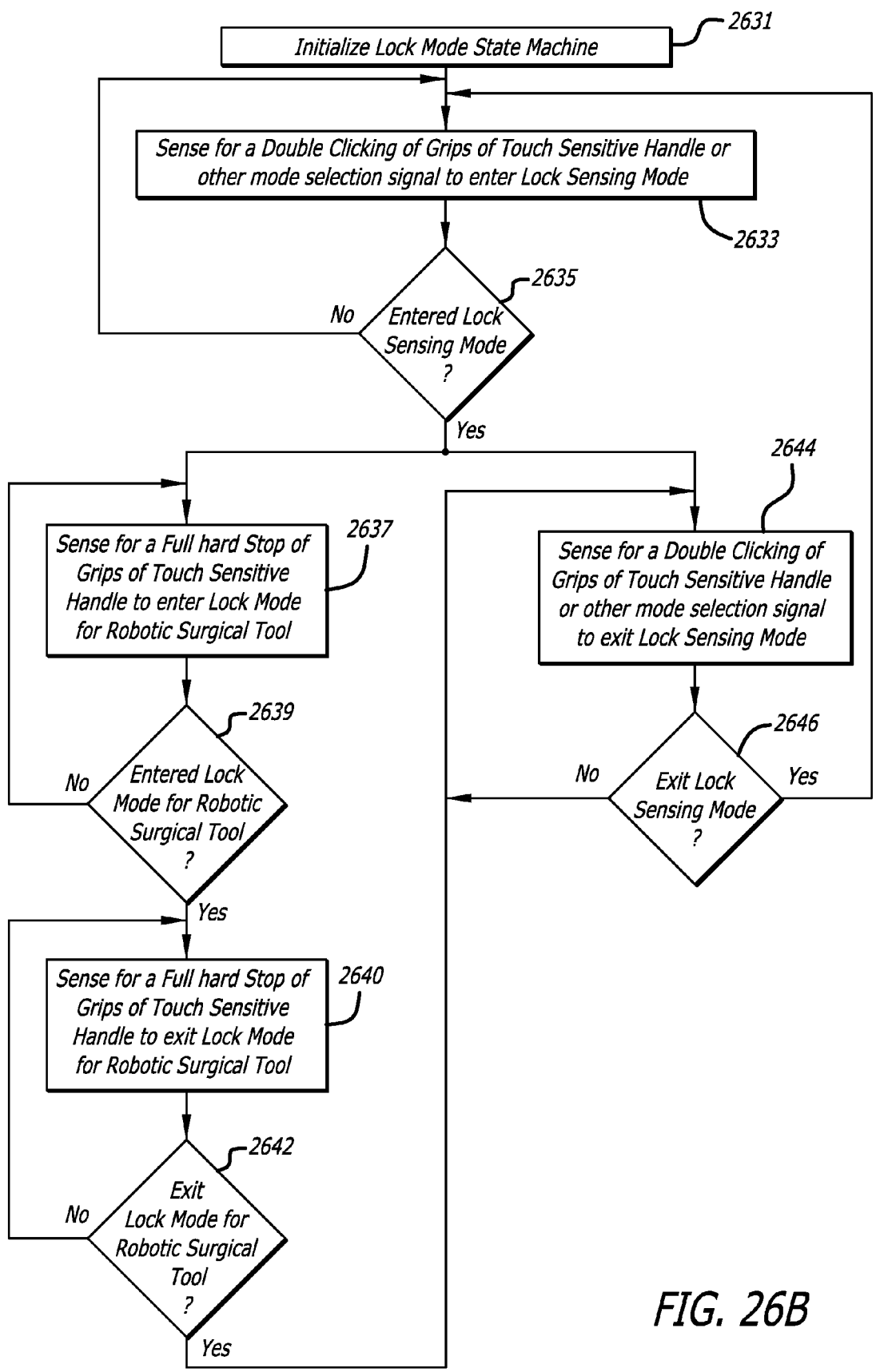

FIG. 26B is a flow chart of a method of operation of a double click user interface.

Figure 27:
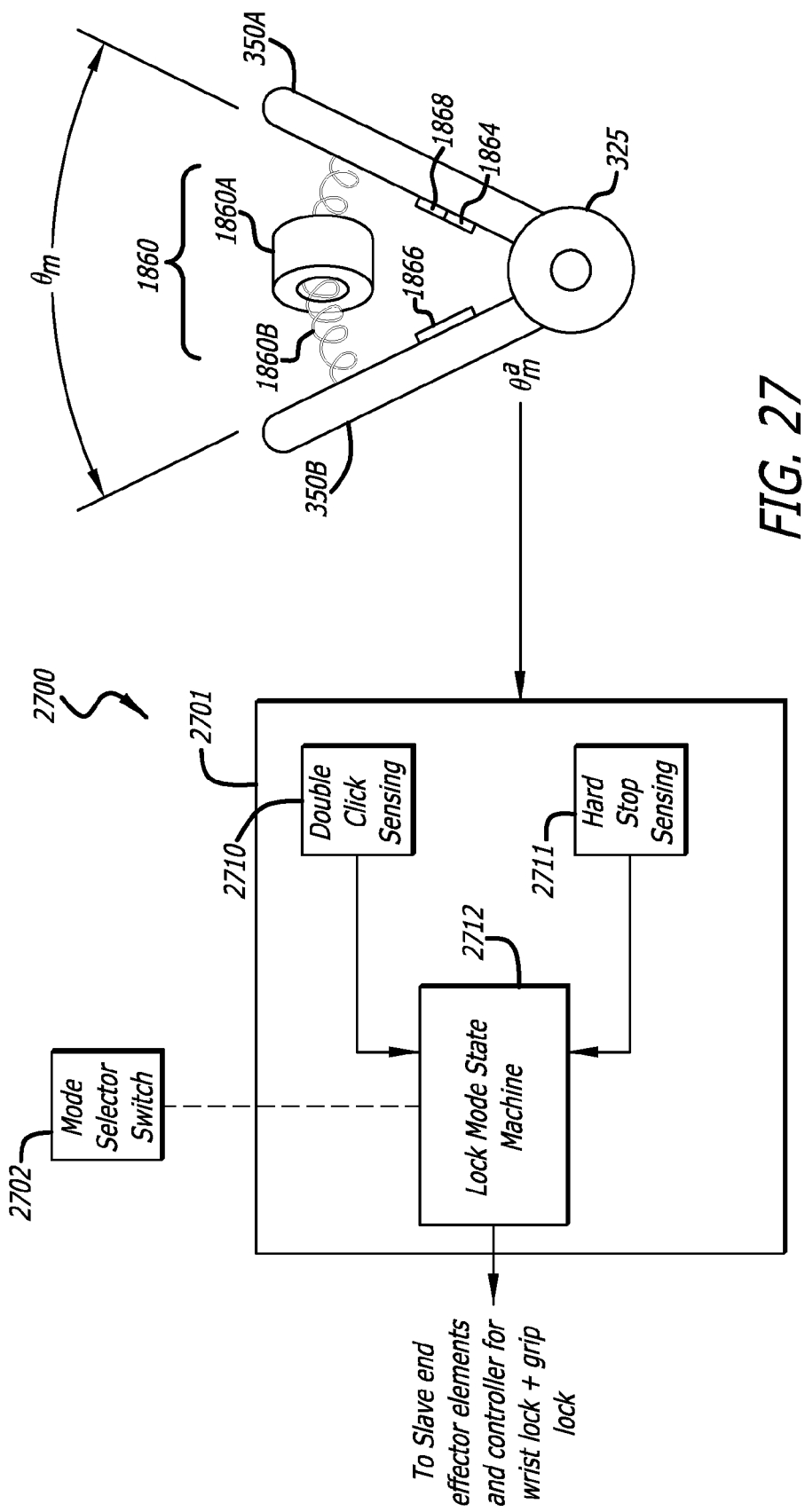

FIG. 27 is a functional block diagram of a user interface system receiving master grip angles from the master grips of a touch sensitive handle.

Note that these figures are for illustration purposes and do not necessarily reflect the actual shape, size, or dimensions of objects being illustrated.

DETAILED DESCRIPTION

In the following detailed description of the embodiments of the invention, numerous specific details are set forth in order to provide a thorough understanding of the embodiments of the invention. However, the embodiments of the invention may be practiced without these specific details. In other instances, well known methods, procedures, components, and circuits have not been described in detail so as to not unnecessarily obscure aspects of the embodiments of the invention.

INTRODUCTION

The embodiments of the invention include methods, apparatus, and systems to provide a locking mode for robotic surgical tools.

In one embodiment of the invention, a user interface system for a robotic surgical system is provided including a first alternate sensing process, a second alternate sensing process and a state machine. The first alternate sensing process is provided to detect a first alternate user input of a control input mechanism to enter an alternate sensing mode for the robotic surgical system. The second alternate sensing process is provided to detect a second alternate user input of a control input mechanism to enter an alternate tool mode. The state machine is provided in operational communication with the first alternate sensing process and the second alternate sensing process. The state machine controls a robotic surgical tool in an alternate manner in response to the state machine being in an alternate tool mode.

In another embodiment of the invention a method for a robotic surgical system is provided including the method of sensing for a first alternate user input signal to enter an alternate tool mode; the method of alternatively controlling a robotic surgical tool in response to the alternative tool mode; and in the alternate tool mode, the method of sensing for the first alternate user input signal to exit the alternate tool mode.

In still another embodiment of the invention, a user interface system for a robotic surgical instrument having a number of degrees of freedom of movement is disclosed, including a double click sensing process to detect two closure cycles of a control input mechanism within a predetermined period of time; a hard stop sensing process to detect a predetermined percentage of a hard stop in the movement of the control input mechanism, and a state machine operationally in communication with the double click sensing process and the hard stop sensing process. The state machine switchably reduces the number of degrees of freedom of movement in the robotic surgical instrument in response to two closure cycles of the control input mechanism within the predetermined period of time and movement of the control input mechanism exceeding the predetermined percentage of the hard stop.

In still another embodiment of the invention, a method for a robotic surgical instrument is provided including entering a lock sensing mode for a robotic surgical instrument; in the lock sensing mode, switchably reducing degrees of freedom of movement in the robotic surgical instrument and switchably clamping one or more end effectors of the robotic surgical in response to the degrees of freedom of movement in the robotic surgical instrument being reduced.

In yet another embodiment of the invention, a method for a robotic surgical system is disclosed including sensing for a first mode selection signal to enter a lock sensing mode; sensing for a first hard stop in a control input mechanism to enter a lock mode for a robotic surgical tool; sensing for a second hard stop in the control input mechanism to exit the lock mode for the robotic surgical tool; and sensing for a second mode selection signal to exit the lock sensing mode.

Robotic Surgical Systems

Robotic surgery generally involves the use of a robot manipulator that has multiple robotic manipulator arms. One or more of the robotic manipulator arms often support a surgical tool which may be articulated (such as jaws, scissors, graspers, needle holders, micro dissectors, staple appliers, tackers, suction/irrigation tools, clip appliers, or the like) or non-articulated (such as cutting blades, cautery probes, irrigators, catheters, suction orifices, or the like). One or more of the robotic manipulator arms are often used to support a surgical image capture device such as an endoscope (which may be any of a variety of structures such as a laparoscope, an arthroscope, a hysteroscope, or the like), or, optionally, some other imaging modality (such as ultrasound, fluoroscopy, magnetic resonance imaging, or the like). Typically, the arms will support at least two surgical tools corresponding to the two hands of a surgeon and one image capture device.

Robotic surgery may be used to perform a wide variety of surgical procedures, including but not limited to open surgery, neurosurgical procedures (such as stereotaxy), endoscopic procedures (such as laparoscopy, arthroscopy, thoracoscopy), and the like.

Figure 1:
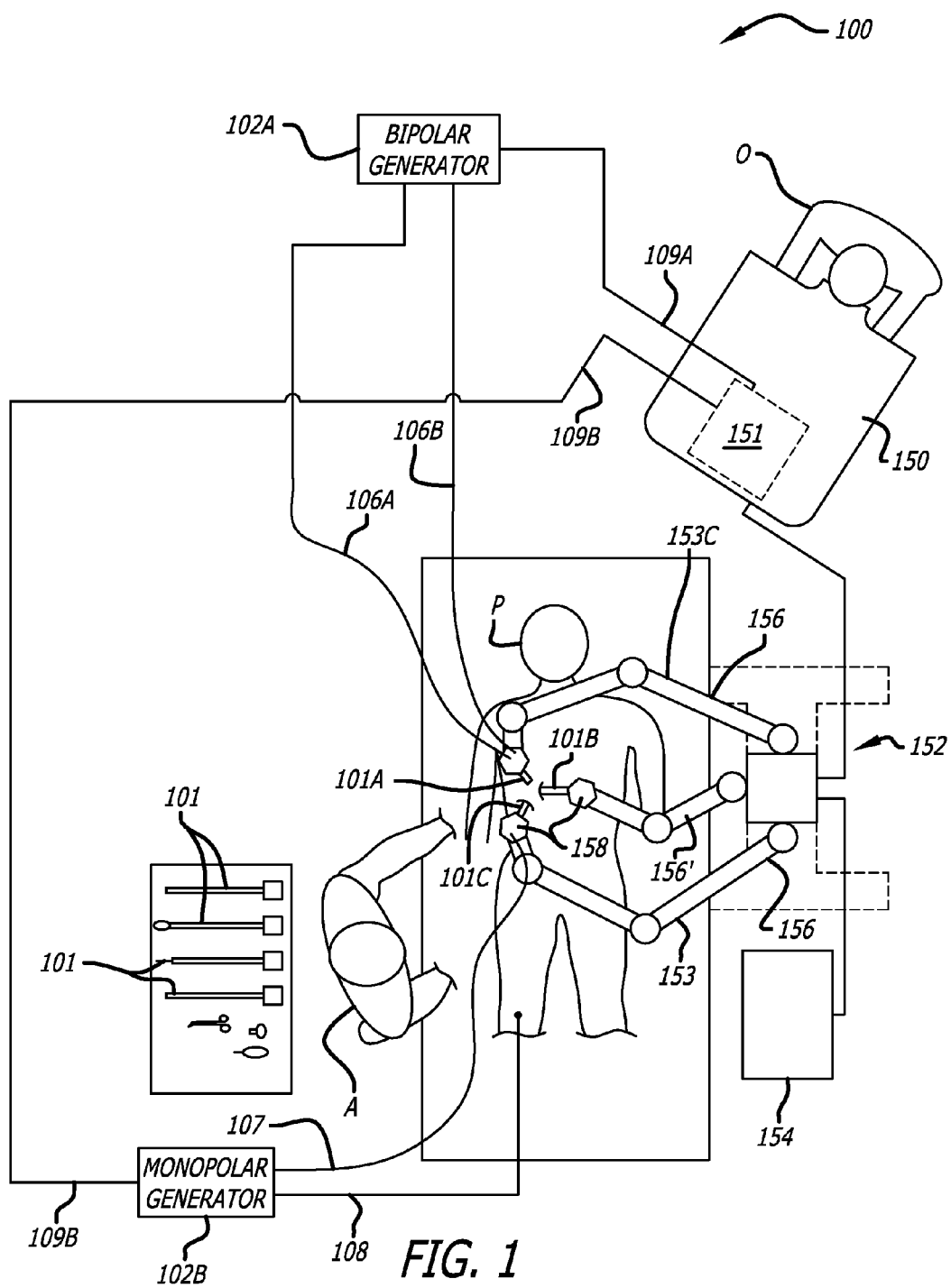
FIG. 1 is a block diagram of a robotic surgery system to perform minimally invasive robotic surgical procedures using a robotic electro-surgical tool.

Referring now to FIG. 1, a block diagram of a robotic surgery system 100 is illustrated to perform minimally invasive robotic surgical procedures using robotic electro-surgical tools 101A and 101C. Each of the robotic electro-surgical tools 101A and 101C are robotic endoscopic surgical instrument that are manipulated by a slaved robotic manipulator and remotely controlled by control signals received from a master control console. In contrast, manual endoscopic surgical instruments are directly controlled by hand. Robotic electro-surgical tool 101A is a bipolar electro-surgical tool. Robotic electro-surgical tool 101C is a mono-polar electro-surgical tool.

A user or operator O (generally a surgeon) performs a minimally invasive surgical procedure on patient P by manipulating input devices at a master control console 150. A computer 151 of the console 150 directs movement of robotically controlled endoscopic surgical instruments (generally numbered 101), effecting movement of the instruments using a robotic surgical manipulator 152. The robotic surgical manipulator 152 may also be referred to as robotic patient-side cart system or simply as a cart. The robotic surgical manipulator 152 has one or more robotic arms 153. Typically, the robotic surgical manipulator 152 includes at least three robotic manipulator arms 153 supported by linkages, with a central arm supporting an endoscopic camera and the robotic surgical arms 153 to left and right of center supporting tissue manipulation tools and the robotic surgical tool 101A.

An assistant A may assist in pre-positioning of the robotic surgical manipulator 152 relative to patient P as well as swapping tools or instruments 101 for alternative tool structures, and the like, while viewing the internal surgical site via an assistant's display 154. The image of the internal surgical site shown to A by the assistant's display 154 and operator O by surgeon's console 150 is provided by one of the surgical instruments 101 supported by the robotic surgical manipulator 152.

Generally, the robotic arms 153 of robotic surgical manipulator 152 include a positioning portion and a driven portion. The positioning portion of the robotic surgical manipulator 152 remains in a fixed configuration during surgery while manipulating tissue. The driven portion of the robotic surgical manipulator 152 is actively articulated under the direction of the operator O generating control signals at the surgeon's console 150 during surgery. The actively driven portion of the arms 153 is herein referred to as an actuating portion 158. The positioning portion of the robotic arms 153 that are in a fixed configuration during surgery may be referred to as positioning linkage and/or "set-up joint" 156, 156'.

To support electro-surgical robotic tools 101A, 101B, the robotic surgical system 100 may further include one or more electrosurgical generators 102A-102B. The one or more electrosurgical generators 102A-102B are controlled by the master console 150 over the control cables 109A-109B by a surgeon operating the master console.

The electrosurgical generator 102A is a bipolar generator. A pair of wires 106A-106B couple between the bipolar electrosurgical generator 102A and a bipolar electrosurgical robotic tool 101A. The pair of wires pair of wires 106A-106B may transfer the energy of the bipolar electrosurgical generator 102A to a respective pair of end effectors of the bipolar electrosurgical robotic tool 101A to cauterize or seal tissue.

The electrosurgical generator 102B is a monopolar generator. A wire 107 couples between the monopolar electrosurgical generator 102B and a monopolar electrosurgical robotic tool 101B. A ground wire 108 couples between the monopolar electrosurgical generator 102B and patient P. The wire 107 may transfer the energy of the monopolar electrosurgical generator 102B to an end effector of the monopolar electrosurgical robotic tool 101B to cauterize or seal tissue.

Figure 2A:
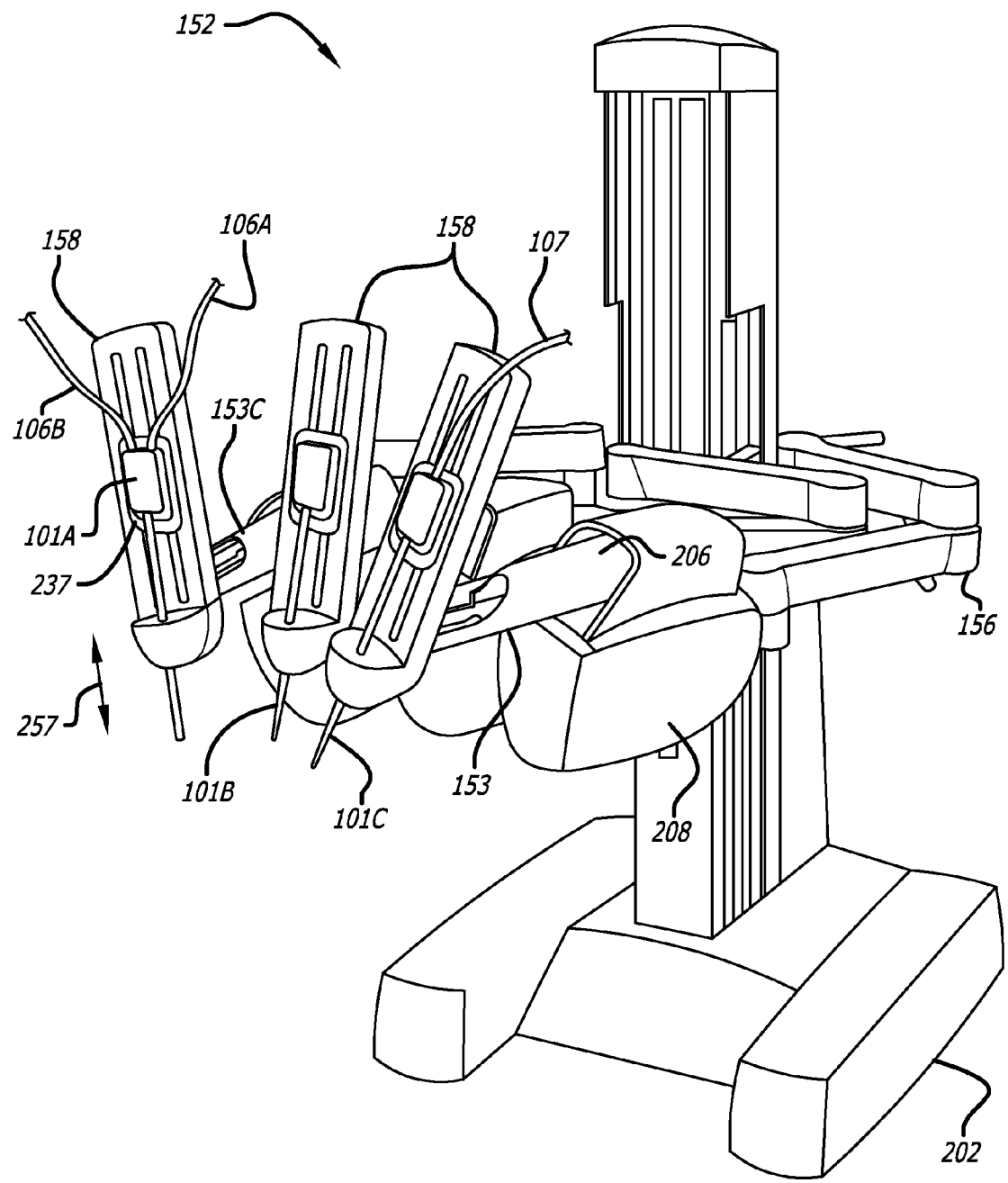
FIG. 2A is a perspective view of a robotic surgical manipulator with a plurality of robotic surgical arms at least one of which includes a robotic electro-surgical tool.

Referring now to FIG. 2A, a perspective view of the robotic surgical manipulator 152 is illustrated. The robotic surgical manipulator 152 has one or more robotic surgical arms 153. The robotic arm 153C includes an electro-surgical robotic tool 101A coupled thereto. The robotic surgical manipulator 152 further includes a base 202 from which the robotic surgical instruments 101 may be supported. More specifically, the robotic surgical instruments 101 are each supported by the positioning linkage 156 and the actuating portion 158 of the arms 153. It should be noted that these linkage structures are here illustrated with protective covers 206,208 extending over much of the robotic arms. It should be understood that these protective covers 206,208 are optional, and may be limited in size or entirely eliminated in some embodiments to minimize the inertia that is manipulated by the servomechanism, and to limit the overall weight of robotic surgical manipulator 152.

Each of the robotic surgical tools 101A-101C, releasably couple to a moveable carriage 237 near an end of each robotic surgical arm. Each moveable carriage 237, with the robotic surgical tool mounted thereto, can be driven to translate along a linear guide formation 260 in the actuating portion 158 of the robotic surgical arms 153 in the direction of arrow 257.

The robotic surgical manipulator 152 generally has dimensions suitable for transporting between operating rooms. It typically can fit through standard operating room doors and onto standard hospital elevators. The robotic surgical manipulator 152 may have a weight and a wheel (or other transportation) system that allows the cart to be positioned adjacent an operating table by a single attendant. The robotic surgical manipulator 152 may be sufficient stable during transport to avoid tipping, and to easily withstand overturning moments that may be imposed at the ends of the robotic arms during use.

Figure 2B:
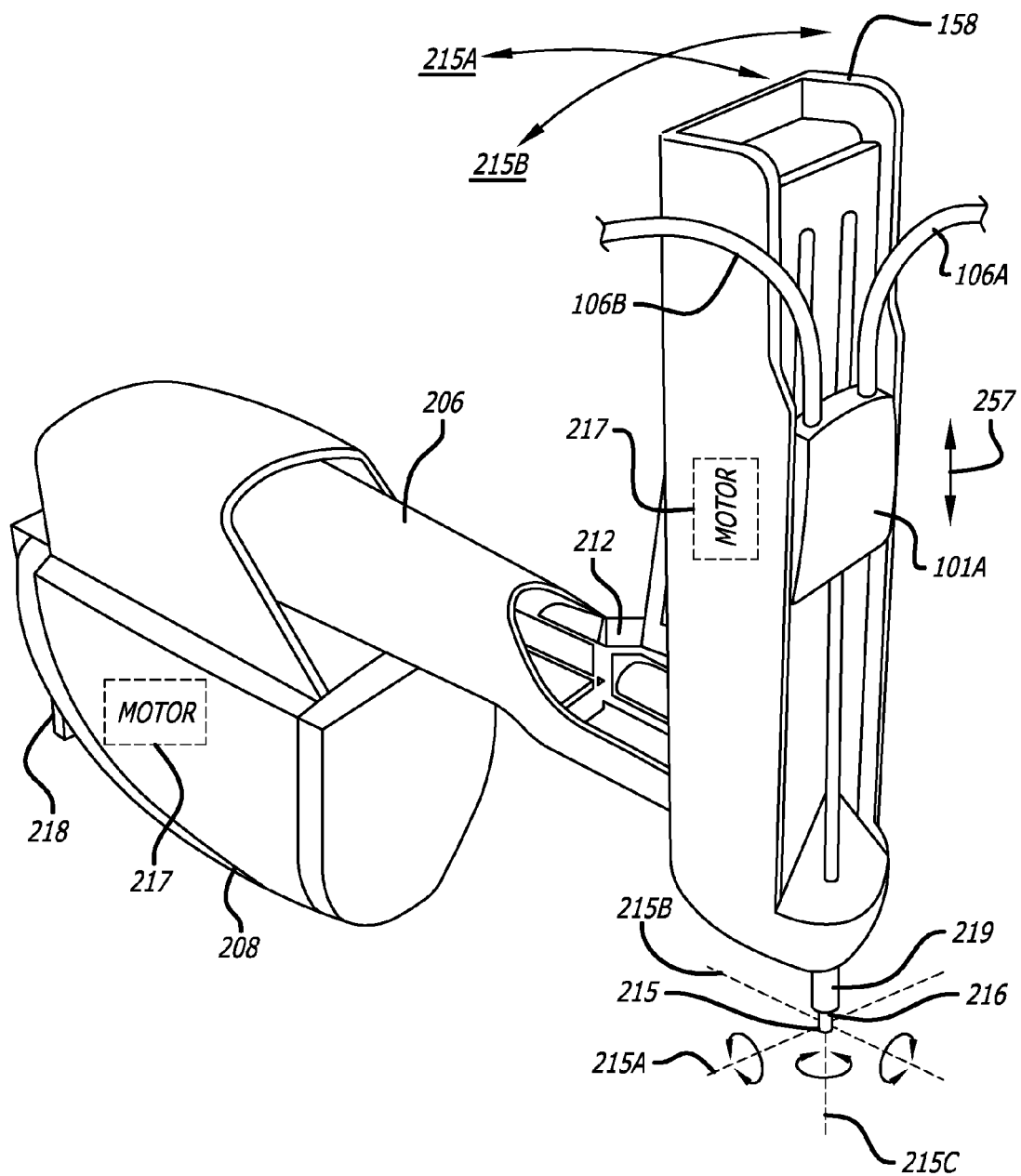
FIG. 2B is a perspective view of the robotic surgical arm including the robotic electro-surgical tool mounted thereto.

Referring now to FIG. 2B, a perspective view of the robotic surgical arm 153C is illustrated including the electro-surgical robotic tool 101A mounted thereto. Each of the robotic manipulating arms 153 preferably includes a linkage 212 that constrains the movement of the surgical tool 101 mounted thereto. More specifically, linkage 212 includes rigid links coupled together by rotational joints in a parallelogram arrangement so that the robotic surgical tool 101A rotates around a point 215 in space. At the point 215, the robotic arm can pivot the robotic surgical tool 101A about a pitch axis 215A and a yaw axis 215B. The pitch and yaw axes intersect at the point 215, which is aligned along a shaft 216 of robotic surgical tool 101A. The shaft is a rotatable hollow tube with a number of cables of a cable drive system therein.

The robotic arm provides further degrees of freedom of movement to the robotic surgical tool 101A. Along an insertion axis 215C, parallel to the central axis of the shaft 216 of the robotic surgical tool 101A, the robotic surgical tool 101A may slide into and out from a surgical site as indicated by arrow 257. The robotic surgical tool 101A can also rotate about the insertion axis 215C. As the robotic surgical tool 101A slides along or rotates about the insertion axis 215C, the center point 215 is relatively fixed with respect to the base 218. That is, the entire robotic arm is generally moved in order to maintain or re-position back to the center point 215.

The linkage 212 of the robotic arm 153 is driven by a series of motors 217 therein in response to commands from a processor or computer. The motors 217 in the robotic arm are also used to rotate and/or pivot the robotic surgical tool 101A at the point 215 around the axes 215A-215C. If a robotic surgical tool 101 further has end effectors to be articulated or actuated, still other motors 217 in the robotic arm may be used to do so. Additionally, the motion provided by the motors 217 may be mechanically transferred to a different location such as by using pulleys, cables, gears, links, cams, cam followers, and the like or other known means of transfer, such as pneumatics, hydraulics, or electronics.

For endoscopic surgical procedures, the actuating portion 158 of the robotic arm 153 is often fitted with a hollow cannula 219. The shaft or tube of the robotic surgical tool 101 may be inserted into the hollow cannula 219. The cannula 219, which may be releasably coupled to the robotic arm 153, supports the shaft or tube of the robotic surgical tool 101, preferably allowing the tool to rotate around the axis 215C and move axially through the central bore of the cannula along the axis 215C.

The robotic surgical tools 101 are generally sterile structures, often being sterilizable and/or being provided in hermetically sealed packages for use. As the robotic surgical tools 101 will be removed and replaced repeatedly during many procedures, a tool holder could potentially be exposed to contamination if the interface directly engages the tool holder. To avoid contamination to a tool holder and possible cross contamination between patients, an adaptor for coupling to robotic surgical tools 101 is provided in a robotic arm of the robotic surgical manipulator.

Figure 4F:
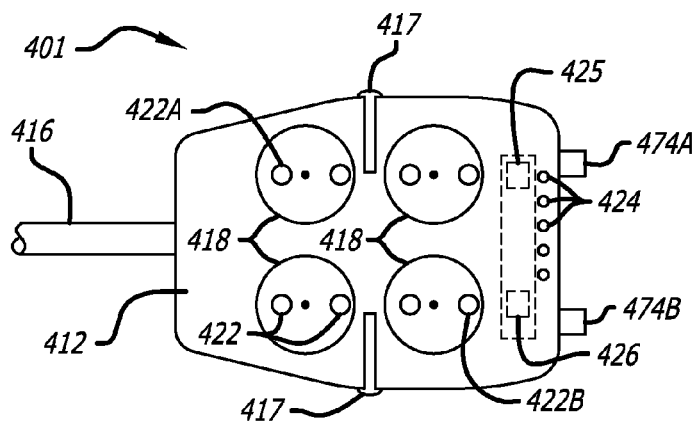
FIGS. 4A-4G illustrate an exemplary robotic electro-surgical instrument or tool with a gripping end effector.
Figure 2D:
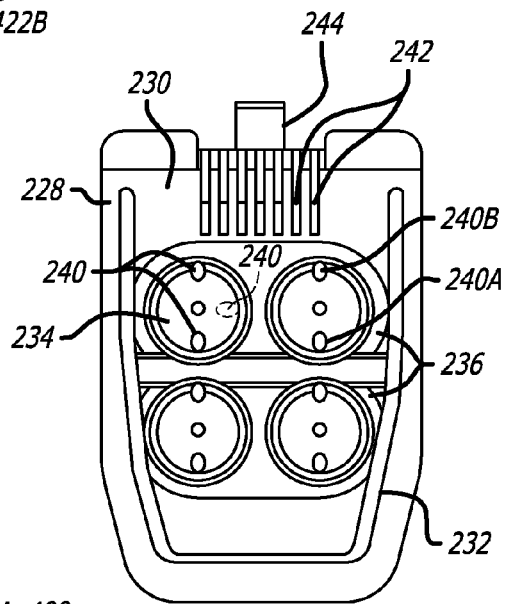
FIG. 2D illustrates a top view of the adapter of the robotic surgical arm of FIG. 2C to which the robotic electro-surgical tool may be mounted.
Figure 2C:
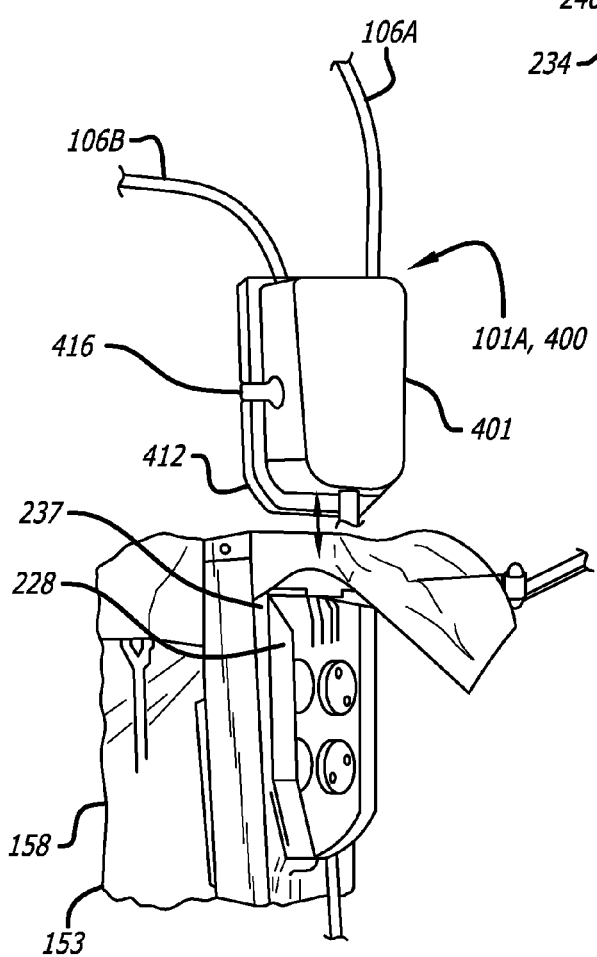
FIG. 2C illustrates mounting of the robotic electro-surgical tool to an adapter of the robotic surgical arm of FIG. 2B.
Figure 4A:
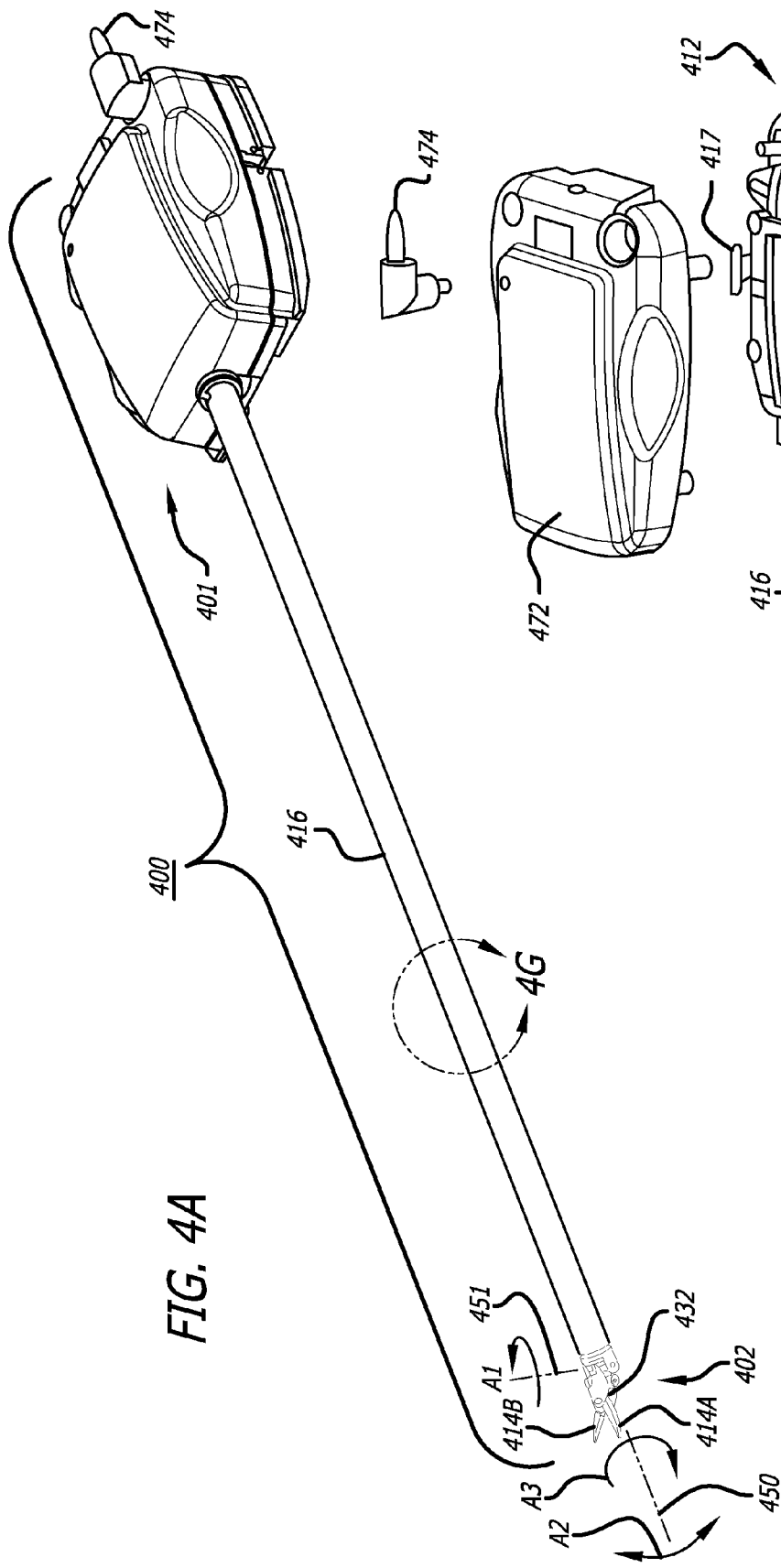
Figure 4B:
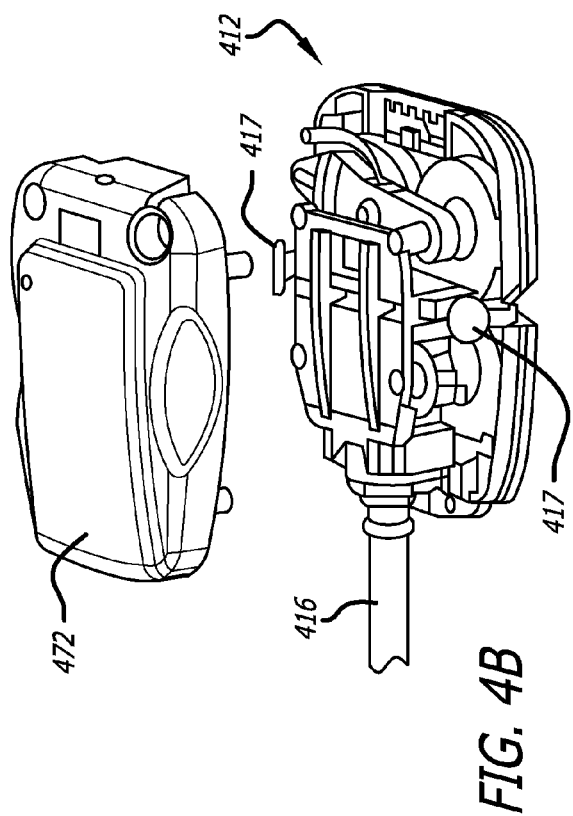

Referring now to FIGS. 2C, 2D, and 4B, the mounting of the robotic surgical tool 101A to an adapter 228 of the robotic surgical arm is now briefly described.

The robotic surgical arm 153 may include an adapter 228 to which the electro-surgical robotic tool 101A or other surgical tool 101 may be mounted. FIG. 2D illustrates a front side of an exemplary adapter 228. The front side of the adaptor 128 is generally referred to as a tool side 230 and the opposite side is generally referred to as a holder side (not shown).

FIG. 4B illustrates a back side of an exemplary electro-surgical robotic tool 400 as the surgical robotic tool 101A. The robotic surgical tool 400 includes an exemplary mountable housing 401 including an interface base 412 that can be coupled to the adapter 228. The interface base 412 and the adapter 228 may be electrically and mechanically coupled together to actuate the robotic surgical tool 400. Rotatably coupled to the interface base 412 are one or more rotatable receiving members 418, also referred to as input disks. Each of the one or more rotatable receiving members 418 includes a pair of pins 422A and 422B generally referred to as pins 422. Pin 422A is located closer to the center of each rotatable receive member 418 than pin 422B. The one or more rotatable receiving members 418 can mechanically couple respectively to one or more rotatable drivers 234 of the adapter 228. The robotic surgical tool 101A may further include release levers 416 to release it from the adapter 228.

The interface base 412 may further include one or more electrical contacts or pins 424 to electrically couple to electrical connector 242 of the adapter 228. The interface base 412 may further include a printed circuit board 425 and one or more integrated circuits 426 coupled thereto and to the one or more pins 424. The one or more integrated circuits 426 may be used to identify the type of robotic surgical tool coupled to the robotic arm, so that it may be properly controlled by the master control console 150.

The adapter 228 includes one or more rotatable drivers 234 rotatably coupled to a floating plate 236. The rotatable drivers 234 are resiliently mounted to the floating plate 236 by resilient radial members which extend into a circumferential indentation about the rotatable drivers. The rotatable drivers 234 can move axially relative to floating plate 236 by deflection of these resilient structures.

The floating plate 236 has a limited range of movement relative to the surrounding adaptor structure normal to the major surfaces of the adaptor. Axial movement of the floating plate helps decouple the rotatable drivers 234 from a robotic surgical tool 101 when its release levers 416 are actuated.

The one or more rotatable drivers 234 of the adapter 228 may mechanically couple to a part of the surgical tools 101. Each of the rotatable drivers 234 may include one or more openings 240 to receive protrusions or pins 422 of rotatable receiving members 418 of the robotic surgical tools 101. The openings 240 in the rotatable drivers 234 are configured to accurately align with the rotatable receiving elements 418 of the surgical tools 101.

The inner pins 422A and the outer pins 422B of the rotatable receiving elements 418 respectively align with the opening 240A and the opening 240B in each rotatable driver. The pins 422A and openings 240A are at differing distances from the axis of rotation than the pins 422B and openings 240B so as to ensure that rotatable drivers 234 and the rotatable receiving elements 418 are not aligned 180 degrees out of phase from their intended position. Additionally, each of the openings 240 in the rotatable drivers may be slightly radially elongated so as to fittingly receive the pins in the circumferential orientation. This allows the pins 422 to slide radially within the openings 240 and accommodate some axial misalignment between the tool and the adapter 228, while minimizing any angular misalignment and backlash between the rotatable drivers 234 and the rotatable receiving elements 418. Additionally, the interaction between pins 422 and openings 240 helps restrain the robotic surgical tool 101 in the engaged position with the adapter 228 until the release levers 416 along the sides of the housing 401 push on the floating plate 236 axially from the interface so as to release the tool 101.

When disposed in a first axial position (away from the tool side 230) the rotatable drivers are free to rotate without angular limitation. The one or more rotatable drivers 234 may rotate clockwise or counter-clockwise to further actuate the systems and tools of the robotic surgical instruments 101. However, as the rotatable drivers move axially toward the tool side 230, tabs (extending radially from the rotatable drivers) may laterally engage detents on the floating plates so as to limit the angular rotation of the rotatable drivers about their axes. This limited rotation can be used to help engage the rotatable drivers the rotating members of the tool as the pins 422 may push the rotatable bodies into the limited rotation position until the pins are aligned with (and slide into) the openings 140 in the rotatable drivers.

While rotatable drivers 234 are described here, other types of drivers or actuators may be provided in the adapter 228 to actuate systems or tools of the robotic surgical instruments 101. The adapter 228 further includes an electrical connector 242 to electrically couple to surgical instruments 101.

The mounting of robotic surgical tool 101A to the adapter 228 generally includes inserting the tip or distal end of the shaft or hollow tube of the robotic surgical tool through the cannula 219 and sliding the interface base 412 into engagement with the adapter 228, as illustrated in FIG. 2C. A lip 232 on the tool side 130 of the adaptor 128 slidably receives the laterally extending portions of the interface base 412 of the robotic surgical tool. A catch 244 of adapter 228 may latch onto the back end of the interface base 412 to hold the tool 101A in position. The protrusions or pins 422 extending from the one or more rotatable members 418 of the robotic surgical tool couple into the holes 240 in the rotatable drivers 234 of the adapter 228.

The range of motion of the rotatable receiving elements 418 in the robotic surgical tool may be limited. To complete the mechanical coupling between the rotatable drivers of the adapter and the rotatable receiving elements 418, the operator O at the surgical master control console 150 may turn the rotatable drivers in one direction from center, turn the rotatable drivers in a second direction opposite the first, and then return the rotatable drivers to center. Further, to ensure that the pins 422 enter openings 240 of adapter 228, the adapter 228 and tool 101A mounted thereto may be moved along the axis 215C. The adapter 228 and tool 101A mounted thereto may be moved to an initial position so that the tip or distal end of the shaft or hollow tube is disposed within the cannula 219.

To dismount and remove the robotic surgical tool 101A, the release levers 416 may be squeezed pushing out on the mountable housing 401 to release the pins 422 from the holes 240 and the catch 244 from the back end of the interface base. The mountable housing 401 is then pulled up to slide the interface base 412 up and out from the adapter 228. The mountable housing 401 is continually pulled up to remove the tip or distal end of the shaft or hollow tube out from the cannula 219. After the robotic surgical tool 101A is dismounted, another robotic surgical tool may be mounted in its place, including a new or freshly sterilized electro-surgical robotic tool 400.

As previously discussed, the robotic surgical tool 101A may include one or more integrated circuits 426 to identify the type of robotic surgical tool coupled to the robotic arm, such that it may be properly controlled by the master control console 150. However, the robotic surgical system may determine whether or not the robotic surgical tool is compatible or not, prior to its use.

The system verifies that the tool is of the type which may be used with the robotic surgical system 100. The one or more integrated circuits 426 may signal to the computer 151 in the master control console 150 data regarding compatibility and tool-type to determine compatibility as well as control information. One of the integrated circuits 426 may include a non-volatile memory to store and read out data regarding system compatibility, the tool-type and the control information. In an exemplary embodiment, the data read from the memory includes a character string indicating tool compatibility with the robotic surgical system 100. Additionally, the data from the tool memory will often include a tool-type to signal to the master control console how it is to be controlled. In some cases, the data will also include tool calibration information. The data may be provided in response to a request signal from the computer 151.

Tool-type data will generally indicate what kind of tool has been attached in a tool change operation. For example, the tool-type data might indicate that an electro-surgical robotic instrument 101A has been mounted to the robotic arm. The tool-type data may include information on wrist axis geometries, tool strengths, grip force, the range of motion of each joint, singularities in the joint motion space, the maximum force to be applied via the rotatable receiving elements 418, the tool transmission system characteristics including information regarding the coupling of rotatable receiving elements 418 to actuation or articulation of a system within the robotic surgical instrument.

Instead of storing all of the tool-type date in the one or more integrated circuits 426, most of the tool-type data may optionally be stored in memory or a hard drive of the computer 151 in the robotic surgical system 100. An identifier may be stored in the one or more integrated circuits 426 to signal the computer 151 to read the relevant portions of data in a look up table store in the memory or the hard drive of the computer. The tool-type data in the look-up table may be loaded into a memory of computer 151 by the manufacturer of the robotic surgical system 100. The look-up table may be stored in a flash memory, EEPROM, or other type of non-volatile memory. As a new tool-type is provided, the manufacturer can revise the look-up table to accommodate the new tool-specific information. It should be recognized that the use of tools which are not compatible with the robotic surgery system, for example, which do not have the appropriate tool-type data in an information table, could result in inadequate robotic control over robotic surgical tool by the computer 151 and the operator O.

In addition to the tool-type data, tool specific information may be stored in the integrated circuit 426, such as for reconfiguring the programming of computer 151 to control the tool. There may be calibration information, such an offset, to correct a misalignment in the robotic surgical tool. The calibration information may be factored into the overall control of the robotic surgical tool. The storing of such calibration information can be used to overcome minor mechanical inconsistencies between tools of a single type. For example, the tool-type data including the tool-specific data may be used to generate appropriate coordinate transformations and servo drive signals to manipulate the robotic arm and rotate the rotatable drivers 234. In this case, the integrated circuit 426 includes the information to set up the control system to drive the end effectors in the tool to have a maximum joint torque setting so that the jaws of a robotic gripping tool or a robotic electrosurgical tool can clamp to tissue with a maximum force.

Additionally, some robotic surgical tools have a limited life span. Tool life and cumulative tool use information may also be stored on the tool memory and used by the computer to determine if the tool is still safe for use. Total tool life may be measured by clock time, by procedure, by the number of times the tool has been loaded onto a holder, and in other ways specific to the type of tool. Tool life data is preferably stored in the memory of the tool using an irreversible writing process.

Figure 3A:
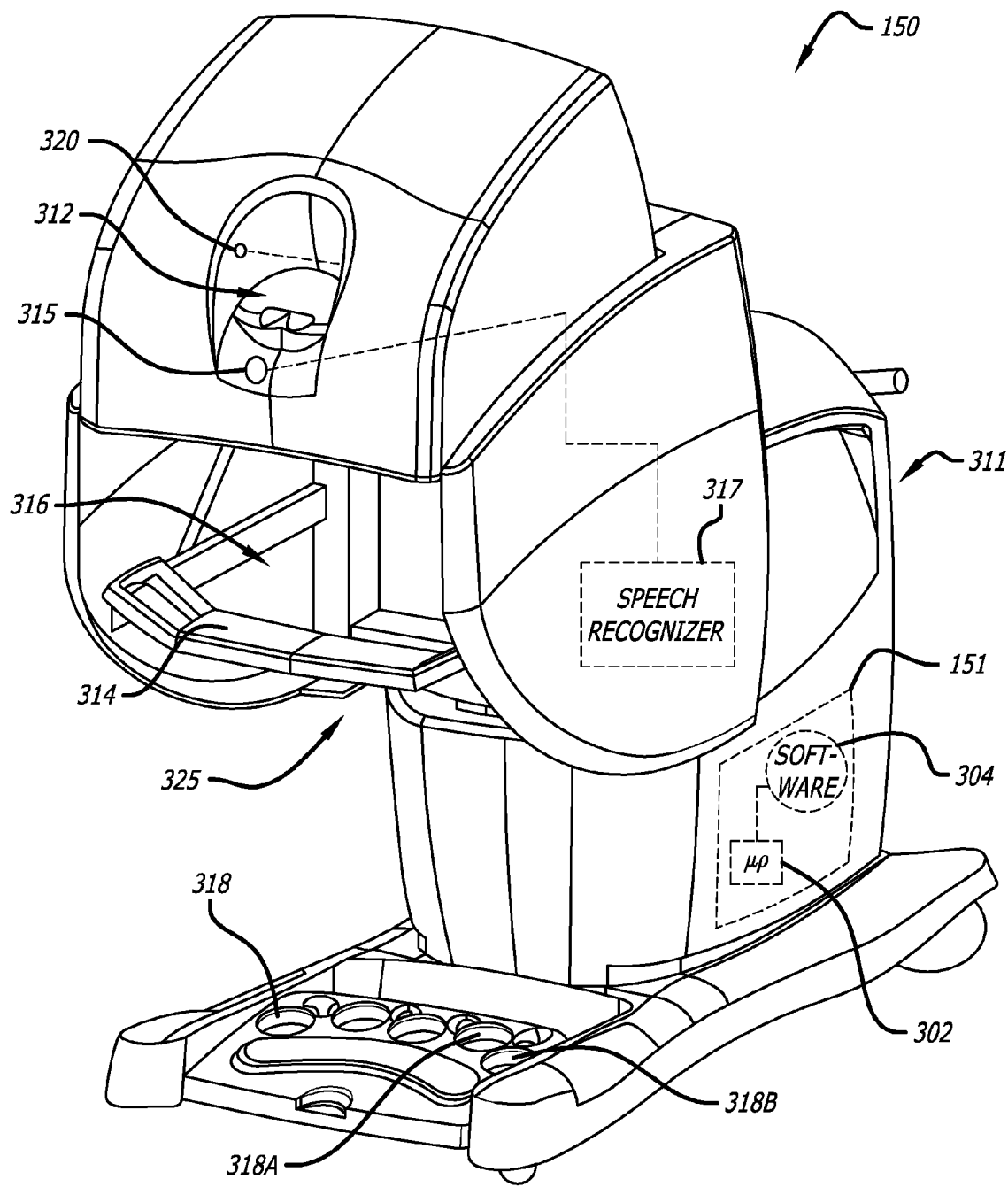
FIG. 3A is a perspective view of a robotic surgical master control console.

Referring now to FIG. 3A, a perspective view of a robotic surgical master control console 150 is illustrated. The master control console 150 of the robotic surgical system 100 includes the computer 151, a binocular viewer 312, an arm support 314, a microphone 315, a pair of control input wrists and control input arms in a workspace 316, a speech recognizer 317, foot pedals 318 (including foot pedals 318A-318B), and a viewing sensor 320.

The computer 151 may include one or microprocessors 302 to execute instructions and a storage device 304 to store software with executable instructions that may be used to generate control signals to control the robotic surgical system 100. The master control console 150 generates the control signals to control the electro-surgical robotic instruments in a surgical site.

The viewer 312 has at least one display where images of a surgical site may be viewed to perform minimally invasive surgery.

The arm support 314 can be used to rest the elbows or forearms of the operator O (typically a surgeon) while gripping touch sensitive handles 325 (see FIGS. 3B-3C), one in each hand, of the pair of control input wrists 352 in the workspace 316 to generate control signals. The touch sensitive handles 325 are positioned in the workspace 316 disposed beyond the arm support 314 and below the viewer 312.

When using the master control console, the operator O typically sits in a chair, moves his or her head into alignment with the binocular viewer 312, and grips the touch sensitive handles 325 of the control input wrists 352, one in each hand, while resting their forearms against the arm support 314. This allows the touch sensitive handles to be moved easily in the control space 316 in both position and orientation to generate control signals.

Additionally, the operator O can use his feet to control the foot-pedals to change the configuration of the surgical system and generate additional control signals to control robotic surgical instruments.

To ensure that the operator is viewing the surgical site when controlling the robotic surgical tools 101, the master control console 150 may include the viewing sensor 320 disposed adjacent the binocular display 312. When the system operator aligns his or her eyes with the binocular eye pieces of the display 312 to view a stereoscopic image of the surgical worksite, the operator's head sets off the viewing sensor 320 to enable the control of the robotic surgical tools 101. When the operator's head is removed the area of the display 312, the viewing sensor 320 can disable or stop generating new control signals in response to movements of the touch sensitive handles in order to hold the state of the robotic surgical tools.

The computer 151 with its microprocessors 302 interprets movements and actuation of the touch sensitive handles 325 (and other inputs from the operator O or other personnel) to generate control signals to control the robotic surgical instruments 101 in the surgical worksite. In one embodiment of the invention, the computer 151 and the viewer 312 map the surgical worksite into the controller workspace 316 so it feels and appears to the operator that the touch sensitive handles 325 are working over surgical worksite.

Referring now to FIG. 3B, a perspective view of a control input wrist 352 with a touch sensitive handle 325 is illustrated. The control input wrist 352 is a gimbaled device that pivotally supports the touch sensitive handle 325 of the master control console 150 to generate control signals that are used to control the robotic surgical manipulator 152 and the robotic surgical tools 101, including electro-surgical robotic tool 101A, 101C. A pair of control input wrists 352 are supported by a pair of control input arms in the workspace 316 of the master control console 150.

The control input wrist 352 includes first, second, and third gimbal members 362, 364, and 366. The third gimbal member is rotationally mounted to a control input arm (not shown).

The touch sensitive handle 325 includes a tubular support structure 351, a first grip 350A, and a second grip 350B. The first grip and the second grip are supported at one end by the structure 351. The touch sensitive handle 325 can be rotated about axis G illustrated in FIGS. 3B-3C. The grips 350A, 350B can be squeezed or pinched together about the tubular structure 351. The "pinching" or grasping degree of freedom in the grips is indicated by arrows Ha,Hb in FIG. 3B and arrows H in FIG. 3C.

The touch sensitive handle 325 is rotatably supported by the first gimbal member 362 by means of a rotational joint 356g. The first gimbal member 362 is in turn, rotatably supported by the second gimbal member 364 by means of the rotational joint 356f. Similarly, the second gimbal member 364 is rotatably supported by the third gimbal member 366 using a rotational joint 356d. In this manner, the control wrist allows the touch sensitive handle 325 to be moved and oriented in the workspace 316 using three degrees of freedom.

The movements in the gimbals of the control wrist 352 to reorient the touch sensitive handle in space can be translated into control signals to control the robotic surgical manipulator 152 and the robotic surgical tools 101.

The movements in the grips 350A, 350B of the touch sensitive handle 325 can also be translated into control signals to control the robotic surgical manipulator 152 and the robotic surgical tools 101. In particular, the squeezing motion of the master grips 350A, 350B over their freedom of movement indicated by arrows Ha, Hb or H, may be used to control the end effectors of the robotic surgical tools.

To sense the movements in the touch sensitive handle 325 and generate controls signals, sensors can be mounted in the handle 325 as well as the gimbal member 362 of the control input wrist 352. Exemplary sensors may be a Hall effect transducer, a potentiometer, an encoder, or the like.

Figure 3C:
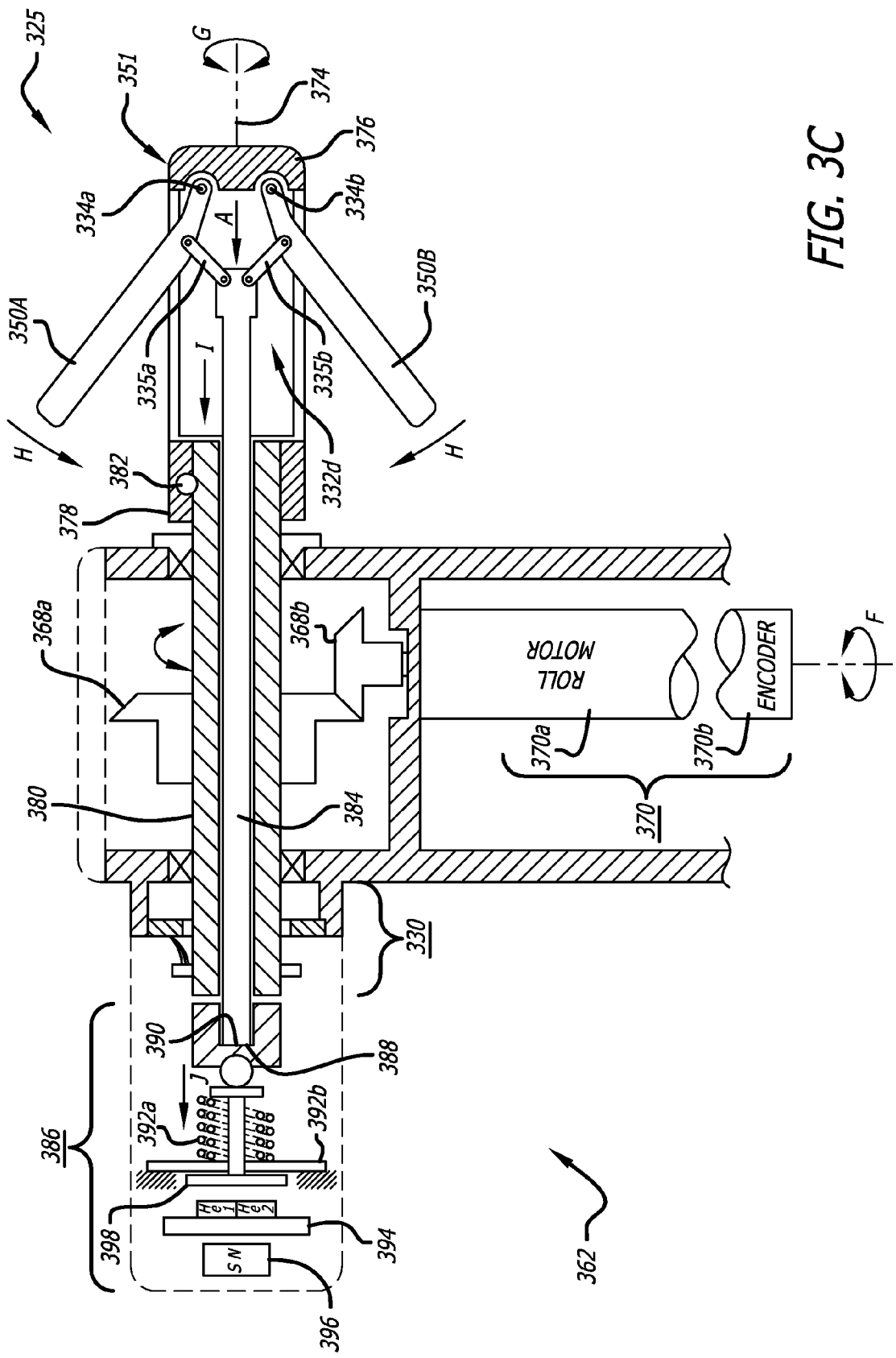
FIG. 3C is a cross-sectional view schematically illustrating mounting of the touch sensitive handle of FIG. 3B with sensors to sense gripping and rotation of the handle to control robotic surgical tools, including a robotic electro-surgical tool.

Referring now to FIG. 3C, a cross-sectional view of the touch sensitive handle 325 and gimbal member 362 of the control input wrist 352 is illustrated. FIG. 3C provides an example as to how the touch sensitive handle 325 can be mounted to the control input wrist 352 to sense the gripping and rotation of the handle to control robotic surgical tools 101.

As illustrated in FIG. 3C, the exemplary gimbal member 362 includes beveled gears 368a, 368b which can couple the rotational motion of the touch sensitive handle 325 to a roll sensor 370. The roll sensor 370 may use a potentiometer or encoder 370b included in a roll motor 370a to sense the rotation. Alternatively, a separate roll sensor, such as a potentiometer, may be directly coupled to the shaft 380 to sense the rotation of the touch sensitive handle. In any case, a roll sensor senses the roll motion of the touch sensitive handle 325 and generates control signals in response thereto to control the robotic surgical tools 101.

To sense a squeezing motion in the grips 350A,350B of the touch sensitive handle 325, a remote sensing assembly 386 may be included by the gimbal member 362. The first and second grips 350A,350B are adapted to be squeezed together by a hand of an operator O so as to define a variable grip separation. The grip separation may be determined as a function of a variable grip angle with an axis or as a function of a variable grip separation distance, or the like. Alternative handle actuations, such as movement of a thumbwheel or knob may also be provided in the handle to control the robotic surgical instruments 101.

In the exemplary embodiment, the remote sensor assembly 386 includes a circuit board 394 on which a first and a second Hall effect sensors, HE1, HE2 are mounted. A magnet 396 is disposed distally beyond the circuit board 394 and the Hall effect sensors. A magnetic mass 398 is axially coupled to the proximally oriented surface 390 of a push rod 84. Thus, the magnetic mass 398 moves (as shown by Arrow J) with the push rod 384 and varies the magnetic field at the Hall effect sensors in response actuation of the grips 350A,350B.

To translate the squeezing action of the grips 350A,350B to the sensor 386, the gimbal member 362 includes a push rod 384 within the tubular handle structure 351. Each of the grips 350A, 350B pivot about a respective pivot 334a, 334b in the tubular handle structure 351. Urging links 335a, 335b respectively couple between the grips 350A,350B and a first end of the push rod 384. The squeezing action of the grips 350A, 350B is translated into a linear motion on the push rod 384 by means of urging links 335a,335b as shown by arrow A in FIG. 3C. A second end of the push rod 384 couples to the sensor 386. As discussed previously, the magnetic mass 398 is axially coupled to the surface 390 of the push rod 384 in order to sense the linear motion in the push rod and the squeezing motion of the grips 350A,350B.

A biasing mechanism such as spring 392 applies a force against the squeezing motion of the grips to return them to full open when the grips are released. The biasing spring 392 may be a linear or non-linear elastic device biasing against the depression of grips 350A, 350B, e.g., a single or multiple element assembly including springs or other elastic members. For example, spring 392 may comprise a concentric dual spring assembly whereby one spring provides a "softer" bias response as the grips 350A, 350B are initially depressed, and a second spring provides a superimposed "firm" bias response as the grips 350A, 350B approach a fully depressed state. Such a non-linear bias may provide a pseudo force-feedback to the operator.

It should be noted that a wide variety of alternative sensing arrangements may be used to translate the mechanical actuation of the touch sensitive handle and control input wrist into control signals. While Hall effect sensors are included in the exemplary embodiment, alternative embodiments may include encoders, potentiometers, or a variety of alternative optical, electrical, magnetic, or other sensing structures.

Electro Surgical Instruments

Exemplary embodiments of robotic electro surgical tools that can be mounted to a robotic arm in a robotic surgical system are now described. However, further details of robotic electro-surgical tools may be described in U.S. Pat. Nos. with filing dates and named inventor as follows U.S. Pat. No. 6,840,938, Dec. 21, 2001, Morley et al.; and U.S. Pat. No. 6,994,708, Apr. 18, 2002, Scott Manzo; and application Ser. No. 10/726,795, Dec. 2, 2003, Cooper et al.; Ser. No. 10/611,411, Jun. 30, 2003, Manzo et al.; Ser. No. 11/238,698, Sep. 28, 2005, Manzo et al.; and Ser. No. 11/238,794, Sep. 28, 2005, Scott Manzo, all of which are incorporated herein by reference.

Robotic surgical instruments 101 mounted on the robotic surgical arms 153 typically include elongated shafts, with proximal and distal ends. End effectors are generally mounted on wrist-like mechanisms pivotally mounted on the distal ends of the shafts, for enabling the instruments 101 to perform one or more surgical tasks. Generally, the elongate shafts of surgical instruments 101 allow the end effectors to be inserted through entry ports in a patient's body so as to access the internal surgical site. Movement of the end effectors is generally controlled via master controls on the master console 150.

Electrosurgical instruments and systems, as well as methods of performing minimally invasive robotic surgical procedures with such instruments are now disclosed. The instruments of the embodiments of the invention are capable of treating tissue with heat produced by electrical energy while cutting, shearing, grasping, engaging, or contacting treatment tissue. Electrosurgical instruments may apply a high-frequency alternating current to surrounding tissue, thereby to cause the tissue temperature to rise to the point where the tissue is cut or coagulates. Alternatively, electrosurgical instruments may apply heat to tissue by means of electrically generated heat inside the instrument. The electrosurgical treatment may further reduce bleeding of tissue by cauterizing tissue and coagulating blood, or achieve various other desired effects on the treatment tissue such as sealing tissue together. The electrosurgical treatment is carried out in a safe and effective manner that incorporates a variety of safety features to prevent current leakage to non-target tissue so as to reduce collateral tissue damage, unwanted burning, or the like. The fact that a cauterizing action is provided and the nature thereof should not be understood as limiting to the embodiments of the present invention.

Referring to FIGS. 4A-4E, a robotic electro-surgical tool or instrument 400 is illustrated in greater detail than that of instruments 101A and 101C. The robotic electro-surgical tool or instrument 400 includes a mountable housing 401, an elongated shaft 416 having a proximal end and a distal end; and end effectors 414A-414B (collectively referred to by 414) coupled near the distal end of the shaft 416. The mountable housing 401 includes an interface or tool base 412 coupled to the proximal end of the shaft 416. The mountable housing 401 may further include one or more electrical connectors 474, 474A-474B, a cover 472, and one or more release levers 417. At the distal end of the shaft 416 is a mechanical wrist 402 to move the end effectors 414.

The interface or tool base 412 can couple to the adapter 228 to which other surgical tools may also couple so that the electrosurgical tool 400 is removably connectable to the robotic surgical system. During surgery, the adapter 228 is coupled to the moveable carriage 237. Thus, with the electrosurgical tool 400 mounted to the adapter 228, it can translate with the carriage 237 along the actuating portion of the robotic surgical arm 153.

When mounted to a robotic surgical arm 153, end effectors 414 may have a plurality of degrees of freedom of movement relative to arm 153, in addition to actuation movement of the end effectors. As discussed previously, the electrosurgical tool 400 may be translated along an insertion axis as indicated by arrow 257 in FIG. 2A. The elongated shaft 416 is rotatably mounted to the base 412 for rotation about an axis 450 extending longitudinally along the shaft 450 as indicated by the rotational arrow A3. The wrist 402 may be a single pivot wrist, a multi-pivot wrist, a distal roll joint mechanism, or other joints or wrist-like mechanism to provide additional operational degrees of freedom to the end effector. The wrist 402 may pivot around an axis 451 at a pivot point as indicated by the rotational arrow A1. The end effectors 414A,414B may pivot together as a whole about pivot point 432 as indicated by arrow A2.

The orientation of the mechanical wrist 402 is controlled through pulleys in the tool base 412 and the wrist 402 with cables of cable loops wrapped around each being routed through the shaft 416. The robotic system causes the pulleys in the tool base 412 to be rotated in order to control the position of the mechanical wrist 402, and the end effectors 414. Thus, the cable of the cable loops may also be referred to as a control cable. That is, the end effectors 414 are actuated from the tool base 412 through a cable loop, pulleys, and a spool similar to how other elements of the wrist 402 are controlled. In this case, two cable loops are used to actuate the end effectors 414, one cable loop for each.

Further details of mechanical wrists that may be applicable to the mechanical wrist 402 are described in U.S. Pat. Nos. with filing dates and named inventor as follows U.S. Pat. No. 5,792,135, May 16, 1997, Madhani et al; U.S. Pat. No. 5,979,900, May 16, 1997, Madhani et al; U.S. Pat. No. 5,807,377, May 16, 1997, Madhani et al; U.S. Pat. No. 6,206,903, Oct. 8, 1999, Ramans; U.S. Pat. No. 6,312,435, Oct. 8, 1999, Wallace et al.; U.S. Pat. No. 6,371,952, Jun. 28, 1999, Madhani et al; U.S. Pat. No. 6,394,998, Sep. 17, 1999, Wallace et al.; U.S. Pat. No. 6,676,684, Sep. 4, 2001, Morley et al.; U.S. Pat. No. 6,685,698, Jan. 10, 2003, Morley et al.; U.S. Pat. No. 6,699,235, Mar. 2, 2004, Wallace et al.; U.S. Pat. No. 6,746,443, Jul. 27, 2000, Morley et al.; and U.S. Pat. No. 6,817,974, Jun. 28, 2002, Cooper et al., all of which are incorporated herein by reference.

The end effectors 414 are used in performing a surgical operation such as cutting, shearing, grasping, engaging, or contacting tissue adjacent a surgical site. In one embodiment of the invention, the end effectors 414 includes a pair of gripping jaws for clamping onto tissue. Additionally, a conductor electrically communicates with at least one of the end effectors to deliver electrical energy to tissue clamped by the gripping jaws.

As shown in FIG. 4B, the tool base 412 may be enclosed by a cover 472 which mounts an electrical connector 474. A conductor 448 is electrically coupled to the electrical connector 474 at one end and at least one end effector at the opposite end.

Figure 4C:
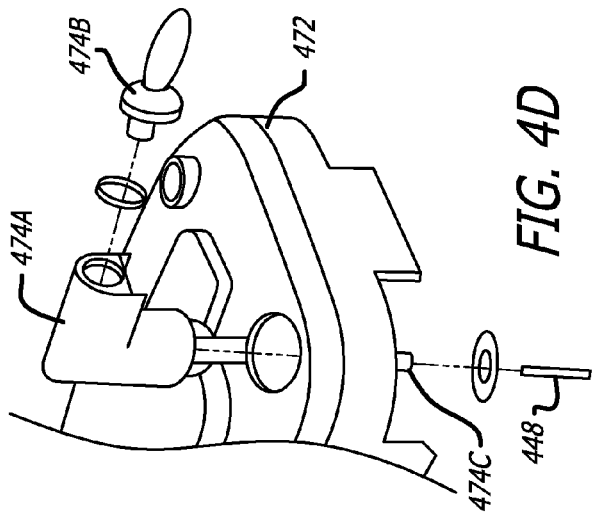

Referring now to FIG. 4C, an insulated conductor 448 passes out from the shaft 416 to the rear of base 412 to the electrical connector 474 for connection to the monopolar electrosurgical generator. The conductor 448 communicates with at least one of the end effectors, to deliver electrical energy to tissue from an electrosurgical generator G, such as the monopolar generator 102B illustrated in FIG. 1. The tool base 412 may further support a bipolar generator 102A by adding an extra wire connection to the connector 474 or by adding an extra electrical connector 474 and routing two wires to each of the two end effectors.

As discussed previously, the end effectors 414 are actuated from the tool base 412 through a cable of a cable loop, pulleys, and an actuating spool. A cable loop CL may be considered to be a single cable routed in a loop around the drive pulley from the spool in the tool base. A cable loop may be formed by joining or splicing different segments of cable together. Each side of the cable loop CL may be referred to as being a cable. In order to prevent slippage, a cable may be fixed to a pulley, shaft, capstan and/or tube at one point by soldering, welding, crimping or other mechanical fixing means.

The tool base 412 includes actuating spools 434A-434C, guide pulleys 435A-435B, and cable loops CL 436A-436C to form driven elements control the mechanical wrist 402 and the end effectors 414. The details of a driven element are discussed further below with reference to FIG. 12B. Each of the driven elements includes receiving elements or input disks (not visible in FIG. 4C) that releasably couple through an adapter to a rotatable driving element that is mounted on the carriage 237 of the robotic arm assembly 153. The rotatable driving elements of the carriage 237 are generally coupled to actuators (not shown), such as electric motors or the like, to cause selective angular displacement of each in the carriage 237. Selective actuation of the actuators is transmitted through the rotatable driving element on the carriage 137, to the input disks of the tool 400 and cause selective angular displacement of the actuating spools 434A-434C. This is described in greater detail below with reference to FIGS. 8-12B. Where more or fewer degrees of freedom are desired, the number of spools may be decreased or increased.

Figure 4D:
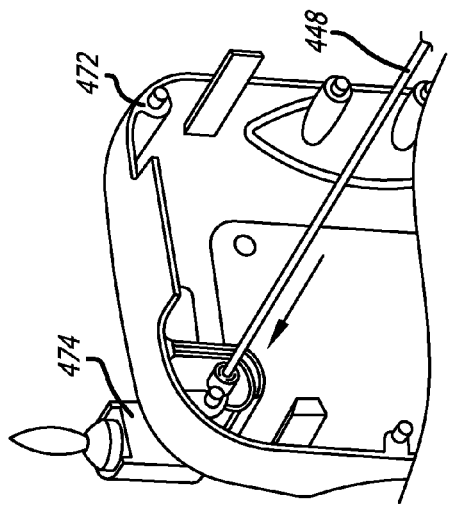
Figure 4E:
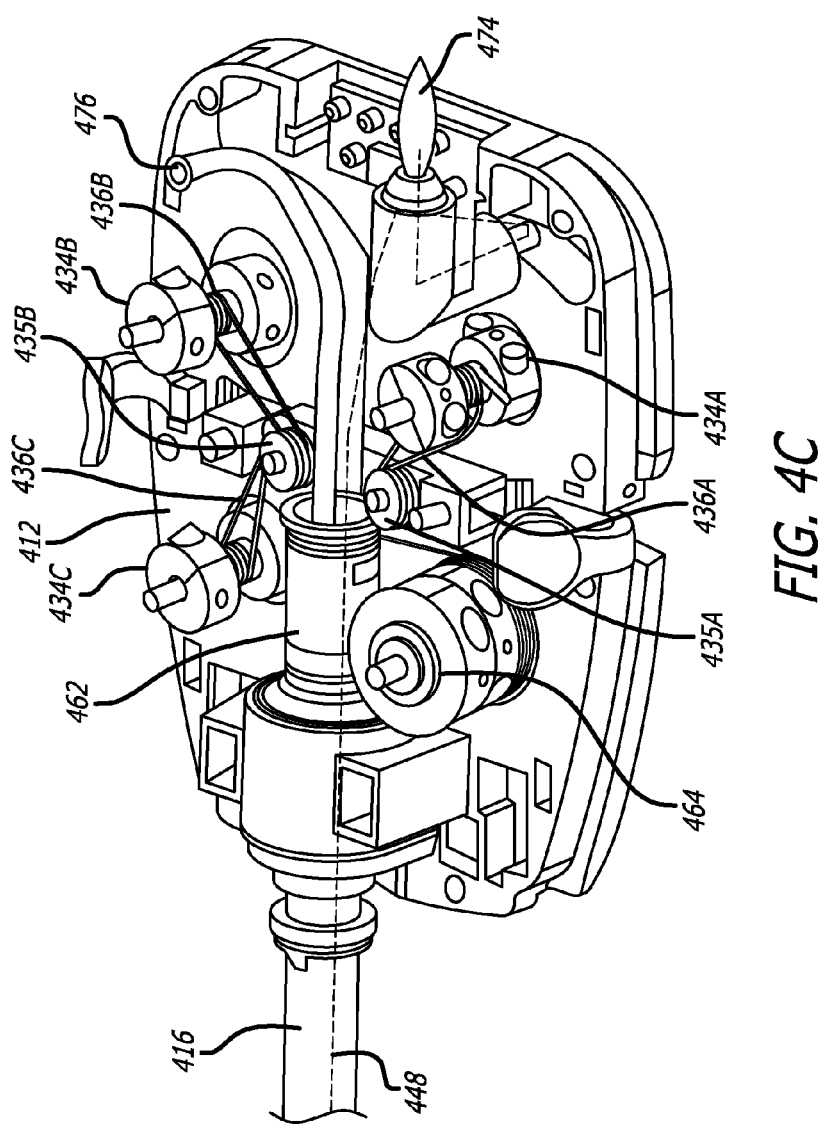
Figure 4G:
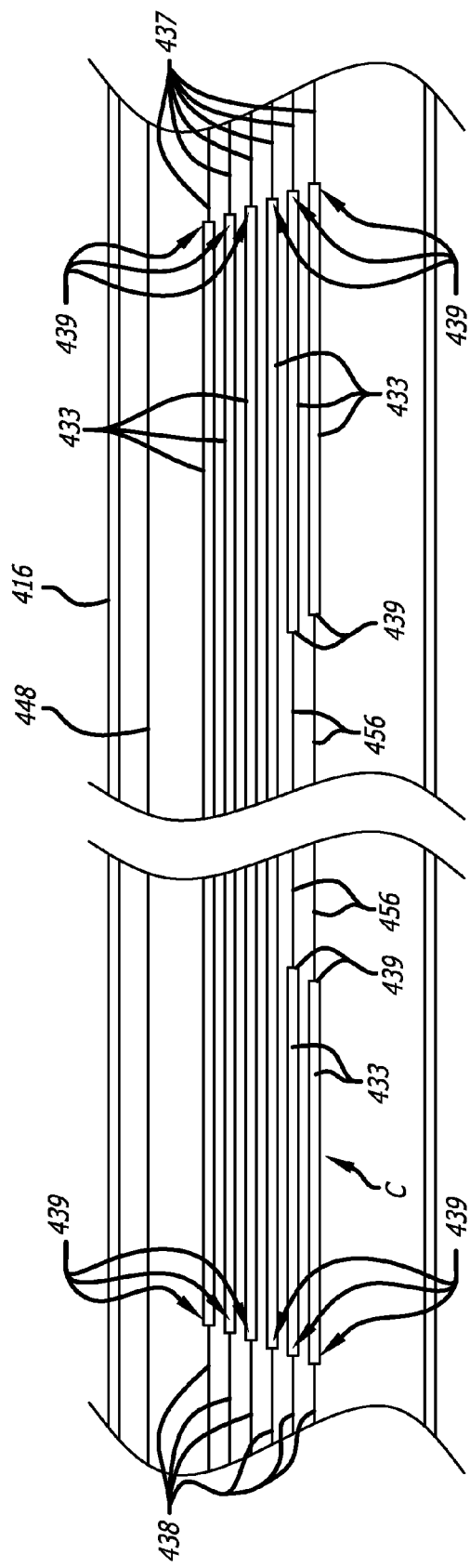

Referring now to FIG. 4G, to inhibit stretching of the cables C along their lengths and along the shaft 416, elongate relatively rigid members, e.g., hypotube portions 33, may be used. The hypotube portions 433 couple to opposed Tungsten cable portions 437, 438 at each end. Ends of the Tungsten cable portions 437, 438 are typically crimped into opposing ends of the hypotubes as indicated by crimps 439. The hypotubes 433 are typically hollow tubes having a circular cross-section. One or more of the cables C may also include a non-conductive portion or an insulator portion 456 coupled between hypotube portions. This may be particularly useful for robotic electro-surgical tools and a live end effector in isolating the current and voltages applied to tissue from other parts of the instrument and system. Regardless of the use of hypotube portions 433 and insulative portions 456, the cabling, hypotube, and insulative portions may be referred to as cables C of a cable loop CL. Note that the cables C, at least in the region of the wrist, are typically made of metal, such as Tungsten or stainless steel, to provide sufficient strength, bendability and durability.

The cables of the cable loops 436A-434C are routed from the actuating spools over the guide pulleys 435A-435B and through the shaft 416 to drive pulleys in the wrist 402. The tool base 412 further includes a spool 464 and a drum 462 with a cable loop coupled there-between to control the rotation of the shaft 416 and the wrist 402.

A first end of the cable of each cable loop is wrapped in one direction around the spool with the second end of the cable wrapped in an opposite direction around the same spool. In this manner, one end of cable is taken up while the other end of the cable is released during the rotation of a spool. Each spool includes a tension mechanism to avoid slack in the cable of each cable loop.

The shaft of each spool extends through the tool base 412 to its underside to couple to an engaging member. The engaging member can releasably couple to a complimentary engaging member that is in turn coupled to an actuator of the surgical system, such as an electric motor, to cause an angular displacement in the spool in response to a control signal from the control console.

An optional flush tube 476 may be mounted to a tool base cover 472 by a flush port 478 and the assembled base 412. The flush tube preferably extends forward (distally) within the base 412 to communicate with the shaft 416 to permit fluids to be passed through the shaft 416 and/or to pressurize the shaft 416. For example, introduction of insufflation gas during surgery or the introduction of cleaning or sterilization gases or fluids prior and/or subsequent to surgery may be passed to the shaft 416 via flush tube 476. U.S. Pat. No. 6,004,509 describes the use of fluids and gases to maintain sterility of a surgical instrument, and is incorporated herein by reference.

Referring now to FIGS. 4D and 4E, the base cover 472 mounts an electrical connector 474, in this case, a banana clip assembly 474a, 474b, and 474c, for the insulated conductor 448 to permit connection to an electrosurgical generator. Note that the connections described above provide an insulated continuous electrical path from the base connector 474 to the end effectors 414A-414B protected from tissue contact except at the jaw portions thereof. Energization of one or both of the end effectors 414A-414B is controllable by the surgeon.

FIG. 4F illustrates a back side view of a portion of the robotic surgical tool 400, some elements of which were previously discussed. In particular, the interface base 412 is illustrated with rotatable receiving elements ("input disks") 418 rotatably coupled thereto. The interface base 412 is used to mount the instrument 400 to a robotic arm of a surgical robotic manipulator. The interface base 412 both mechanically and electrically couples the surgical instrument 400 to a robotic arm of the surgical robotic manipulator 152. The release levers 416 are located at the sides of the mountable housing and may be used to release the robotic surgical instrument 400 from a robotic arm.

The rotatable receiving elements 418 provide a mechanical coupling to the rotatable drivers 234 and drive motors mounted in the robotic surgical arm 153 and the robotic surgical manipulator 152. Each of the rotatable receiving elements 418 includes a pair of pins 422 extending from a surface thereof. An inner pin 422A is closer to an axis of rotation of each rotatable receiving elements 418 than an outer pin 422B, which helps to ensure positive angular alignment of the rotatable receiving elements 418. In one embodiment of the invention, the rotatable receiving elements 418 are disk shaped and are also referred to herein as "input disks".

The interface base 412 further includes an array of electrical connecting pins 424 and one or more integrated circuits 426 coupled to a printed circuit board 425 within the mountable housing 401. As the interface base 412 is backward compatible to the adapter 228, it maybe mechanically actuated by pre-existing driver motors found in the robotic surgical manipulator 152. While the interface base 412 has been described herein with reference to mechanical and electrical coupling elements, it should be understood that other modalities maybe used, including infrared coupling, magnetic coupling, inductive coupling, or the like.

Figure 9:
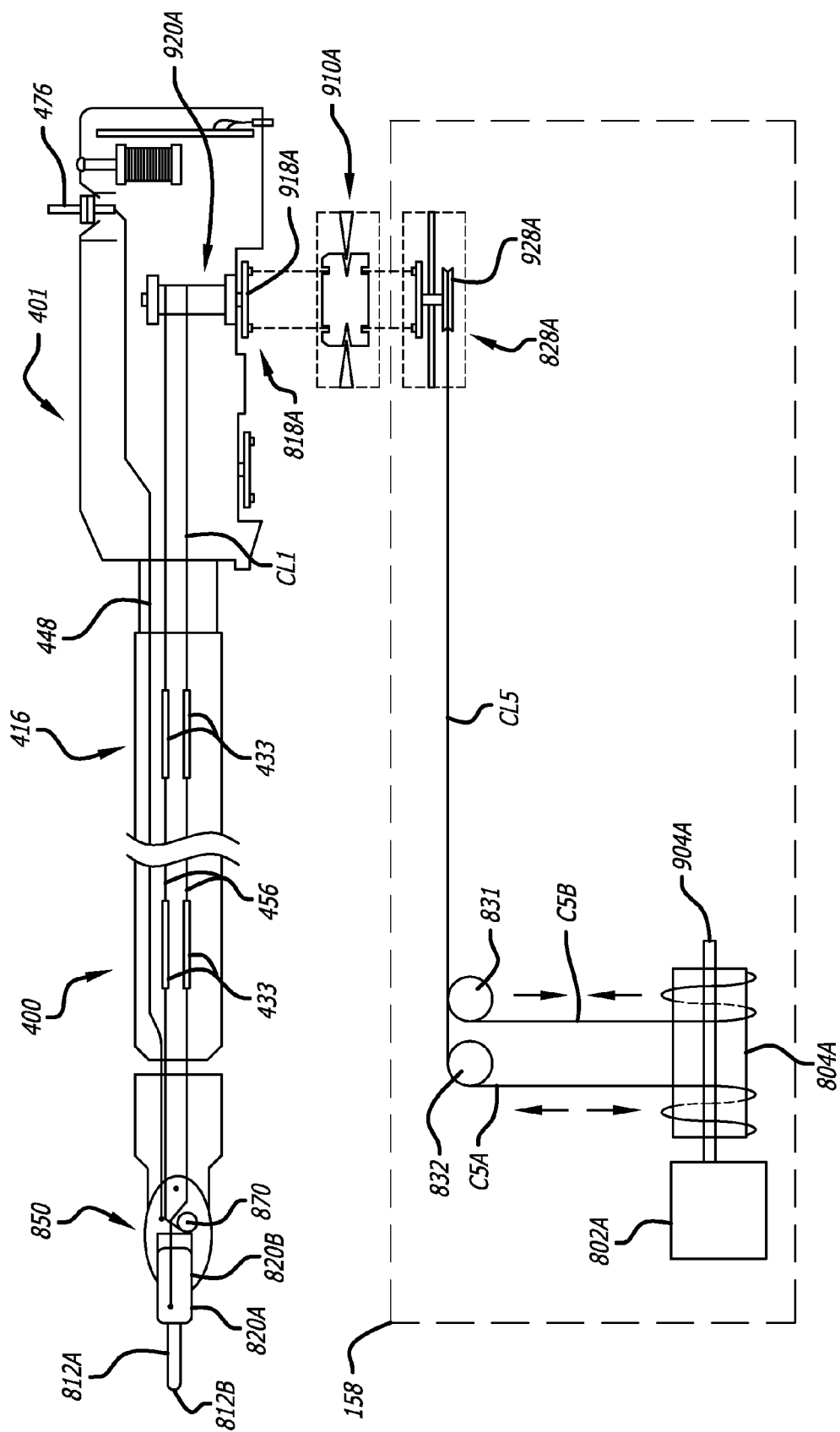

Referring momentarily now to FIG. 9, a schematic view of the electrocautery surgical instrument 400 is illustrated. The electrocautery instrument 400 may be used to generate an electrical current at a surgical site so as to burn or seal, e.g., ruptured blood vessels.

In a monopolar electrosurgical system, the patient is earthed and a voltage is supplied to the electrode coupled to the end effector. An electrically conductive cable 448 extends from a plug 474 on the housing 401 to the electrode at the end effector 812A, 812B. This conductive cable, or cautery wire, may include a "service loop" around a joint axis at the wrist. The service loop, a single loose wrap around the joint, permits rotation of the cautery blade about the axis without placing undue stress or stretch on the wire during such rotation. It will be appreciated that, in use, the plug 474 is releasably connected to an appropriate electrical source. The plug 474 is typically a conventional banana-type plug. The housing 401 is typically of a non-conductive plastics material.

It has been found that it is best to insulate the electrode at the end effectors from the rest of the instrument 400 so as to inhibit current leakage from the electrode to other elements in the instrument 400. It will be appreciated that should the distance between the electrode and the patient be relatively great when a voltage is applied, current may jump from the electrode to other conductive parts of the instrument. In such a case, current can be passed from the instrument 400 to the patient along a path of least resistance, e.g., at the entry port of the shaft coincident with its center of rotation. This may cause unnecessary burning at the entry port. Furthermore, the current may be passed along the instrument 400 to the telesurgical system in general and may be damaging to sensitive electronics, e.g., forming part of the endoscope and viewer arrangement.

Accordingly, the wrist mechanism 402,850 wherever possible is made of non conductive material. The wrist member 402,850 and the various pulleys are typically made from non-conductive plastic, e.g., polyethermide or ULTEM. Alternatively, a conductive wrist can be sheathed in a non-conductive material.

The conductive cable 448 is typically sheathed in an insulative material such as, e.g., polytetrafluoroethylene or TEFLON. The conductive cable is electrically coupled the electrode at the end effector 812A,812B. The electrode may be removably mountable on the end effector 812A,812B. Accordingly, a conductive seat or sleeve may be used to provide an electrical connection to the electrode when in a mounted condition.

The shaft 416 is typically made entirely from a nonconductive material, or at least sheathed in such a material, to insulate the shaft from the patient, in particular in the region of the port of entry coincident with the center of rotation. One nonconductive material for the shaft comprises an electrical grade fiberglass/vinyl ester composite material. Alternatively, a shaft of stainless steel or carbon fiber may be coated with, e.g., a nylon or parylene, such as Nylon-11 or Parylene C.

The cables that extend internally along the shaft 416 typically have non-conductive portions 456. Such non-conductive or insulative portions are typically high strength polymer cables in the form of, e.g., a liquid crystal polymer (LCP) such as VECTRAN, a liquid crystal polyester. The VECTRAN portions are typically crimped to opposed hypotube lengths. Opposed ends of such hypotubes are in turn typically crimped to tungsten cable lengths which extend to the spools in the housing 401 and to the wrist mechanism 850, respectively.

It will be appreciated that a number of other elements of the tool may also be formed of an insulative material. For example, the pulley arrangement 820,820B and the wrist member 850 coupled to the distal end of the shaft 416 may be formed of an insulative material such as, e.g., ULTEM.

Electro-Surgical End Effectors

Referring now to FIGS. 5A-5B, 6A-6B, and 7A-7B, exemplary cauterizing end effectors are illustrated. U.S. Pat. No. 6,840,938, filed by Morely et al. on Dec. 21, 2001 which has been incorporated by reference illustrates additional embodiments of cauterizing end effectors or electro-surgical end effectors.

FIGS. 5A-5B, illustrate a portion of an exemplary bipolar cauterizing tool 528. A wrist 574 is rotatably coupled to shaft 562 about the first axis A1. End effectors 578, 580 are rotatably coupled to the wrist 574 about a second axis A2. Both the end effectors and the wrist can rotate together about the longitudinal axis A3 of the shaft 562. A negative and positive electrode 582A, 582B (shown most clearly in FIGS. 6A and 6B) can be coupled to the end effectors to deliver a high frequency electrical energy into tissue engaged by the jaws 578, 580.

The conductive electrodes 582A, 582B can be coupled to an electric power supply (see the bipolar generator 102A illustrated in FIG. 1) through conductive leads 584A, 584B. In an exemplary embodiment, the conductive leads can be run from the tool base end of the instrument, through the shaft 562, through lumens in wrist 574, and up to the electrodes 582A, 582B disposed on the end effectors 578, 580. The distal portion of the conductive leads 584A, 584B can be run outside of the wrist 574 so as to allow for easy connection and disconnection of the conductive leads 584A, 584B from the electrodes.

Depending on the specific configuration of the cauterizer, the end effectors 578, 580 and drive system can be composed of a nonconductive material or a conductive material. In some embodiments, the electrodes can be insulated from the end effector with either a nonconductive bushing or sleeve that is composed of plastic, ceramic, TEFLON, ULTEM, or other non-conductive materials. If the electrodes are attached directly to the end effectors, an insulating bushing can be disposed between the conductive end effectors and the electrodes so that the only "live" portion of the surgical instrument are the electrodes.

The electrodes of the present invention are preferably made of a conductive material such as aluminum, stainless steel, platinum, tungsten, gold, or the like. The electrodes can be in the form of strips, deposited material, inserts, or the like. In some embodiments, the jaws themselves can be the electrodes.

For the bipolar methods of the present invention, the two electrodes on the end effectors should be at two electrical potentials and should not come in contact with each other. Thus, in most embodiments the electrodes are configured to have a gap between the electrodes even when the end effectors are in the closed configuration. As is the case with conventional electrosurgical instruments, a range of supply settings may be used for cutting, coagulation and the like. Moreover, it should be appreciated, that the electrodes can be configured in a wide variety of patterns and designs.

An exemplary power supply can create a wattage up to approximately one-hundred-twenty (120) Watts of power for cauterizing the target tissue. The voltage used with a bipolar robotic cauterizer tool is generally between zero (0) volts (V) and one thousand (1000) V peak-to peak, and preferably between one-hundred (100) V and five-hundred (500) V. As long as the jaws and electrodes are both in good contact with the tissue intended to be cauterized and/or cut, there is much less chance of voltage from the electrodes arcing to other conductive components on the instrument (e.g., the wrist, shaft, or pulleys). It should be appreciated, however, that the voltage setting of the electrosurgical power generator will vary depending on the specific dimensions of the electrodes, the tissue to be treated, and the like.

In exemplary embodiments, movement of end effectors 578, 580 are effected through mechanical actuation of a yaw cable 586 and pitch cable 588 via surgeon input devices. Actuation of the pitch cable 588 can rotate the end effectors 578, 580 about the wrist axis A1, while actuation of the yaw cable 586 moves the jaws about axis A2, an axis that is substantially perpendicular to axis A1, between an open and closed position. Typically, the cables 586, 588 are directed through lumens in the shaft and wrist body and through a conductive or nonconductive pulley assembly 590.

As shown in FIGS. 6A-7B, in one configuration the end effectors 578, 580 include a jaw body 792 and a pivot body 794. Nonconductive sleeves 696 can be removably coupled to jaw body 792 to attach electrodes 582A, 582B to the end effector. As shown, the sleeves 696 include grip surfaces 698 that can contact and grip the target tissue. The electrodes 582A, 582B can be molded inserts or a conductive material etched or deposited onto the sleeves. The nonconductive sleeves can include a slot 700 for receiving the jaw body 792 so as to insulate the end effectors from the conductive electrodes. In some configurations, the electrodes and grip surfaces of the jaws can be "non-stick," such as coated with a non-stick polymer, e.g., TEFLON. The conductive leads can be routed through openings 702 in the sleeves 696 and jaw body 792 to contact the electrodes 582A, 582B.

The sleeves 696 are preferably disposable so as to allow the physician to replace the sleeves between each surgical procedure, if desired. The conductive leads 584A, 584B can also be detachable from the electrodes 582A, 582B so as to decouple the electrodes from the power supply. During or after the surgical procedure, the sleeves 696 and the electrodes 582A, 582B can be removed from the jaw body 792 and replaced. Thus, different sized electrodes, a different tooth configuration on the end effectors, a different configuration of electrodes, or the like, can be easily attached to the jaw body 792. In such arrangements, to allow for easy detachment, the conductive leads 584A, 584B can be routed through a lumen in the wrist and to an unprotected path outside the wrist. In other embodiments, the jaws 578, 580, wrist 574, and pulleys 590 can be composed of a nonconductive material and the electrodes can be directly coupled to the end effectors. Consequently, non-conductive bushings can be positioned between the end effectors, and nonconductive sleeves that overly the jaw body 792 are not needed.

Figure 6A:
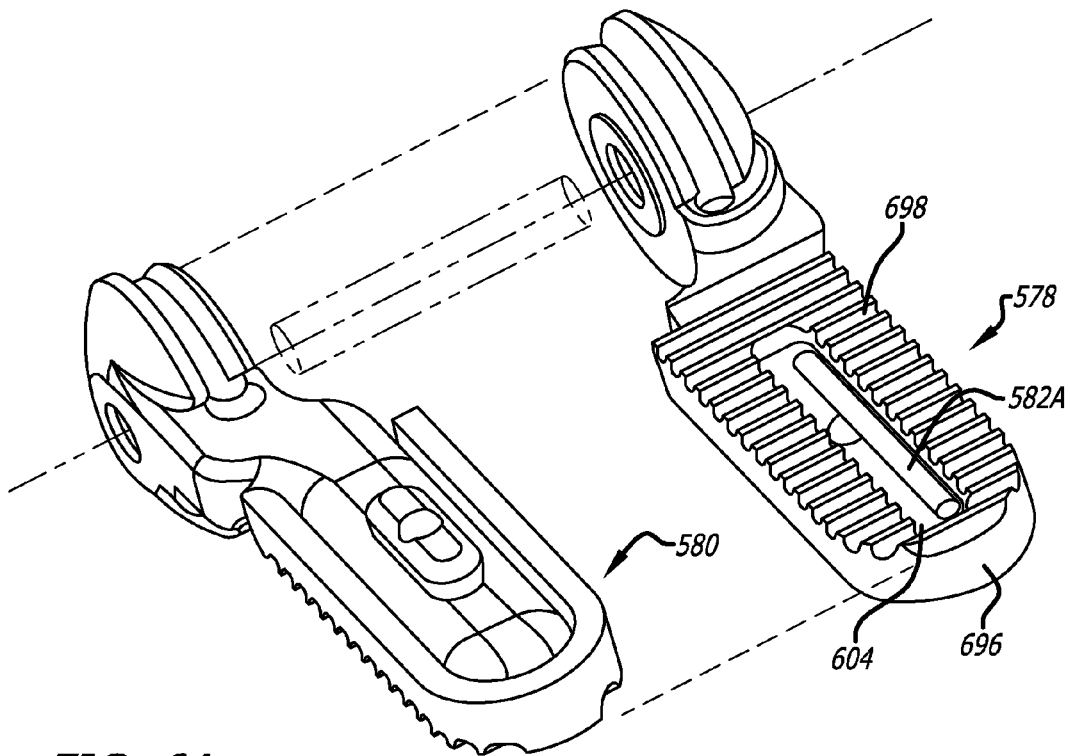
FIG. 6A illustrates a first grip with a recessed electrode.
Figure 6B:
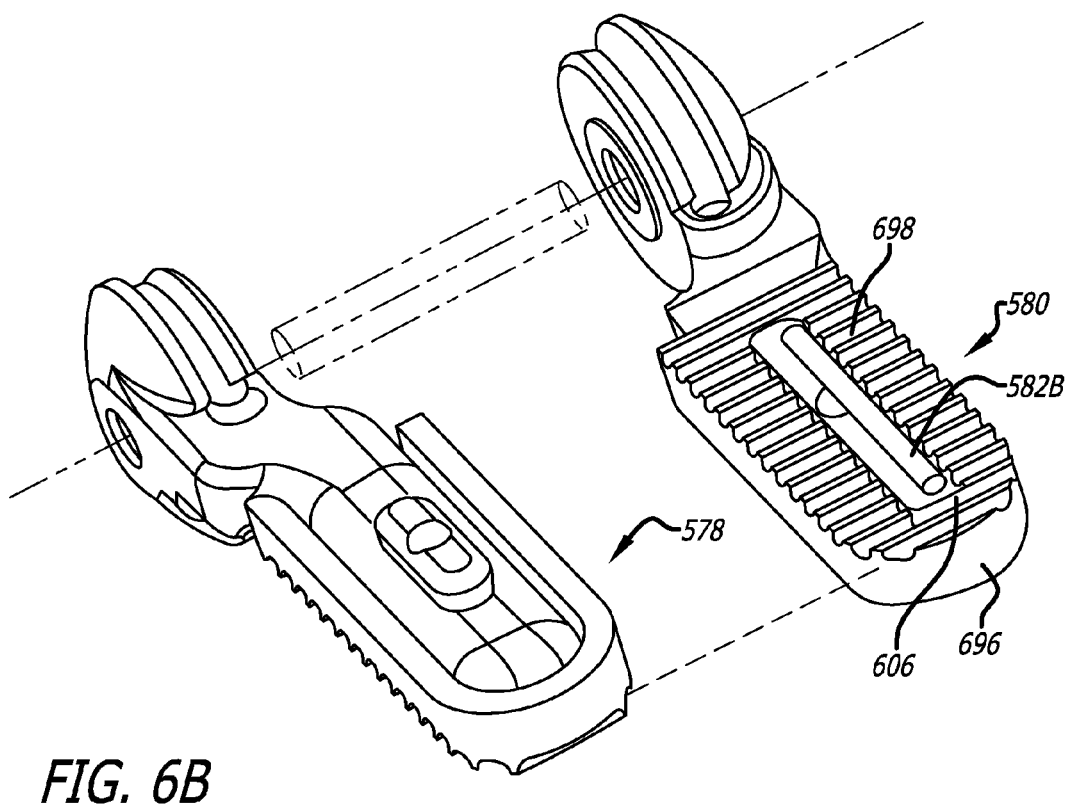
FIG. 6B illustrates an opposing second grip with a raised electrode.
Figure 7A:
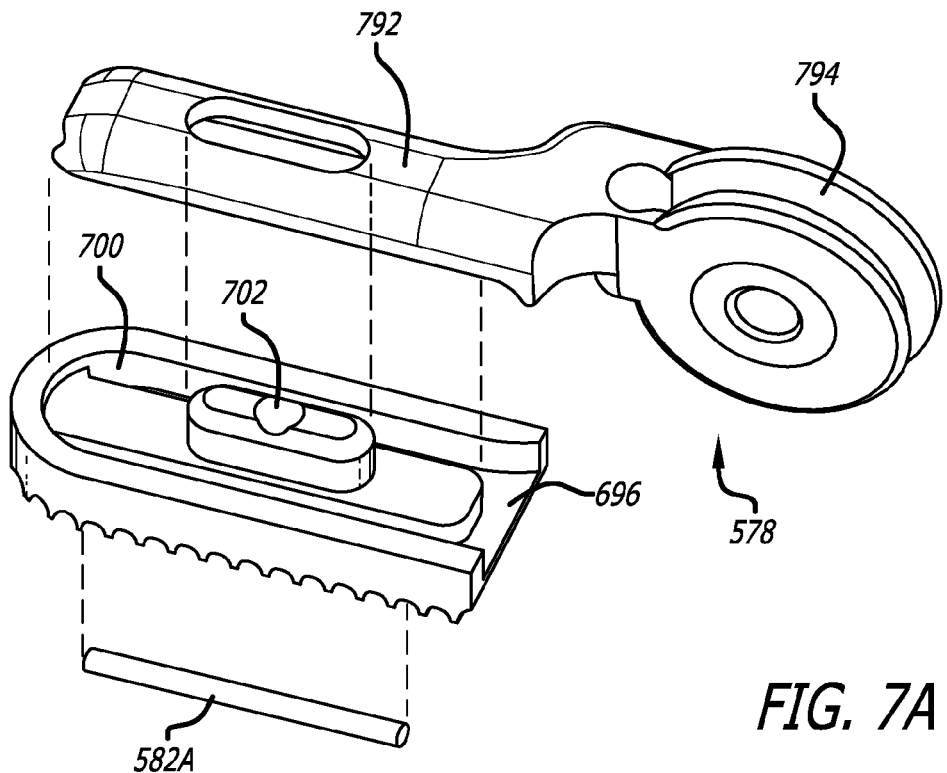
FIGS. 7A and 7B are exploded view showing the electrode, sleeve, and jaw blade of the end effectors illustrated in FIGS. 5A-5B.
Figure 7B:
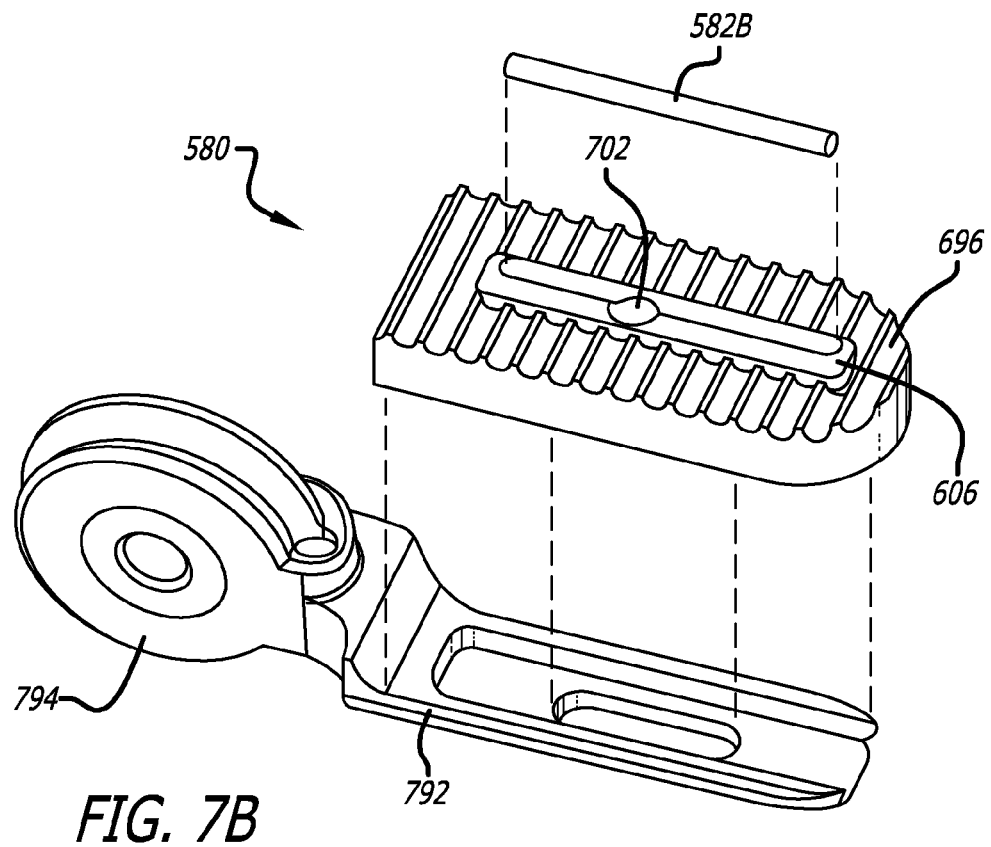

In exemplary arrangements, as shown most clearly in FIGS. 6A and 6B, the first electrode 582A will be disposed in a groove 604 on the jaw or sleeve and the second electrode 582B will be disposed on a boss 606. When the end effectors are moved to the closed position, the boss 606 and groove 604 will interdigitate while still maintaining a gap between the two electrodes. The boss and groove configuration has been found to create thin coagulation heating lines in the tissue when current is delivered between the electrodes. The thin heating lines in the tissue make it easy for the user to cut and separate the tissue by applying a small amount of tension. The time of heating will depend primarily on the size of the tissue being coagulated, the electrode configuration, the current, and the like.

It should be appreciated that the electrodes can be positioned on opposing end effector or on the same end effector. Moreover, the electrodes do not have to be disposed within a groove or on a boss. The electrodes can contact the engaged tissue disposed between the electrodes 582A, 582B and a current is applied between the spaced electrodes to deliver a current flow to cauterize the tissue. If desired, a tension force applied from the end effectors can cut the tissue along the cauterization heat lines to separate the tissue. In this case, the jaws can optionally include a cutting blade disposed on the jaws to facilitate cutting of the tissue. The blade can be stationary or spring loaded and may be conductive or nonconductive.

Drive System

Figure 8:
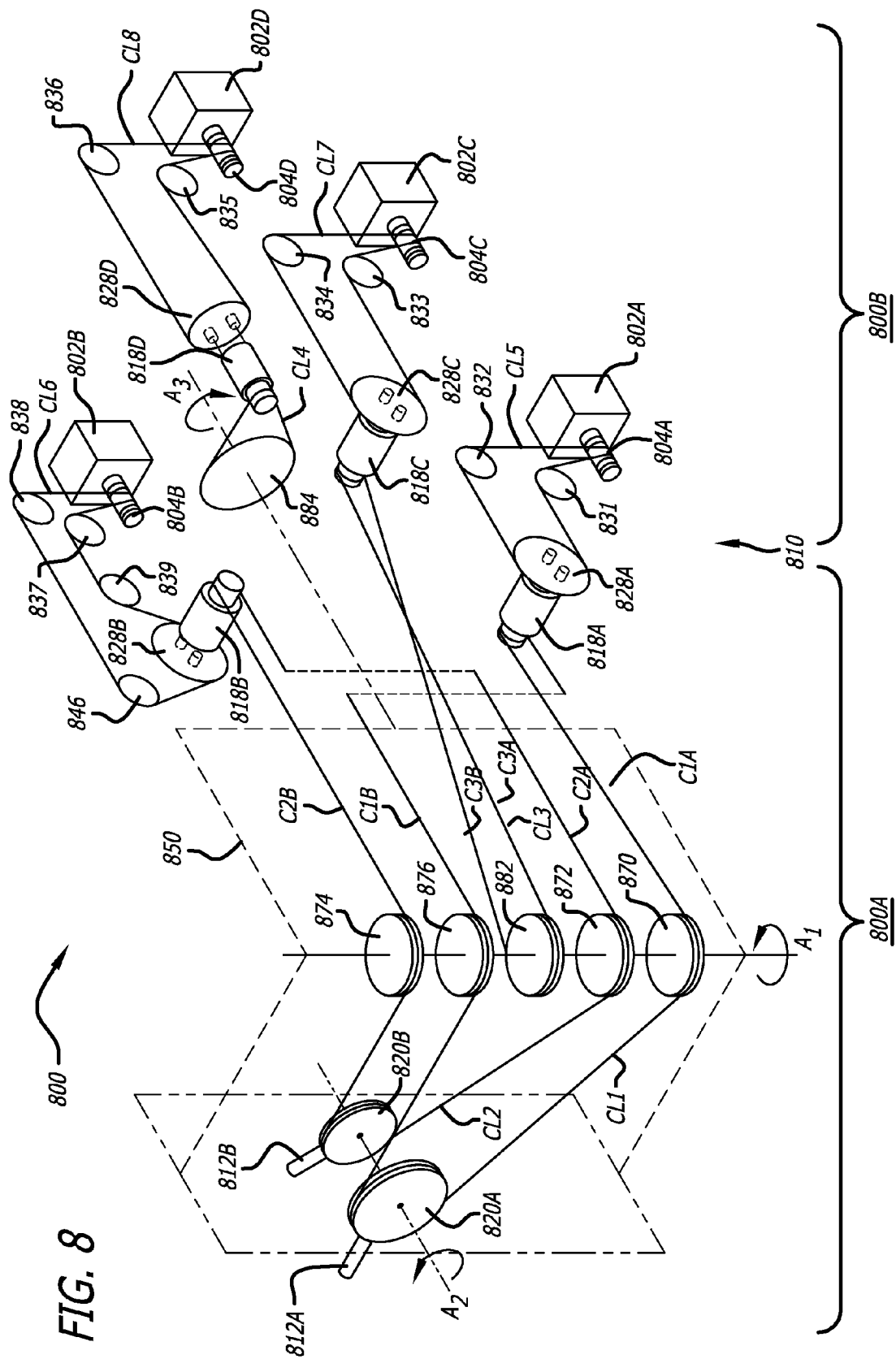
FIG. 8 is a schematic view of the cables and pulleys in the cable drive system of the robotic surgical tool and a robotic surgical arm.

Referring now to FIG. 8, a simplified illustration of a drive system 800 is shown to mechanically couple servomotors 802A, 802B to the end effectors 812A, 812B, respectively through a set of cables and pulleys. The drive system 800 further mechanically couples servomotor 802C to move a joint of the wrist 850 of the robotic surgical tool through another set of cables and pulleys. The drive system 800 further still mechanically couples servomotor 802D to the shaft 416 of the robotic surgical tool through still another set of cables and pulleys.

The drive system 800 includes a tool drive portion 800A and a robotic surgical arm portion 800B that are coupled together at an interface 810. The tool drive portion 800A corresponds to the drive system in the robotic surgical tool 400. The robotic surgical arm portion 800B corresponds to the drive system in the robotic surgical arm 153.

The tool drive portion 800A of the drive system 800 receives mechanical inputs from the robotic surgical arm portion 800B through driven elements 818A-818D, including input disks. From the driven element 818C, the tool drive portion of the drive system translates mechanical inputs from driven element 818C into articulation of a wrist member 850 about the first axis A1. From the driven elements 818A-818B, the tool drive portion of the drive system translates mechanical inputs from the driven element 818A-818B into articulation of the wrist 850 about the first axis A2 as well as into actuation of the two element end effectors 812A, 812B by relative movement of the end effector elements about axis A2. From the driven element 818D, the tool drive portion of the drive system translates mechanical inputs from driven element 818D to effect rotation of the end effectors 812A-812B and the wrist 850 about the axis A3 of shaft 416 by rotating the shaft relative to housing 401 over a limited angle of rotation. In FIG. 8, the rotational motion of shaft 416 about axis A3 is omitted in order to more easily show other elements of the system. Care should be taken to prevent over-rotation of the shaft that may cause cables therein to twist into contact with each other and create friction between the cables.

The robotic surgical arm portion 800B of the drive system 800 includes servomotors 802A-802D that are mechanically coupled to rotatable driver pulleys 828A-828D through cable loops CL5-CL8 to transfer rotation of the servomotors to the rotatable driver pulleys. The servomotors 802A-802D may be standard drive motors having position encoders. However, other actuators may be used, such as hydraulic actuators and piezoelectric motors. To be used as an actuator in the present surgical instrument a drive mechanism should be able to provide variable and controllable force and position control. Capstans 804A-804D are coupled to shafts of the respective servomotors 802A-802D. A pair of ends of each cable loop CL5-CL8 are wrapped within a spiral groove around the capstans 804A-804D so that one end is payed out as one end is take in. A pair of opposite ends of the cable loops CL5-CL8 are wrapped around opposite sides of a pulley of the rotatable driver pulleys 828A-828D. The cable loops CL5-CL8 may also move over one or more idler pulleys 830-840 between the capstans 828A-828D and the rotatable driver pulleys 828A-828D. Additionally, the robotic surgical tool 400 moves along a carriage 237 such that the cable loops CL5-CL8 and one or more idler pulleys 830-840 may adjust in position to allow for the movement in the robotic surgical tool which is not shown in the simplified FIG. 8.

At the interface 810, the rotatable driver pulleys 828A-828D of the robotic surgical arm portion couple to the driven elements 818A-818D of the tool drive portion 800A when the robotic surgical tool 400 is mounted to the robotic surgical arm. The driven elements 818A-818D couple to the rotatable driver pulleys 828A-828D respectively through an adapter that is not shown in the simplified FIG. 8.

When the rotatable driver pulleys 828A-828D of the robotic surgical arm portion couple to the driven elements 818A-818D of the tool drive portion 800A, the servo motor 802A can drive the driven pulley 820A and the end effector 812A. The servo motor 802B can drive the driven pulley 820B and the end effector 812B. The servo motor 802C can drive the driven pulley 882 and yaw the wrist 850. The servo motor 802D can drive the drum 884 and rotate the shaft to roll the wrist 850.

Referring back to the tool portion 800A of the drive system, end effectors 812A,812B; wrist member 850, and the shaft 416 of the tool 400 are driven by cable loops CL1, CL2, CL3, and CL4 arranged into an actuation scheme around a plurality of pulleys. The actuation scheme allows the actuation of a three degree-of-freedom wrist using four cable loops. Alternative actuation schemes using more or less cable loops and cables may be desirable in situations where the forces required for actuation of different motions differ greatly in magnitude. Employing cables instead of gears to control the robotic surgical tool 400 minimizes the amount of friction and backlash within instrument. The combination of small moving masses and low friction enables instrument 400 to provide force reflection to the master control computer 151 at the master console 150 with high sensitivity.

Cable loop CL1 drives end effector 812A and includes a first cable C1A and a second cable C1B forming two sides of the cable loop. The first cable C1A engages the driven element 818A at one end in a first direction, wraps over one or more intermediate idler pulleys 870 in the wrist 850, and couples to the driven pulley 820A at a second end in a first direction. The second cable C2A engages the driven element 818A at one end in a second direction, wraps over one or more intermediate idler pulleys 876 in the wrist 850, and couples to the driven pulley 820A at a second end in a second direction.

Cable loop CL2 drives end effector 812B and includes a first cable C2A and a second cable C2B forming two sides of the cable loop. The first cable C2A engages the driven element 818B at one end in a first direction, wraps over one or more intermediate idler pulleys 872 in the wrist 850, and couples to the driven pulley 820B at a second end in a first direction. The second cable C2A engages the driven element 818B at one end in a second direction, wraps over one or more intermediate idler pulleys 874 in the wrist 850, and couples to the driven pulley 820B at a second end in a second direction.

Cable loop CL3 drives a pulley 882 in the wrist 850 to rotate it about axis A1 and includes a first cable C3A and a second cable C3B forming two sides of the cable loop. The first cable C3A engages the driven element 818C at one end in a first direction and couples to the driven pulley 882 at a second end in a first direction. The second cable C3B engages the driven element 818C at one end in a second direction and couples to the driven pulley 882 at a second end in a second direction.

Cable loop CL4 drives a drum 884 in the housing 401 that is coupled to the shaft 416 to rotate it about axis A3. Similar to the cable loop CL3, the cable loop CL4 and includes a first cable and a second cable forming two sides of the cable loop that are coupled on opposite sides to each of the drum 884 and the driven element 818D.

Referring now to FIG. 9, further details of the drive system 800 for the end effector 812A is illustrated with respect to the robotic surgical tool 400 and the robotic surgical arm 153. FIG. 9 is an additional schematic diagram illustrating the drive system for one of the two end effectors. Servomotor 802A is mechanically coupled by the drive system 800 to the end effector 812A through a series of cables and pulleys.

Cables C5A-C5B of the cable loop CL5 mechanically couple the servomotor 802A to the rotatable driver pulley 828A in the robotic surgical arm 153. The capstan 804A is coupled to the drive shaft 904A of the servomotor 802A. A pair of ends of the cable loop CL5 are wrapped within a spiral groove around the capstan 804A so that one end of the cable C5A is payed out as one end of cable C5B is taken in and visa-versa. The pair of ends at the opposite end of the cable loop CL5 are wrapped around opposite sides of the pulley 928A of the rotatable driver pulley 828A to match the linear direction of the cables C5A-C5B, as one is taken up the other is payed out. The cable loop CL5 may also move over one or more idler pulleys 831-832 between the capstan 804A and the pulley 928A of the rotatable driver pulley 828A. Through the cable loop CL5, capstan 804A, and pulley 928A, the rotation of the servomotor 802A is mechanically coupled to the rotatable driver pulley 828A.

The rotatable driver pulley 828A mechanically couples to the input disk 918A of the driven element 818A by means of a rotatable adapter 910A at the interface 810.

In the robotic surgical tool 400, cables C1A-C1B of the cable loop CL1 mechanically couple the driven element 818A to the driver pulley 820A and its end effector 812A. One end of each of the cables C1A-C1B of the cable loop CL1 wrap around and couple to the actuating spool 920A of the driven element 818A. The opposite end of each of the cables C1A-C1B of the cable loop CL1 wrap around opposite sides and couple to the driven pulley 820A. The cable loop CL1 may also move over one or more idler pulleys 870 between the input disk 918A and the pulley 820A. Through the cable loop CL1, input disk 918A, and pulley 820A, the rotation of the driven element 818A is mechanically coupled to the pulley 820A and the end effector 812A.

Generally, rotation of the elements 818A-818D in a first direction causes the pulleys to rotate in a first direction by pulling on a first side of the cable loop and paying out the second side of the cable loop. Rotation of the elements 818A-818D in a second direction causes the pulleys to rotate in a second direction by pulling on the second side of the cable loop and paying out the first side of the cable loop.

In the tool portion 800A, the amount of rotation of the driven elements 818A-818D that is transferred into rotation at the axes A1-A3 is a function of the radius of the actuating spools (such as spool 920A) at the driven elements, about which the cables wrap at one end, and the radius of the driven pulleys 820A,820B, 882 and drum 884 at the second end. Actuating spools can be chosen with differing radius at the driven elements 818A-818C to obtain more or less rotation in the driven members given that the driven pulleys 820A,820B, 882 are often constrained by size limitations at the distal end of the shaft 416 of the robotic surgical tool. However, with larger shaft diameters the radius of the driven pulleys 820A, 820B, 882 can be increased to provide a greater range of motion and force. Additionally, the radius of the driven pulleys 820A,820B, 882 may be chosen to allow the cables to properly engage idler pulleys. For example, driven pulleys 820A-820B may have different diameters in order to allow their cables to suitably engage their respective intermediate idler pulleys. Additionally, the radius of idler pulleys may be chosen to keep the cables they are guiding straight but are preferably small to minimize space requirements.

At the interface 810, the ratio of the radius of rotatable driver pulleys 828A-828D to the radius of the actuating spool of the driven elements 818A-818D acts like a transmission. The ratio of these radiuses change the amount of linear distance of cable that is pulled in and payed out at the actuating spool in the robotic surgical tool from that of the linear distance of cable that is pulled in and payed out at the rotatable driver pulleys 828A-828D.

In the robotic surgical arm portion 800B, the amount of rotation of the capstans 818A-818D at the motors 802A-802D that is transferred to the rotatable driver pulleys 828A-828D is a function of the radius of the capstans 818A-818D and the radius of the rotatable driver pulleys 828A-828D. As these elements are found in the robotic surgical arm, their radius are constant for each type of tool that is mounted to the robotic surgical arm.

For the servomotors 802A-802B to drive the end effectors 812A-812B, a torque differential coupling matrix may be used to provide a translation of torque at the servomotors to the driven pulleys 802A-820B about their respective axis. For the servomotors 802C-802D to respectively drive the driver pulley 882 and the drum 882, the coupling matrix is also used to translate a torque at the servomotors to the driven pulley 882 and drum 884 about their respective axis. At the end effectors 812A-812B, the torque at the driven pulleys 802A-802B can be simply converted into a linear force at tips of the end effectors knowing the radius of the pulleys and the length of the end effectors extending beyond the pulleys. This linear force at the tips of the end effectors is often referred to as a tip force which is further described with reference to FIG. 11 below.

Figure 10:
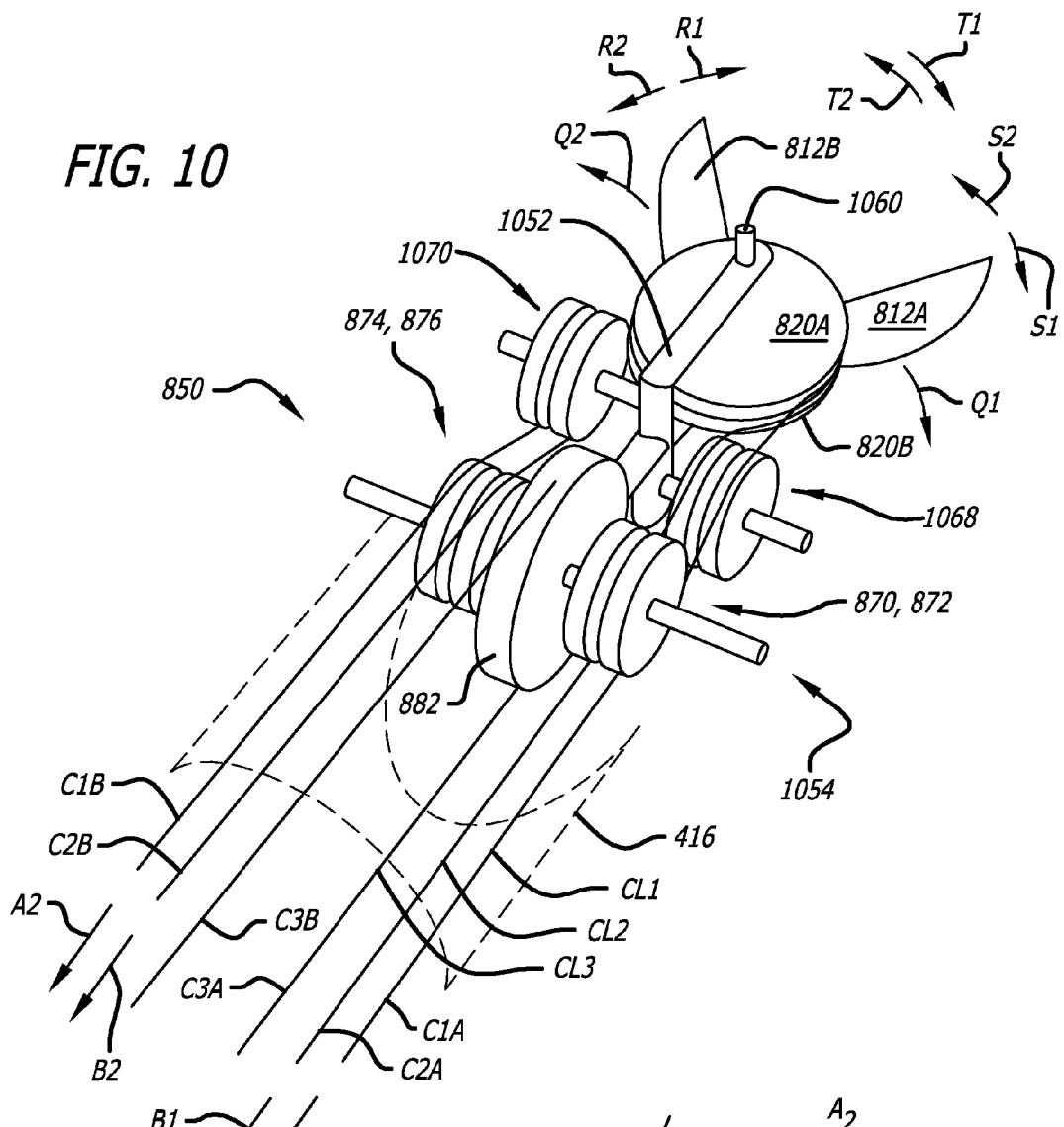
FIG. 10 shows a three-dimensional schematic view of the cable drive system to the end effectors and wrist mechanism at the end of the robotic surgical tool.

Referring now to FIG. 10, three cable loops CL1, CL2, CL3 are used to effect movement of the wrist mechanism 850 as previously discussed. Cable loops CL1 and CL2 are used to effect movement in the end effectors 812A,812B about the pivotal connection or pin 1060. It will be appreciated that four cables may extend through the wrist-like member to effect movement in the end effectors 812A,812B, although fewer cables would be required for a single-finger end effector. Cable loop CL3 is used to effect movement in the wrist 850 about the pivotal connection or pin 1054.

One end of each cable C1A,C1B of the cable loop CL1 is anchored to the drive pulley 820A to effect movement in the end effector 812A about the pivotal pin 1060. One end of each cable C2A,C2B of the cable loop CL2 is anchored to the drive pulley 820B to effect movement in the end effector 812B about the pivotal pin 1060. One end of each cable C3A,C3B of the cable loop CL3 is anchored to the drive pulley 882 to effect movement in the wrist 850 about the pivotal pin 1054.

As previously discussed, one or more idler pulleys may be used to route the cable loops CL1, CL2 through the wrist 850 to the respective driven pulleys 820A-820B.

The cable of the cable loop CL1 rides over an outer idler pulley 870 of the first pulley set and an outer idler pulley in the second pulley set 1068 and into a circumferential channel in the driven pulley 802A over the first cable portion C1A. From the driven pulley 802A, the cable of the cable loop CL1 exits from the circumferential channel in the driven pulley 802A rides over an inner idler pulley in the third pulley set 1070 and the inner idler pulley 876 in the fourth pulley set over the second cable portion C1B.

The cable of the cable loop CL2 rides over an inner idler pulley 872 of the first pulley set and an inner idler pulley in the second pulley set 1068 and into a circumferential channel in the driven pulley 802B over the first cable portion C2A. From the driven pulley 802B, the cable of the cable loop CL2 exits from the circumferential channel in the driven pulley 802B rides over an outer idler pulley in the third pulley set 1070 and the outer idler pulley 874 in the fourth pulley set over the second cable portion C2B.

To use the end effector 812A, when cable C1A is pulled in the direction of arrow A1, cable C1B is payed out and the end effector 812A is caused to displace angularly about the pivotal connection 1060 in the direction of arrow S1. If cable C1B is pulled in the direction of arrow A2, cable C1A is payed out and the end effector 812A is caused to displace angularly about the pivotal connection 1060 in the direction of arrow S2.

To use the end effector 812A, when cable C2A is pulled in the direction of arrow B1, cable C2B is payed out and the end effector 812B is caused to displace angularly about the pivotal connection 1060 in the direction of arrow R1. When cable C2B is pulled in the direction of arrow B2, cable C2A is payed out and the end effector 812B is caused to displace angularly about the pivotal connection 1060 in the direction of arrow R2.

Thus to coincidentally close the jaws of the end effectors 812A-812B together without any wrist movement, cable C1B is pulled in the direction of arrow A2 and cable C2A is pulled in the direction of arrow B1 simultaneously. To coincidentally open the jaws of the end effectors 812A-812B together without any wrist movement, cable C1A is pulled in the direction of arrow A1 and cable C2B is pulled in the direction of arrow B2 simultaneously.

Furthermore, the orientation of the end effectors 812A-812B may be moved together as a whole in the same direction relative to the wrist member 52, as indicated by the arrows T1 and T2. In this case, cable C1A is pulled in the direction of arrow A1 and cable C2A is simultaneously pulled in the direction of arrow B1 so as to displace both end effectors 812A-812B in the direction of arrow T1. Similarly, to move the end effectors 812A-812B in the direction of arrow T2, C1B is pulled in the direction of arrow A2 and cable C2B is simultaneously pulled in the direction of arrow B2.

All of the tension in the activation cables C1A,C1B,C2A, C2B, in the surgical tool may not be transferred into a force at the tip of the end effectors 812A, 812B due to the small sizes of the pulleys coupled to the end effectors.

Figure 11:
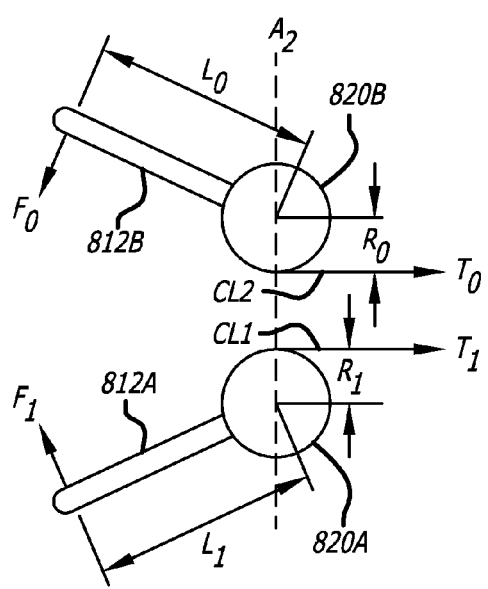
FIG. 11 is a simplified schematic diagram illustrating the force transmission provided by a pair of jaws of the end effectors.

Referring now to FIG. 11, a simplified schematic diagram illustrates the force transmission that may be provided by a pair of jaws of end effectors 812A-812B such as a gripper to tissue. As discussed previously, the end effectors 812A-812B are coupled to driven pulleys 820A-820B respectively and may be rotated about the axis A2. The pulleys 820A-820B are respectively driven by the cable loops CL1-CL2.

T0 is the cable tension in the activation cable loop CL2 for the end effector 812B. T1 is the cable tension in the activation cable loop CL1 for the end effector 812A. R0 and R1 are the respective radii of the pulleys about which the jaws rotate of the end effector. L0 and L1 are the respected distances from the center axis of the pulleys to the tip of the jaw. F0 and F1 are the respective forces applied at the tips of the jaws and are proportional to the cable tensions T0 and T1. The ratios R0/L0 and R1/L1 may reduce the respective forces F0 and F1 that is to be generated by the tensions T0 and T1 respectively. This is because the ratios R0/L0 and R1/L1 may often be less than one and typically are less than 0.5. While techniques of obtaining a mechanical advantage may increase the ratios at the end effectors, such as those described in U.S. Pat. No. 6,206,903 by Ramans, with any reduction in transferring the cable tension to the tip force, it is important to drive the maximum possible tension into the cables of the robotic surgical tool.

While a particular embodiment of a drive system 800 has been described, possible changes to the configuration of pulleys, cables and motors described above will be apparent to those of skill in the art. For example, an alternate tool drive portion for the drive system is described in U.S. Pat. No. 5,792,135, the full disclosure of which is incorporated herein by reference. The choice of the particular drive scheme employed in a particular embodiment will depend on the constraints of the forces required to be exerted by the instrument and the need to reduce the inertia and friction of the parts of the instrument that move during its actuation. For example, a wide variety of alternative drive systems might be employed, including alternative cabling arrangements, drive chains or belts, hydraulic drive systems, gear trains, rods, wire, or the like. In some of these drive systems, motion of end effectors 812A-812B about the axes may be coupled to multiple driven elements 818. In other embodiments, there may be a one to one correspondence between driven elements 818 and motion of an end effector element about an axis. Still other embodiments may require fewer (or more) driven elements to effect the desired degrees of freedom, for example, when a single element end effector is provided. Hence, manipulation of the end effector via interface 810 will generally involve some reconfiguration of the robotic system during the tool change, such as through the coupling matrix described previously.

Maximum Torque Driving of Robotic Surgical Instruments

Figure 12A:
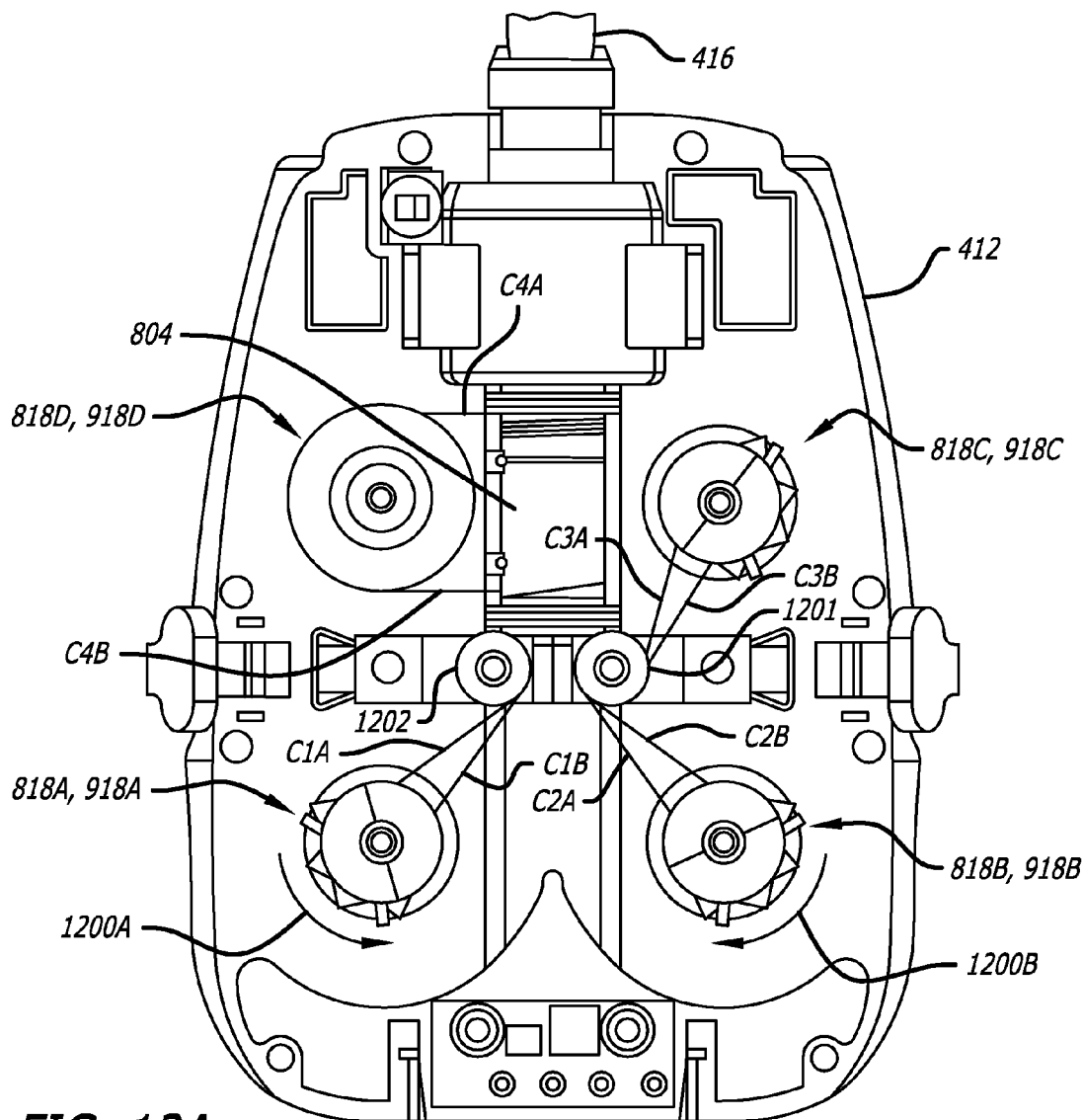
FIG. 12A is a top view of the surgical instrument shown in FIG. 4 with a housing cover having been removed to show working elements inside a mountable housing.

Referring now to FIG. 12A, a top view of the tool base 412 is illustrated with cover removed to show the driven elements 818A-818D and the cables C1A-C1B, C2A-C2B, C3A-C3B, and C4A-C4B of the respective cable loops CL1, CL2, CL3, and CL4 shown in FIG. 8. The driven elements 818A-818C each include an input disk 918A-918C and an actuation spool.

Figure 12B:
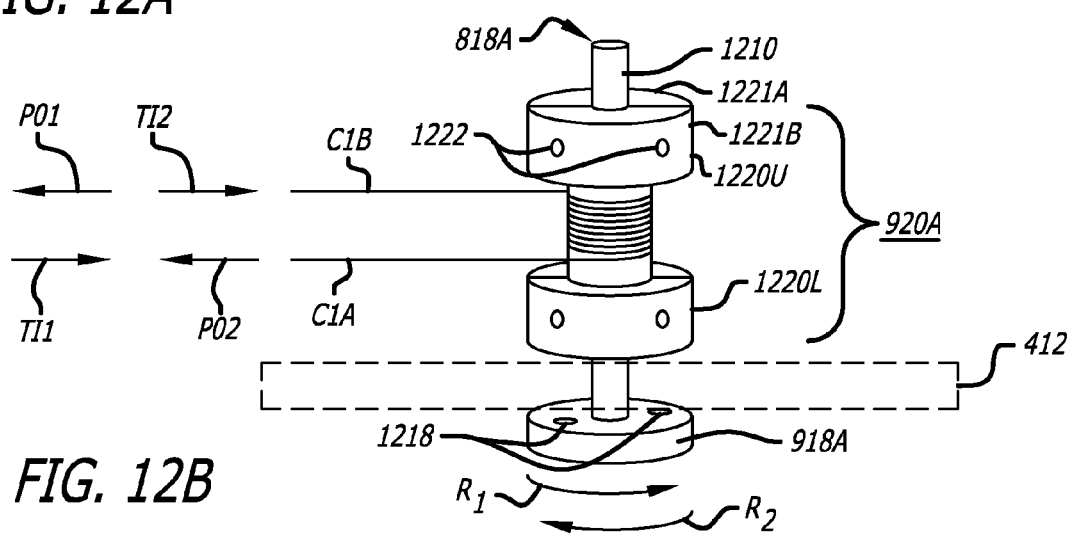
FIG. 12B is a side view of a driven element extending through the base of the mountable housing illustrated in FIG. 12A.

Referring now to FIG. 12B, a side view of the driven element 818A is illustrated that is also representative of the driven elements 818B-818C. The driven element 818A includes the input disk 918A, a drive shaft 1210 coupled to the input disk, and the actuating spool 920A coupled to the drive shaft. The input disk includes pins 1218 to mate with the adapter 910A of the interface. The drive shaft 1210 extends up through an opening in the tool base 412 into the interior of the mountable housing. The actuating spool 920A includes an upper clamping pulley 1220U and a lower clamping pulley 1220L. Each of the upper clamping pulley 1220U and the lower clamping pulley 1220L have a first clamp half 1221A and a second clamp half 1221B. A pair of fasteners 1222 couples the first clamp half 1221A to the second clamp half 1221B and each clamping pulley 1220U, 1220L to the drive shaft 1210. The cable C1B is wrapped around in a spiral groove and coupled to the upper clamping pulley 1220U. The cable C1A is wrapped around in a spiral groove and coupled to the lower clamping pulley 1220L.

With each of their fasteners 1222 being loose, the upper clamping pulley 1220U and the lower clamping pulley 1220L may turn independently of each other about the drive shaft 1210. The upper clamping pulley 1220U and the lower clamping pulley 1220L can be used to assist in the initial assembly of the cable loop CL1 through the robotic tool to the driver pulley 820A and the alignment of the end effector 812A. The upper clamping pulley 1220U and the lower clamping pulley 1220L can also be used to initially set and later adjust the tension in the cables C1A-C1B of the cable loop CL1 between the driver pulley 820A and the actuating spool 920A.

The ends of the cables C1A-C1B of the cable loop CL1 are wrapped around the clamping pulleys 1220U-1220L in their respective spiral grooves so that one end pays out while the other end is taken in and visa-versa. If the input disk is rotated in the direction of arrow R1, cable C1A may be taken in as indicated by arrow $TI_1$ and cable C1B may be payed out as indicated by arrow $PO_1$. If the input disk is rotated in the opposite direction as indicated by arrow R2, cable C1B may be taken in as indicated by arrow $TI_2$ and cable C1A may be payed out as indicated by arrow $PO_2$.

Referring now back to FIG. 12A, the driven element 818D has a different type of actuation spool but operates similarly so that cable C4A of cable loop CL4 is taken in while cable C4B of the cable loop CL4 is payed out and visa versa. An end of the cables C4A and C4B of the cable loop CL4 wrap around the drum 884 to rotate the shaft 416.

The cables C2A, C2B of the cable loop CL2 and cables C3A, C3B of the cable loop CL3 respectively ride on first and second pairs of stacked idler pulleys 1201 in the tool base 412 before entering the shaft 416. The cables C1A, C1B of the cable loop CL1 ride on a pair of stacked idler pulleys 1202 in the tool base 412 before entering the shaft 416.

As discussed previously in reference to the drive system 800, the cables C1A, C1B of the cable loop CL1 drive the end effector 812A and the cables C2A, C2B of the cable loop CL2 drive the end effector 812B. In a typical robotic surgical tool 400, rotating the driven elements 818A, 818B and the respective input disks 918A, 918B in opposite directions respectively closes the jaws or end effectors 812A, 812B together as illustrated by the arrows 1200A-1200B indicating the close rotational direction. Input disk 918A may be referred to as input disk six. Input disk 918B may be referred to as input disk seven.

Referring now to FIGS. 13A-13C, FIGS. 14A-14D, and FIGS. 15A-15C, the operation of closing the end effectors 812A-812B from an open position to drive to maximum torque is now described. FIGS. 15A-15C illustrate the operation of the master grips 350A-350B around the touch sensitive handle 325 in the master console 150 in the context of grip space. That is, the actual angular position $\theta^a{}_M$ of the master grips 350A-350B is provided to the servomechanism control system (see FIGS. 18A-18B) to drive the input disks and the end effectors 812A, 812B. FIGS. 13A-13C illustrate the operation of the input disks 918A-918B in the robotic surgical tool at the interface 810 in the context of disk space. The input disks 918A-918B physically rotate over angles in disk space in response to the servo-motors 802A-802B and the motor torque input thereto. FIGS. 14A-14D illustrate the operation of the end effectors 812A-812B in the robotic surgical tool in the context of wrist space at the wrist 850. The desired angular position $\theta^d{}_S$ of the slave end effectors 812A-812B in wrist space is derived as a function of the actual angular position $\theta^a{}_M$ of the master grips 350A-350B in grip space. The desired angular position $\theta^d{}_S$ of the slave end effectors 812A-812B is processed by the servomechanism control system in an attempt to make the difference between the desired angular position $\theta^d{}_S$ and the actual angular position $\theta^a{}_S$ of the slave end effectors 812A-812B be zero. The servomechanism control system may also take into account the velocity of the master grips in forming a joint torque as is described below with reference to FIGS. 18A-18B.

Referring now to FIGS. 13A, 14A, 15A, and 20A, the master grips 350A-350B are substantially open having a large positive actual angular position $\theta^a{}_M$ at a point W, for example, on the curve 2002 illustrated in FIG. 20A. The function f(.) as is discussed further below and exemplary illustrated in FIG. 20A, is used to determine the desired end effector slave angle $\theta^d{}_s$. The servomechanism drives the input disks 918A-918B to a first position 918A'-918B' with the jaws or end effectors 812A-812B being open as illustrated in FIG. 14A. The jaws or end effectors 812A-812B are at a first actual end effector slave angle $\theta^a{}_s$ which is congruent to the positive desired end effector slave angle $\theta^d{}_s$. Note that as the master grips 350A-350B are closed from this position, the input disks 918A, 918B are rotated in the respective close directions 1200A-1200B and the end effectors 812A-812B close in the direction of arrows S2 and R1, respectively.

Referring now to FIGS. 13B, 14B, 15B, and 20A, the master grips 350A-350B are closed to a point where the end effectors 812A-812B just make contact. The actual master angular position $\theta^a{}_M$ is at a point O, zero degrees for example, on the curve 2002 illustrated in FIG. 20A. The function f(.), such as that illustrated in FIG. 20A, may be used to determine the desired end effector slave angle $\theta^d{}_s$. At the position O on curve 2002, with the master angular position $\theta^a{}_M$ being zero degrees for example, the desired end effector slave angle $\theta^d{}_s$ is zero degrees as well. The servomechanism drives the input disks 918A-918B so they are rotated in their respective close directions 1200A-1200B to a second position 918A''-918B'', that may be referred to as a disk bumper position, where the jaws or end effectors 812A-812B just touch together as illustrated in FIG. 14B. The jaws or end effectors 812A-812B are at a second actual end effector slave angle $\theta^a{}_s$ of substantially zero degrees that is congruent to the positive desired end effector slave angle $\theta^d{}_s$.

With the input disks at the respective disk positions 918A''-918B'', the jaws or end effectors 812A-812B are substantially at an actual slave angle $\theta^a{}_s$ of zero degrees with little to no force being applied at tips of the end effectors when they just touch together or just touch tissue. The end effectors 812A-812B may be closed a little further on tissue S in a surgical site and then have a tip force $F_m$ applied to the tissue to cauterize or seal it together. While the jaws or end effectors 812A-812B may not actually move much more, such that the actual end effector slave angle remains substantially the same, additional torque can be generated at the driven pulleys 820A-820B so that the tip force Fm may be generated. Referring now to FIGS. 13C, 14C, 14D, 15C, and 20A, the master grips 350A-350B are closed to a substantially closed position. The actual master angular position $\theta^a{}_M$ is a negative number at a point P', negative five degrees for example, on the curve 2002 illustrated in FIG. 20A. The function f(.), such as that illustrated in FIG. 20A, may be used to determine the desired end effector slave angle $\theta^d{}_s$. At the point P' on curve 2002, with the master angular position $\theta^a{}_M$ being negative five degrees for example, the desired end effector slave angle $\theta^d{}_M$ may be negative 35 degrees for example.

A desired end effector slave angle $\theta^d{}_s$ that has a negative value is theoretically illustrated in FIG. 14D by the end effectors 812A-812B crossing over one another. However, the end effectors 812A-812B do not actually cross over one another. Instead, the actual end effector slave angle $\theta^a{}_s$ substantially differs from the desired end effector slave angle $\theta^d{}_s$ as can be seen by a comparison of FIGS. 14C and 14D. While the actual end effector slave angle $\theta^a{}_s$ remains substantially close to zero degrees, the torque applied at the joint of the end effectors 812A-812B has increased significantly. This is because the servomechanism continues to try and drive the end effectors 812A-812B so that the actual end effector slave angle $\theta^a{}_s$ become congruent to the negative value of the desired end effector slave angle $\theta^d{}_s$. As the end effectors 812A-812B may not cross over one another, the actual end effector slave angle $\theta^a{}_s$ will not become congruent to the negative value of the desired end effector slave angle $\theta^d{}_s$. Thus, with the master grips at their substantially closed position, the servomechanism continues to try and drive the end effectors 812A-812B to the negative value of the desired end effector slave angle $\theta^d{}_s$ unless it is limited by maximum torque values or a physical limitation in the cable drive system 800 of the robotic surgical arm 153 and/or the robotic surgical tool 400.

In FIG. 13C, the input disks 918A-918B are further rotated in their respective close directions 1200A-1200B to a third position 918A'''-918B''' through a maximum torque angle of rotation $\theta_{TmaxA}$ and $\theta_{TmaxB}$, respectively where maximum torque is applied to the tissue S by the servomechanism being limited to a maximum torque limit. Robotic surgical tools may have different values of $\theta_{TmaxA}$ and $\theta_{TmaxB}$ for each input disk 918A,918B to generate a maximum torque at the pulleys 820A,820B after the tips touch. This may be due to differences in cable drive systems and general instrument friction or the desire to apply a varying force to the tissue.

As illustrated in FIG. 14C, the jaws or end effectors 812A-812B have an actual end effector slave angle $\theta^a{}_s$ that remains at a substantially zero degrees but now has a tip force Fm generated at the tip of the end effectors 812A-812B. As the instrument jaws or end effectors 812A-812B come in contact to a common object, such as the tissue S, the input disks 918A,918B continue to rotate, applying tension to the cables C1B and C2A of the respective cable loops CL1 and CL2, for example, even though there is little movement of the end effectors 812A-812B. The tension on the cables C1B and C2A of the respective cable loops CL1 and CL2 translates into maximum torque at the end effectors 812A-812B and a tip force Fm for gripping tissue within the jaws of the end effectors 812A-812B.

The input disks 918A-918B have rotated from their second positions (which may be referred to as a disk bump position) until a pre-determined maximum torque setting has been reached or the user releases the master grip driving the input disks. Previously a maximum rotational position limit in wrist space could have limited the rotation of the input disks 918A-918B so that the maximum torque setting would not be reached with stretched cables. For example, consider the function f(.) illustrated by curve 2001 in FIG. 20A. The point P on curve 2001, a maximum rotational position limit in wrist space when the master grips 350A-350B are fully closed, may not provide enough torque to drive the end effectors to a maximum joint torque.

In the embodiments of the invention, the maximum rotational position limit in wrist space is extended so that sufficient torque can be generated to drive the end effectors to the maximum joint torque limits. For example, curve 2001 may be used for the function f(.) so that the point P', a maximum rotational position limit in wrist space when the master grips 350A-350B are fully closed, provides enough torque to drive the end effectors to a maximum joint torque. The gain constant $K_p$ for converting angular distance of the grip to a portion of the desired torque value at the joint may additionally or alternatively be increased to $K_{p'}$ to saturate the torque limit sooner as the master grips 350A,350B are closed rather than later to drive to maximum torque limits. The increase in the gain constant $K_p$, is described further below with reference to FIGS. 18A-18B.

With the control system limitation being removed, the physical limitations of the cable drive system 800 may still limit the rotation of the input disks 918A-918B in disk space. In FIG. 13C, physical limitations of the cable drive system 800 may limit the rotation of the input disks 918A-918B to their physically limited angles of rotation $\theta_{PLA}$ and $\theta_{PLB}$, respectively. As illustrated, the physically limited angles of rotation $\theta_{PLA}$ and $\theta_{PLB}$ are well beyond the expected maximum torque angles of rotation $\theta_{TmaxA}$ and $\theta_{TmaxB}$. The servomechanisms may drive the input disks 918A-918B so that the angles $\theta_{TmaxA}$ and $\theta_{TmaxB}$ may go as high as $\theta_{PLA}$ and $\theta_{PLB}$, the physical limit in the range of motion in robotic surgical tool and the robotic surgical arm. However, if driving to the maximum joint torque and a physical limit is reached, a cable is well beyond the expected cable stretch, up to a point where the cable should be replaced before it breaks. That is, over the life of the cables in the tool, when driving to the maximum torque setting, a physical limit of the position of the input disks should never be reached or else the tool should be replaced or repaired.

In one embodiment of the invention it has been determined by experimentation that after the cables have stretched, that a desired end effector slave angle $\theta^d_s$ of negative seventy degrees in wrist space with the master grips being substantially closed, will ensure that a maximum torque at the pulleys 820A,820B will always be reached over the life of a robotic surgical tool or instrument.

As discussed previously, the servomechanism continues to try and drive the end effectors 812A-812B to the negative value of the desired end effector slave angle $\theta^d_s$ when the master grips 350A-350B are at their substantially closed position unless limited by maximum torque values. The servomechanism is limited by an upper torque limit (UTL) and a lower torque limit (LTL). As the joint torque is a large negative value when trying to reach the negative value of the desired end effector slave angle $\theta^d_s$, the lower torque limit limits the joint torque value generated by the servomechanism.

In one embodiment of the invention, a lower torque limit setting of 0.39 Nm for the servomechanism yielded a measured tip force Fm at the tips of end effectors 812A-812B of approximately 3.4 pounds (lbs). In another embodiment of the invention with a differing jaw length, a lower torque limit setting of 0.14 Nm for the servomechanism yielded a measured tip force of approximately 1.4 lbs. The amount of force applied to tissue may be desirable for certain surgical procedures such as sealing tissue and vessels, and can vary between tool types.

Control System for Master/Slave Robotic Surgical Systems

FIG. 16A schematically illustrates a block diagram of a control architecture 1600 for a master/slave robotic system that may be executed by the computer 151 in the master console 150. The control architecture 1600 includes a bilateral controller 1605 to interface between the master control at the master console 150 ("Master Manipulator" 1602) and the slave control at the robotic surgical arm 153 ("Slave Manipulator" 1608). The control architecture 1600 may feed forward control inputs from the human operator 1601 to the slave manipulator 1608 in the surgical environment 1609 and may feed back a force as well as sensor information to the master manipulator 1602 and the human operator 1601.

The human operator 1601, such as a surgeon, moves an input device of a master manipulator 1602 by applying manual or human forces $f_h$ against the input device. One such input device are the grips 35A-350B. Encoders of master manipulator 1602 generate master encoder signals em which are interpreted by a master input/output processor 1603 to determine the master joint positions $\theta_m$ ("theta sub m"). The master joint positions are used to generate Cartesian positions $x_m$ of the input device of the master using a master kinematics model 1604. The Cartesian positions $x_m$ of the input device are coupled into the bilateral controller 1605.

In the surgical environment 1609, the tissue structures in the surgical workspace can impose environmental forces $f_e$ against a surgical end effector (and possibly against other elements of the tool and/or manipulator). The environmental forces $f_e$ from the surgical environment 1609 alter the position of the slave manipulator 1608, which are read by an encoder as slave encoder values $e_s$ which are transmitted to the slave input/output processor 1607. The slave input/output processor 1607 interprets the slave encoder values $e_s$ to determine joint positions $\theta_s$. The joint positions $\theta_s$ are then used to generate Cartesian slave position signals $x_s$ according to the slave kinematics processing block 1606. The slave position signals $x_s$ are coupled into the bilateral controller 1605.

The bilateral controller 1605 uses the input master and slave Cartesian positions $x_m$, $x_s$ to generate the desired Cartesian forces to be applied by the slave $f_s$ so that the surgeon can manipulate the slave manipulator 1608 as desired to perform a surgical procedure. Additionally, bilateral controller 1605 uses the Cartesian master and slave positions $x_m$, $x_s$ to generate the desired Cartesian force feedback $f_m$ that is coupled into the master so as to provide force feedback to the surgeon.

In general, bilateral controller 1605 generates the slave and master forces $f_s, f_m$ by mapping the Cartesian position of the master in the master controller workspace with the Cartesian position of the end effector in the surgical workspace according to a transformation. Preferably, the control system 1600 will derive the transformation in response to state variable signals provided from the imaging system so that an image of the end effector in a display appears substantially connected to the input device. These state variables will generally indicate the Cartesian position of the field of view from the image capture device, as supplied by the slave manipulators supporting the image capture device. Hence, coupling of the image capture manipulator and slave end effector manipulator is beneficial for deriving this transformation. Bilateral controller 1605 may be used to control one or more robotic surgical arms 153 and the robotic surgical tools 400 coupled thereto. Bilateral controller 1605 may also be provided with additional input signals such as various types of sensors encoders, tachometers, and current-meters, for example.

Based generally on the difference in position between the master and the slave in the mapped workspace, bilateral controller 1605 generates a Cartesian slave force $f_s$ to urge the slave to follow the position of the master. The slave kinematics 1606 are used to interpret the Cartesian slave forces $f_s$ to generate joint torques $\tau_s$ ("tau sub s") of the slave which will result in the desired forces at the end effector. Slave input/output processor 1607 uses these joint torques to calculate slave motor currents $i_s$, which reposition the slave manipulator 1608 at slave position $x_e$ within the surgical worksite.

The desired feedback forces from bilateral controller are similarly interpreted from Cartesian force on the master $f_m$ based on the master kinematics 1604 to generate master joint torques $\tau_s$. The master joint torques are interpreted by the master input/output controller 1603 to provide master motor current $i_m$ to the master manipulator 1602, which changes the position $x_h$ of the hand held input device in the surgeon's hand.

It will be recognized that the control system 1600 illustrated in FIG. 16A is a block diagram simplification. For example, the surgeon does not only apply forces against the master input device, but also moves the handle within the master workspace. Similarly, the motor current supplied to the motors of the master manipulator may not result in movement if the surgeon maintains the position of the master controller. Nonetheless, the motor currents do result in tactile force feedback to the surgeon based on the forces applied to the slave by the surgical environment. Additionally, while Cartesian coordinate mapping is preferred, the use of spherical, cylindrical, or other reference frames may provide at least some of the advantages of the invention.

Referring now to FIG. 16B, the control system of the robotic surgical system will now be described in greater detail. The control system in FIG. 16B is generally referenced by the reference number 1610. A feed forward control section 1675 of the control system 1610 is of interest in explaining how the slave end effectors are driven by the master. The remaining feedback portion of the control system 1610 may be only of interest if a force feedback is to be applied to the master. Typically a simplified biasing feedback is utilized to provide some tactile feedback to the operation of the system such that the feedback portion of the control system 1610 may not be implemented The master control 1650 has sensors, e.g., encoders, or potentiometers, or the like, associated therewith to enable the control system 1610 to determine the position of the master control 1650 in joint space as it is moved from one position to a next position on a continual basis during the course of performing a surgical procedure. In FIG. 16B, signals from these positional sensors are indicated by arrow 1614. Positional and velocity readings measured by the sensors 1687 are read by the input processing 1689 by the processor. It will be appreciated that since the master control 1650 includes a plurality of joints connecting one arm member thereof to the next, sufficient positional sensors are provided on the master 1650 to enable the angular position of each arm member relative to the arm member to which it is joined to be determined thereby to enable the position and orientation of the master frame on the master to be determined. As the angular positions of one arm member relative to the arm member to which it is joined is read cyclically by the processor 1689 in response to movements induced on the master control 1650 by the surgeon, the angular positions are continuously changing. The processor at 1689 reads these angular positions and computes the rate at which these angular positions are changing. Thus, the processor 1689 reads angular positions and computes the rate of angular change, or joint velocity, on a continual basis corresponding to the system processing cycle time, for example 1300 Hz. Joint position and joint velocity commands thus computed at 1689 are then input to the Forward Kinematics (FKIN) controller 1691.

At the FKIN controller 1691, the positions and velocities in joint space are transformed into corresponding positions and velocities in Cartesian space. The FKIN controller 1691 is a processor which typically employs a Jacobian (J) matrix to accomplish this. It will be appreciated that the Jacobian matrix transforms angular positions and velocities into corresponding positions and velocities in Cartesian space by means of conventional trigonometric relationships. Thus, corresponding positions and velocities in Cartesian space, or Cartesian velocity and position commands, are computed by the FKIN controller 1691.

The velocity and the position in Cartesian space is input into a scale and offset converter 1622. The velocity and the position in Cartesian space may also be input into a Cartesian controller 1620 if force feedback is to be provided.

The minimally invasive surgical apparatus provides for a scale change between master control input movement and responsive slave output movement. Thus, a scale can be selected where, for example, a 1-inch movement of the master control 1650 is transformed into a corresponding responsive ⅕-inch movement on the slave. At the scale and offset step 1622, the Cartesian position and velocity values are scaled in accordance with the scale selected to perform the surgical procedure. Naturally, if a scale of 1:1 has been selected, no change in scale is effected at 1622.

After a scale and offset step is performed at 1622, a resultant desired slave position and desired slave velocity in Cartesian space is input to a simulated or virtual domain at 1612, as indicated by arrows 1611. It will be appreciated that the labeling of the block 1612 as a simulated or virtual domain is for identification only and that the simulated control may be performed by elements outside of the functional block 1612.

The steps imposed on the desired slave velocity and position in the virtual domain 1612 are now generally described. A current slave position and velocity is continually monitored in the virtual or simulated domain 1612. The desired slave position and velocity is compared with the current slave position and velocity. Should the desired slave position and/or velocity as input from 1622 not cause transgression of limitations, e.g., velocity and/or position and/or singularity, and/or the like, as set in the virtual domain 1612, a similar Cartesian slave velocity and position is output from the virtual domain 1612 and input into an inverse scale and offset converter 1626. The similar velocity and position output in Cartesian space from the virtual domain 1612 is indicated by arrows 1613 and corresponds with actual commands in joint space output from the virtual domain 1612 as indicated by arrows 1615.

As mentioned, the control system 1610 enables limitations to be set in the simulation block 1612. These limitations can be chosen to conform with mechanical system limitations or constraints and/or can be preset to correspond with environmentally-sensitive movement limitations at the surgical site as will be described in greater detail herein. Thus, the limitations imposed in the simulated domain 1612, in one instance, can be regarded as virtual limitations corresponding with actual physical system limitations. The limitations at the simulated domain 1612 are not derived from actual slave movement but from simulated or virtual slave movement. Thus, the slave is prevented from actually transgressing a limitation by simulating its movement and velocity and restricting the simulated movement and velocity before instructing the actual slave to respond.

The resultant desired slave joint velocity and position signal from the simulated domain 1612 are passed to a joint controller 1648. At the joint controller 1648, the resultant or desired joint velocity and position signal are compared with the current actual joint position and velocity. The current actual joint position and velocity is derived through the sensors 1649 on the slave 1698 after having been processed by processor 1651 to yield slave current position and velocity in joint space.

The joint controller 1648 computes the torques desired on the slave motors to cause the slave to follow the resultant joint position and velocity signal taking its current actual joint position and velocity into account. The joint torques so determined are then routed to an output processor 1654. The joint torques may also be coupled to a feedback processor 1652, if available.

The joint torques are typically computed, by way of example, by means of the formula $\tau_J = K_p \underline{\Delta\theta}_p + K_v \underline{\Delta\theta}_v$ where $K_p$ is a spring constant, $K_v$ is a damping constant, $\underline{\Delta\theta}_v$ ("delta theta v") is the error or difference between the actual joint velocity input and the desired velocity input to the joint controller 1648, and $\underline{\Delta\theta}_p$ is the error or difference between the actual joint position input and the desired joint position input to the joint controller 1648.

The output processor 1654 determines the electrical currents to be supplied to the motors 1655 associated with the slave 1698 to yield the commanded torques and causes the currents to be supplied to the motors as indicated by arrow 1655.

As mentioned earlier, the slave indicated at 1698 is provided with a plurality of sensors. These sensors are typically operatively connected to pivotal joints on the robotic arm 153 and at the motors driving the robotic surgical tool. One or more sensors may be operatively coupled to joints or other elements of the robotic surgical tool or instrument 400.

These sensors are operatively linked to the processor at 1651. It will be appreciated that these sensors determine current slave position. Should the slave 1698 be subjected to an external force great enough to induce reactive movement on the slave 1698, the sensors will naturally detect such movement. Such an external force could originate from a variety of sources such as when the robotic arm 153 is accidentally knocked, or knocks into another robotic arm 153 or an endoscope arm, or the like.

As mentioned, the joint controller 1648 computes torques desired to cause the slave 1698 to follow the master 1650. An external force on the slave 1698 which causes its current position to vary also causes the desired slave movement to follow the master to vary. Thus a compounded joint torque is generated by the joint controller 1648, which torque includes the torque desired to move the slave to follow the master and the torque desired to compensate for the reactive motion induced on the slave by the external force. The torque generated by the joint controller 1648 may be routed to the feedback processor at 1652, if a force feedback system is to be provided.

End Effector Control for Maximizing Torque Drive

Referring now to FIG. 17, a block diagram of a master/slave servomechanism arrangement 1700 is illustrated for the actuation of the slave end effector 1756 in response to movement of the master grip members 1730 of the master control console 150. It should be understood that the various master and slave positions θ may comprise vectors (in Cartesian space, polar space, joint space, or the like) as well as simple angles or linear separations, and the kinematic chains of the master and slave may be quite different, often even having different degrees of freedom. The amount of following force applied by the operator on the slave are a function of a misalignment between a position (and orientation) of the master input device 1730 and a position (and orientation) of the slave end effector 1756. The master/slave servomechanism system 1700 relies on a biasing system 1760 that interacts with the operator's hand 1762 to provide tactile feedback to the operator with a feed forward system.

As illustrated schematically in FIG. 17, the master input device 1730 defines an actual master position $\theta_m^a$. The actual master position $\theta_m^a$ is transformed by a function f(.) and coupled into the slave portion of the bilateral controller as a desired slave position $\theta_s^d$. FIG. 20 illustrates exemplary curves 2001,2002 of the function f(.). The amount of force applied by the end effectors of the slave will vary with the difference between the desired position of the slave $\theta_s^d$ and the actual position of the slave $\theta_s^a$, with the following force on the end effectors increasing with increasing misalignment between the actual and desired positions, often with a proportional relationship.

It should be understood that the schematic representation provided in FIG. 17 of the servomechanism used to effect positional and orientational movement of the surgical end effector may appear quite different in its structural embodiment. For example, a single controller may be used to process both the master and slave signals. The controller can calculate error signals based on the difference between the actual and desired positions in space, and will generate servomotor torque controlling signals based on those error signals. As the master input controller and surgical end effector are moveable in a plurality of orientational and positional degrees of freedom, the calculation of these motor torques may involve vector coordinate transformations such as those described in more detail in U.S. Pat. No. 6,424,885, filed Aug. 13, 1999, the full disclosure of which was previously incorporated by reference.

In general, the actual configuration of the master and slave will be measured using potentiometers, encoders, or other position, velocity, and/or acceleration sensors affixed to rotational joints of the input control devices and slave manipulator. Position information may also be provided by encoders and/or potentiometers affixed to the set-up joints, which may include both rotational joints and linear sliding joints (particularly for the vertical axis). A variety of alternative configuration input mechanisms might be used, including stepper motors, optical configuration recognition systems (for example, using light emitting diodes mounted to the surgical tools and a CCD/frame grabber optical processing system coupled to the endoscope), and the like. It should also be understood that this direct master/slave arrangement will often provide uniform following forces throughout the range of motion of the master and/or slave, regardless of whether the following forces are applied using a system having a single degree of freedom, or a complex input control device and slave mechanism having six degrees of freedom for both the master and slave (optionally even including redundant degrees of freedom for the master and/or slave to avoid singularities).

Referring now to FIGS. 17, 18A-18B, and 20, the actual master position $\theta_m^a$ is transformed by a function f(.) to derive the desired slave position $\theta_s^d$ as discussed previously. Function f(.) takes the form $\theta_s^d = f(\theta_m^a)$, and is preferably an invertible (monotonic) and continuous function of the actual master position. The function f(.) may artificially increase (or in some cases, may decrease) the calculated error signal once the master grip separation drops below a predetermined point O (where the end effectors touch) to increase the grip strength (or decrease grip strength). This effectively increases (or decreases) the motor torque signals sent from the controller to the motors of the slave. Examples of when it may be desirable to decrease grip strength include the use of low strength delicate tools in which a very small misalignment can produce the maximum following force, so that there would be little tactile indication of grip without decreasing the slope of f.

In the embodiments of the present invention, it is desirable to increase the grip strength below the predetermined point O (the bumper point) to drive the maximum torque to the end effectors. When the tool 400 is mounted or increased grip strength is otherwise selected by a switch, the function f(.) is shifted from curve 2001 to curve 2002, for example, so that a greater movement in the slave end effectors can be requested through a larger desired slave position $\theta_s^d$ and the maximum torque can be applied to the slave end effectors.

Referring now again to FIGS. 17 and 20, once the separation between the gripping members drops below a predetermined bump point (arbitrarily indicated at the origin O in FIG. 20), a small reduction in gripping member separation $\theta_m^a$ results in a significantly larger change in the desired position of the slave $\theta_s^d$. The gripping member separation $\theta_m^a$ is reduced by squeezing the master grips 350A-350B together. Above the predetermined bumper point O, the actual master position and desired slave position can remain the same, thereby providing the greatest dexterity for the system operator's control over the end effector.

Referring now to FIGS. 20 and 21A-21B, the predetermined force enhancement initiation point O is determined by the configuration of handle 325 and the biasing system 1760. Similarly, the fully closed or "slammed" configuration of the handle at point P on the curve may be determined by a stop of the handle 325. The lateral position (corresponding to $\theta_m^a$) of point O will preferably remain unchanged for a variety of different end effectors when different tools are attached to a surgical robotic system. However, as noted above, the actual strengths and intended maximum forces of these different tools may be significantly different.

To allow the control system to drive to maximum joint torque, the processor may revise the function f(.) of the servomechanism. The function f(.) may be selectively revised from curve 2001 where the maximum force position is point P to curve 2002 where the maximum force position is at point P'. This allows the servomechanism to adapt to the tool 400 and achieve maximum torque (essentially unlimited by position) while other tools are driven to a position and potentially never reach the maximum torque limits. When tools are changed, the servomechanism can adapt its control system without having to revise the mechanical configuration of the master controller.

The tool 400 can make use of a memory device or other circuit with memory (referred to herein as "tool memory") mounted in the tool to instruct the master controller to adapt its servomechanism to drive to maximum torque or alternatively a switch may be used to do so. The tool memory can also provide a signal verifying that the tool is compatible with that particular robotic system. The tool memory may also identify the tool-type (whether it is a scalpel, needle grasper, jaws, scissors, clip applier, electrocartery blade, electro-surgical grippers or the like) to the robotic system so that the robotic system can reconfigure its programming to take full advantage of the tools specialized capabilities.

It will be recognized that a wide variety of functions f(.) may be applied to enhance grip strength at the end effectors 812A-812B. In the exemplary embodiment illustrated by curves 2001,2002, function f(.) comprises a linear function directly connecting the maximum force/slam point P or P' with the predetermined force enhancement position O. This allows directly proportional control over the following forces of the slave, and can be substantially reproduced by a biasing system 1760 to provide accurate tactile feedback. Alternatively, more complicated functions might be used. Preferably, the function will be continuous so as to avoid "jumps" in gripping force at the end effectors. Function f(.) will preferably be monotonic and invertible, particularly where force feedback is to be effected using a reciprocal master/slave system, as described above.

To accurately model the forces applied by the end effectors, it should be recognized that the slave position will often be measured remotely (at the motor/sensor location), rather than at the end effector joint. Hence, the compliance of the system will reflect the compliance of a portion of the transmission system. This can be accommodated using the formula $F_s=\theta_s^d (K_{servo}*K_{mech})/(K_{servo}+K_{mech})$ where $F_s$ is the end effector gripping force, $K_{servo}$ is the effective spring constant of the motor, and $K_{mech}$ is the spring constant of the mechanical transmission elements. This equation of $F_s$ may allow the robotic system to mimic the stiffness of a particular tool when master grip separation is at a minimum. Surgical tools often flex when fully squeezed. By properly compensating for the spring constant of the motor and mechanical transmission elements, the overall servomechanism can transition from a relationship determined from servomechanism design considerations (when wide open) to a surgical tool-like relationship (when clamped closed).

Referring now to FIGS. 18A-18B, simplified functional block diagrams of servomechanisms 1800A-1800B for driving the end effectors to maximum torque with one servomotor or two servomotors is illustrated. The signal processing used to provide the enhanced grip following forces at the end effectors described above is also illustrated in greater detail in FIGS. 18A-18B.

The servomechanisms 1800A-1800B each include a position derivative (PD) controller 1801, a torque saturation limiter 1812, and a torque differential coupler 1814,1814' coupled together as shown. The torque differential coupler 1814 includes a coupling matrix that may vary with the type of robotic surgical tool 400 that is attached to the robotic surgical arm 153. To drive a pair of end effectors with a single motor 1870, the servomechanism 1800A further includes a torque to current converter 1816 and a current limiter 1818 coupled together as shown. To drive a pair of end effectors with a pair of motors 1870A-1870B, the servomechanism 1800B further includes a first torque to current converter 1816A and a first current limiter 1818A coupled together in series to the motor 1870A and a second torque to current converter 1816B and a second current limiter 1818B coupled together in series to the motor 1870B.

From the master, the actual master grip separation $\theta_m^a$ and the actual master grip velocity $v_m^a$ of the master grip members 350A-350B are coupled into the PD controller 1801. From the slave, the actual slave separation $\theta_s^a$ and the actual slave velocity $v_s^a$ of the end effectors are coupled into the PD controller 1801.

One or more sensors 1866, 1868 measure the handle separation $\theta_m$ by sensing the distance between the master grip member 350A and the master grip member 350B to generate the actual master grip separation $\theta_m^a$. The one or more sensors 1866, 1868 may also measure the velocity $v_m$ as the master grip members 350A-350B are squeezed closed and released to open to generate a measure of the actual master grip velocity $v_m^a$. The handle 325 may include a stop 1864 to sense the fully closed or "slammed" configuration of the master grips 350A-350B and determine point P on a curve. The handle 325 may additionally include a biasing structure 1860 to provide tactile feedback to a user. The biasing structure 1860 may include a bushing, one or more springs, etc.

The actual master grip separation $\theta_m^a$ is processed using the function f(.) 1804A to provide the desired slave separation $\theta_s^d$ as described above. The actual master grip velocity $v_m^a$ may also be modified according to the function f(.) 1804B to generate the desired slave velocity $v_s^d$.

The actual slave separation $\theta_s^a$ of the end effectors is measured by one or more sensors 1806A, such as an encoder or potentiometer of the motor 1870. The actual slave velocity $v_s^a$ of the end effectors may also be measured by one or more sensors 1806B, such as a tachometer sensing the velocity of the shaft of the motor 1870. For the two motors 1870A-1870B of FIG. 18B, a plurality of sensors 1806A, 1806B are used at each motor and combined to determine the actual slave separation $\theta_s^a$ of the end effectors and the actual slave velocity $v_s^a$ of the end effectors opening and closing.

The actual slave separation $\theta_s^a$ of the end effectors is subtracted from the desired slave separation $\theta_s^d$ by the subtractor or negative summer 1808A to provide a position error signal $e^s$. The actual slave velocity $v_s^a$ of the end effectors is subtracted from the desired slave velocity $v_s^d$ by the subtractor or negative summer 1808B to provide a velocity error signal $e^{s\prime}$.

The position error signal $e^s$ and velocity error signal $e^{s\prime}$ are respectively amplified by associated gain factors, $K_p$, and $K_v$ by the amplifiers 1802A-1802B. The amplified position error signal $K_p e^s$ and the amplified velocity error signal $K_v e^{s\prime}$ are added together by the summer 1810 to generate an unbounded joint torque signal $\tau_j$ ("tau sub j").

The unbounded joint torque $\tau_j$ generated by the PD controller can be expressed by the equation $\tau_j = K_p e^s + K_v e^{s\prime}$. To increase or decrease grip strength and the joint torque, the gain factors $K_p$, and $K_v$ of the amplifier can be varied. To drive the end effectors to maximum torque, the gain factor $K_p$ (such as for curve 2001 in FIG. 20) was replaced with the increased gain factor $K_{p\prime}$ (such as for curve 2002 in FIG. 20) in one embodiment of the invention.

With the increase in the gain provided by the gain factor $K_{p\prime}$, the unbounded joint torque needs to be limited to the maximum joint torque values. The unbounded joint torque $\tau_j$ is coupled into the torque saturation limiter 1812 to generate a bounded joint torque signal $\tau_j\prime$ bounded by an upper torque limit (UTL) and a lower torque limit (LTL).

Referring now momentarily to FIG. 19, the function of the torque saturation limiter 1812 is illustrated by a curve. If the unbounded joint torque signal $\tau_j$ is below the LTL, it is clipped to the LTL level and output as the bounded joint torque signal $\tau_j\prime$. If the unbounded joint torque signal $\tau_j$ is above the UTL, it is clipped to the UTL level and output as the bounded joint torque signal $\tau_j\prime$. Between the UTL and the LTL, the joint torque signal $\tau_j$ is passed through the torque saturation limiter 1812 as the bounded joint torque signal $\tau_j\prime$.

Referring now back to FIGS. 18A-18B, the bounded joint torque signal $\tau_j\prime$ is output from the torque saturation limiter 1812 and coupled into the torque differential coupler 1814, 1814'.

The torque differential coupler 1814,1814' is a coupling matrix to transform joint torque into motor torque. The torque differential coupler 1814,1814' considers the drive mechanics (e.g., drive pulleys, actuating spools, etc.) of the robotic surgical arm 153 and the robotic surgical tool 400 in transforming the joint torque signal $\tau_j\prime$ into a motor torque signal $\tau_M$ so that the desired joint torque appears at the end effectors. Thus, it is expected that the coupling matrix of the torque differential coupler 1814,1814' will vary over the different types of robotic surgical tools being used.

For example, the coupling matrix of the torque differential coupler 1814 for the one motor 1870 illustrated in FIG. 18A will be different from the coupling matrix of the torque differential coupler 1814' for the two motors 1870A-1870B illustrated in FIG. 18B. The coupling matrix of the torque differential coupler 1814' generates two motor torque signals $\tau_{M1}$ and $\tau_{M2}$ for the two motors 1870A-1870B illustrated in FIG. 18B. The coupling matrix of the torque differential coupler 1814 generates a single motor torque signal $\tau_M$ for the motor 1870. The motor torque signal $\tau_M$ and the two motor torque signals $\tau_{M1}$ and $\tau_{M2}$ may exceed the capabilities of the motors 1870, 1870A-1870B, if not for the current limiters 1818A-1818B.

Referring now to FIG. 18A, the motor torque signal $\tau_M$ from the torque differential coupler 1814 is coupled into the torque to current converter 1816. The torque to current converter 1816 divides the motor torque signal $\tau_M$ by a torque constant $K_\tau$ to generate a motor current $I_m$. The motor current $I_m$ is coupled into the current limiter 1818.

The current limiter 1818 limits the motor current $I_m$ that it receives to a motor current $I_m\prime$ to a level below a maximum current limit (MCL) to avoid overheating and damaging the servomotor 1870 from excess current levels. The motor current $I_m\prime$ is coupled to the motor 1870 to produce a torque in its shaft and drive a rotatable driver and an end effector by means of a cable drive system discussed previously with respect to FIGS. 8-11.

Referring now to FIG. 18B, the motor torque signals $\tau_{M1}$ and $\tau_{M2}$ from the torque differential coupler 1814' are respectively coupled into the torque to current converters 1816A-1816B.

The torque to current converter 1816A divides the motor torque signal $\tau_{M1}$ by a torque constant $K_\tau$ to generate a motor current $I_{m1}$. The torque to current converter 1816B divides the motor torque signal $\tau_{M2}$ by a torque constant $K_\tau$ to generate a motor current $I_{m2}$. The motor current $I_{m1}$ from the torque to current converter 1816A is coupled into the current limiter 1818A. The motor current $I_{m2}$ from the torque to current converter 1816B is coupled into the current limiter 1818B.

The current limiters 1818A-1818B respectively limit the motor currents $I_{m1}$ and $I_{m2}$ that they receive to motor currents $I_{m1}\prime$ and $I_{m2}\prime$ below a maximum current limit (MCL) to avoid overheating and damaging the servomotors 1870A-1870B from excess current levels.

The motor current $I_{m1}\prime$ is coupled to the motor 1870A to produce a torque in its shaft and drive a rotatable driver pulley 828A and an end effector 812A by means of a cable drive system discussed previously with respect to FIGS. 8-11. The bounded motor current $I_{m2}\prime$ is coupled to the motor 1870B to produce a torque in its shaft and drive a rotatable driver 828B and an end effector 812B by means of a cable drive system discussed previously with respect to FIGS. 8-11. In this manner two motors are energized to provide following grip forces for each end effector 812A,812B.

As noted previously, FIGS. 18A-18B are simplified block diagrams of the servomechanism control systems for two differing types of robotic surgical tools. The functional blocks of the control systems may be implemented by software routines executing in the computer system 151 of the master console. The signals in this case may be digital signals or vectors that may eventually be converted into analog signals by a digital to analog converter (DAC) such as at the motors. Exemplary software subroutines to execute the functions of the functional blocks of the control systems are described in detail in and shown by FIGS. 13A-13C of U.S. Pat. No. 6,594,552, entitled "Grip Strength with Tactile Feedback for Robotic Surgery", filed by Nowlin et al on Apr. 6, 2000 which has been previously incorporated by reference.

The control systems 1800A-1800B use velocity and velocity error signals which may help inhibit excessive cycling of the system as the slave attempts to follow the master. Hence, these velocity signals represent a viscosity of the system. However, their use may not be necessary, particularly for effecting grip, in light of the small masses and high friction and grip forces that are involved.

Furthermore, while position and velocity error signals were used to compute an unbounded joint torque to compare against upper and lower limits, the use of a torque or force sensor at the motors or the end effectors of the slave mechanism may better enable the measurement, and hence control, of the force applied by the slave to tissue. Additionally, the use of force sensor at the grip element of the master manipulator may enable the measurement, and hence command to the slave, of the force being applied by the operator on the handle.

Methods of Operation for Maximum Torque Drive

The robotic surgical tool is operated to ensure that a consistent gripping force is attained throughout life of instrument by driving its end effectors to maximum torque limits instead of positional limits.

The end effectors 812A-812B of the electro surgical instrument 400 may be controlled by the operator O seated at the robotic surgical master control console 150 in a number of ways. Typically a gripping or squeezing motion ("master grip") on the master grips 350A-350B of the touch sensitive handle 325 by an operators hand 62 may be used to close the jaws or end effectors 812A-812B of the robotic surgical instruments 400 around tissue. Upon release of the master grips 350A-350B of the touch sensitive handle 325, the jaws or end effectors 812A-812B open up and reduce the force applied to tissue.

FIG. 21A illustrates end effectors 812A-812B just engaging a suture S but not yet applying significant forces against the suture. As the cross-sectional thickness of suture S is quite small, the separation between the end effector elements is effectively zero. As no forces are being imposed by the servomechanism, the grip separation angle of handle 325 is also substantially equal to zero. Note that the grip elements need not exactly define a zero angle. At this nominal position, grip elements 350A and 350B are just beginning to engage a biasing mechanism 1860A of a biasing system 1860. Biasing mechanism 1860A is here illustrated as an elastomeric bushing surrounding a grip return spring 1860B. A variety of biasing structures might be used in place of biasing mechanism 1860A, including springs, magnets, or the like. The biasing mechanism may define a predetermined biasing transition point.

Referring now FIG. 22A, the force $F_{master}$ applied to the master increases at a predetermined master separation point O'. This biasing system transition point will preferably occur just as the end effector elements touch, and will thereby indicate to the operator the enhanced grip strength being applied by the servomechanism.

Referring now to FIG. 22B, the end effector grip force $F_{slave}$ is illustrated for the corresponding grip actuation by the master as illustrated in FIG. 22A, when gripping an object of negligible thickness. Initially there is little end effector grip force $F_{slave}$ up until the bump point O where the end effector grip force $F_{slave}$ increases in response to the slave demand generated by the master.

Referring now to FIG. 21B, an operator's hand 2162 can squeeze handle 325 beyond the nominal zero angle by compressing bushing 1860A between the grip members. Once the operator squeezes the handle sufficiently to engage stops 1864 of the grip members, end effectors 812A-812B will preferably be imposing the maximum joint torque at the end effectors and the maximum following force $F_m$ against suture S. This maximum gripping force configuration is designated by the point P' along function f(.) illustrated by the curves 2002 in FIG. 20A. Advantageously, the reactive forces provided by bushing 1860A against operator's hand 2162 provide tactile feedback to the operator of the enhanced following forces below the predetermined position O. As described above, function f(.) preferably comprises the identity function above the predetermined position O. It should be understood that the predetermined position O need not define any actual dimensions or forces.

Referring now to FIG. 23, a flow chart of robotic surgical system setup for a robotic surgical instrument to drive its end effectors to maximum torque limits is illustrated. The method of system setup begins at the start 2300.

At block 2302, the robotic surgical instrument or tool 400 is mounted to a robotic surgical arm 153. The method then goes to block 2304.

At block 2304, a memory in the robotic surgical instrument or tool 400 is read out to determine the tool type and to determine if any control system adjustments are to be made to control the cable drive system. The memory may include the upper torque limit and the lower torque limit settings or the tool type may provide an address to the system for looking up the maximum torque limits. The memory may include information regarding the coupling table that is used to transform torque into current or provide an address to the system to where the information in the coupling table can be found. After reading the memory, the method then goes to block 2306.

At block 2306, the control system of the robotic surgical system is adjusted to drive a first end effector to a torque in a range between an upper torque limit and a lower torque limit in the case of a single end effector. In the case of two end effectors, the control system may be adjusted to concurrently drive a first end effector and a second end effector to a torque in the range between the upper torque limit and the lower torque limit. In any case, the torque may be a desired joint torque at the pivot pin of the first end effector and the second end effector. An unbounded desired joint torque at the end effectors is bounded to drive servomotors between maximum torque settings. The equation used to generate the unbounded desired torque value is adjusted to saturate more quickly when the touch sensitive grips of the master console are squeezed more tightly around tissue. After the control system adjustments are completed, the method then goes to block 2308.

At block 2308, the robotic surgical instrument or tool 400 is operated by the robotic surgical arm 153. In the case of a single end effector, the first end effector is driven to the torque in the range limited by the upper torque limit and the lower torque limit. The drive pulley to which the end effector is attached is driven to the torque in the limited range of torque. In the case of two end effectors, the first end effector and the second end effector are concurrently driven to the torque in the limited range. The drive pulleys to which the end effectors are attached are driven to the torque in the limited range of torque.

After the end effectors are driven and the robotic surgical procedure is completed, the method goes to block 2399 and ends.

During surgical procedures, such as when sealing vessels, the maximum gripping force at the jaws of the end effectors (torque at the input disks) should be achievable throughout the life of an instrument to ensure consistent vessel sealing by adjusting the controls system to drive to maximum torque levels regardless of cable stretch. Driving to maximum torque levels assures that tissue is clamped with a high grip force for various surgical procedures. One such procedure may be to seal tissue closed. In this case, a bipolar electrosurgical robotic tool may be used with a bipolar generator. The maximum torque levels may be automatically set by the mounting of the tool to a robotic surgical arm or they may be selectively set by an independent switch such as a push button switch or a dependent switch such that the higher grip forces are activated with the bipolar generator.

Referring now to the flow chart of FIG. 24, an exemplary operation of the robotic surgical system with the capability of driving end effectors to maximum torque is now described. The method starts at block 2400 and goes to block 2402.

At block 2402, the robotic surgical instrument coupled to the robotic surgical arm is calibrated prior to a robotic surgical procedure. During such calibration or initialization, a pair of end effectors may be driven to determine a bump point. The bump point is the position of the input disks where a first end effector and a second end effector just close together and touch each other with substantially zero force. This is the point where the torque is applied to apply a force at the tips of the end effectors. After calibration, the method goes to block 2404.

At block 2404, the grips of the touch sensitive handle are first squeezed to close the first end effector and the second end effector around tissue without applying significant force to the tissue. After closing around the tissue the method goes to block 2406.

At block 2406, the grips of the touch sensitive handle are squeezed further to apply additional torque to the first end effector and the second end effector to apply a tip force to the tissue. If a vessel, the vessel may begin to close by the tip force. After starting to apply the tip force, the method goes to block 2408.

At block 2408, the maximum torque is applied to the first end effector and the second end effector to generate a maximum tip force to squeeze tightly around the tissue regardless of any cable stretch in the cables of the robotic surgical instrument. After squeezing tightly on the tissue, the method may go to block 2410 if an electro-surgical instrument is being used. If the robotic surgical tool is not an electro-surgical instrument, block 2410 is skipped and the method jumps to block 2412.

At block 2410, assuming the robotic surgical tool is an electro-surgical instrument and maximum torque has been applied, electrical energy is supplied to one or both of the first end effector and the second end effector. If supplied to both, a bipolar generator is utilized with the bipolar electro-surgical tool. If supplied to one end effector, a mono-polar generator is utilized with the mono-polar electro-surgical tool. The electrical energy may be supplied to cauterize tissue or to seal tissue closed. The amount of electrical energy supplied may be a function of the impedance of the tissue, the clamping force applied to the tissue by the end effectors, and the time that the electrical energy is to be supplied to the end effectors. After supplying the electrical energy, the method goes to block 2412.

At block 2412, a determination is made as to whether or not the grips have been released to reduce the torque at the first end effector and the second end effector. If the grips have not been released but are maintained closed, then the maximum torque is maintained by looping back around to block 2408 where the application of the maximum torque is repeated. If the grips have been released, the method goes to block 2414.

At block 2414, the grips have been released and the torque applied to the first end effector and the second end effector is reduced and the method may go to block 2499 and end. Alternatively, the portions of the method after calibration may repeat itself over and over again until the robotic surgery is completed.

While the mounting of the tool is discussed as changing the software settings for torque limited control of the servomotors, the torque limited control of the robotic surgical tool may be selectively enabled by a switch. For example a separate actuator, such as a foot pedal, may be pressed to enable the torque limited control and increase the grip force to apply maximum torque to the end effectors. Alternatively, a button, toggle switch, or momentary switch may be used to toggle between a normal mode of driving the end effectors and a torque limited mode of driving the end effectors.

Locking Mode for Robotic Surgical Tools

Referring now momentarily to FIG. 4A, during a surgical procedure, the wrist 402 and/or one or more end effectors 414A-414B of the robotic surgical tool 400 may be locked so that movement is constrained. Locking the wrist 402 of the robotic surgical tool may avoid cable overstress and cable breakage when applying a maximum torque to end effectors. Locking or clamping the end effectors 414A-414B allows them to be clamped and ratcheted down around tissue. Once the end effectors are locked or clamped in position, a surgeon may let go of the control input while the robotic surgical system 100 maintains the gripping or clamping force. The robotic surgical system may 100 enter a lock mode so that a surgeon may easily selectively lock and unlock the wrist 402 and end effectors 414A-414B. The robotic surgical system 100 may also exit the lock mode to return the robotic surgical tool 400 to its normal range of motion and degrees of freedom.

In some configurations to achieve a higher torque at the end effectors 414A-414B, less torque is to be applied at the wrist axes to prevent mechanical failure in the grip cables coupled to the end effectors. The lower torque at the wrist axes is achieved by locking the wrist 402 of the robotic surgical tool 400. Locking the wrist 402 locks the joint orientation degrees of freedom (roll, pitch, and yaw) in the robotic surgical tool. The translation degrees of freedom in the robotic surgical tool 400 is maintained to still allow intuitive control by a surgeon. The end effectors 414A-414B of the robotic surgical tool may also be locked so that a surgeon can perform other tasks with other tools. While the wrist 402 and/or the end effectors 414A-414B of the robotic surgical tool 400 may be locked, the shaft 416 may be free to rotate or linear translate along its axis 450. Thus, a surgeon may clamp onto tissue with the end effectors 414A-414B in a locked position and then pull or rotate the tissue out of the way, for example. While the locking feature on the grip axis reduces dexterity, it also can reduce surgeon fatigue during certain operations, such as tissue sealing, and ensures continuity of the grip force, such as during a tissue sealing procedure. Moreover locking the wrist 402 of the robotic surgical tool 400 limits the maximum applied torque on the wrist cables (e.g., CL3 in FIG. 8) so that a maximum torque may be applied to the end effectors and its grip cables (e.g., CL1 and CL2 in FIG. 8) without failure, Referring momentarily to FIGS. 2B, 3B, and 4A, in one implementation of the robotic surgical system in the lock or reduced dexterity mode, the outer yaw 215B, outer pitch 215A, and insertion axes 215C,257 of the robotic surgical arm 158 are still free to follow the control input wrists 352 (see FIG. 3B) while the roll 450 (see FIG. 4A), inner pitch A1, and inner yaw (A2) axes are locked at their mode-entry position. In this manner, a surgeon is still able to move the tip of the robotic surgical tool 400 in the X, Y, and Z directions and control the grip, but is not able to rotate the orientation of the instrument wrist 402.

The master control console provides feedback to a surgeon when the robotic surgical system is in a lock sensing mode and in a locked mode. When entering the lock sensing mode, an audible beep is generated at the surgeons console and a first icon is placed in the field of view of the stereo display at the surgeon's console. When entering the locked mode, a second icon is placed in the field of view of the stereo display at the surgeon's console. Alternatively, when entering the lock sensing mode, a flashing icon is displayed and when entering the locked mode the icon becomes solidly displayed, When exiting the respective mode, the respective icons are removed from the display or the icon switches from being solid to flashing. The disabled degrees of freedom (roll 450 (see FIG. 4A), inner pitch A1, and inner yaw (A2) axes) are dynamically mapped through a Cartesian transformation back to the control input wrists 352 as a virtual "no-entry" surface, may intuitively provide force feedback to the surgeon at the master about available paths of motion of the robotic surgical tool. That is, the master only allows certain paths of motion so that the wrist does not move.

Referring now to FIG. 8, the degrees of freedom (roll 450 (see FIG. 4A), inner pitch A1, and inner yaw (A2) axes) are disabled to avoid failure of the coupled transmission (e.g., CL1,CL2,CL3) between the respective driven elements 818A-818C and the instrument wrist axes A1,A2. The cables CL1, CL2 that transmit grip torque are the same cables that transmit yaw torque from the robotic surgical arm motors 802A-802B to yaw the tip of the robotic surgical tool. With the wrist locked in the lock mode, the commanded yaw position of the tip of the robotic surgical tool is not allowed to move in order to prevent cable failure due to excessive force. Thus, the yaw grip cables CL1,CL2 transmit grip torque to the end effectors 812A-812B in lock mode. The torque budget allotted to the yaw axis is substantially reduced to zero to allow for more grip torque for high-grip torque clinical applications, such as vessel sealing. The inner roll and pitch motion of the tip of the robotic surgical tool are not allowed to move as well in the lock mode (a.k.a., reduced dexterity mode) to maintain intuitiveness of the control, even though roll and pitch joint torques are not coupled to the grip cables CL1,CL2 and would not facilitate their failure.

The double-click user interface 2701 is a seamless user interface for switching between the locked mode (a.k.a., reduced dexterity mode) and the normal unlocked mode (a.k.a., full dexterity mode). With dual dexterity modes for the same instrument, the need for an instrument exchange is unnecessary since the same instrument can then be used both for sealing (reduced dexterity mode and high grip strength/ max torque) and dissection/manipulation (full dexterity and nominal grip strength).

In order to switch modes, the surgeon quickly closes the grips 350A-350B twice (double click signature) from the open position within a double click time. The double click time is measured by software against and compared to a lock mode threshold time. If the double click time is less than or equal to the lock mode threshold time, an intentional mode change between a locked mode and normal unlocked mode is deemed to occur. Otherwise if the double click time is greater than the lock mode threshold time, the double click is discarded as a false-positive mode change request. In one implementation, the lock mode threshold time is one half (0.5) second.

While in a locked mode (reduced dexterity mode), another aspect of the double-click user interface 2701 involves ratcheting, latching, or locking the grip of one or more end effectors closed and increasing the torque applied to the end effectors. A surgeon can manipulate the end effectors around a vessel to be sealed and apply a large grip command to lock the grip of one or more end effectors clamped around the vessel. The surgeon can then relax his hand while the instrument grip remains continuously closed around the vessel until sealing is completed. Electrical energy may be applied to the end effectors to seal the vessel.

After the grip is locked, if the surgeon moves the master grip again to generate a grip command exceeding the lock grip threshold, the end effectors are unlatched or unlocked. The double-click user interface may be disabled while the grip axis is latched or locked. The disabling of the double-click user interface may avoid accidentally opening the end-effectors around the grip axis or rotating the instrument wrist during vessel sealing.

Referring now to FIG. 27, a user interface system 2700 including a double-click user interface 2701 may be provided in a robotic surgical system to allow a surgeon to quickly enter and exit locking modes without an additional button or foot pedal to press. The double click user interface 2701 allows a surgeon to quickly switch between a reduced dexterity mode (also referred to as a sealing or lock sensing mode), and a full dexterity mode (also referred to as a dissection/manipulation or normal mode) with a simple double-click of the master grips 350A-350B of the touch sensitive handle 325.

The double click user interface 2701 may be implemented in software for execution by a computer (e.g., computer 151 in FIG. 3A). The double click user interface 2701 includes a double click sensing process 2710, a hard stop sensing process 2711, and a lock mode state machine 2712 operationally in communication together as illustrated. Optionally, a robotic surgical system may include a mode selection switch 2702 in addition to or instead of the double click sensing process 2710. The mode selection switch 2702 may be provided by a button or foot peddle at the master control station. The actual master position $\theta_m^a$ of the master grips 350A-350B is received by the double click user interface 2700 and analyzed by the double click sensing process 2710 and the hard stop sensing process 2711.

The double click sensing process 2710 analyzes the actual master position $\theta_m^a$ to detect two closure or grip cycles (a double-click) of opening and closing of the master grips 350A-350B by a surgeon within a predetermined period of time T. The predetermined period of time T may be selected to be a short time period to distinguish from normal opening and closing of the master grips. For example, assume grips 350A-350B are open having an initial open angle $\theta_{m1o}$. Within the predetermined period of time, grips 350A-350B are closed to a first closed angle $\theta_{m1c}$, opened to a first open angle $\theta_{m2o}$, closed to a second closed angle $\theta_{m2c}$ and opened again to a second open angle $\theta_{m3o}$. Graphically, within the predetermined period of time T, the actual master position $\theta_m^a$ may travel twice along the exemplary curves 2001, 2002 in the upper-right quadrant of the function f(.) illustrated in FIG. 20. If a double-click is sensed, the robotic surgical system changes from a normal mode to a lock sensing mode.

The hard stop sensing process 2711 analyzes the master position $\theta_m^a$ to detect if the movement or closure of the master grips 350A-350B by a surgeon meets or exceeds a predetermined percentage of a hard stop. Hard stops may occur after the biasing mechanism 1860A is engaged and the bump point O has been reached. Graphically, the actual master position $\theta_m^a$ may travel along the exemplary curves 2001,2002 in the lower-left quadrant of the function f(.) between point O and point P illustrated in FIG. 20.

The first hard stop may be a first percentage (e.g., ninety percent) of the angle $\theta_m^a$ at the fully closed or "slammed" configuration of the handle at point P illustrated in FIG. 20. If in the lock sensing mode and the first hard stop is sensed, the wrist 402 is locked and the end effectors 414A-414B are locked. The hard stop sensing process 2711 continues to analyze the master position $\theta_m^a$ of the grips for a second hard stop. Once in a lock mode, the end effectors 414A-414B may be ratcheted further together from the first hard stop up until the second hard stop in one implementation. The second hard stop may be a second percentage (e.g., ninety-five percent) of the angle $\theta_m^a$ at the fully closed or "slammed" configuration of the handle at point P. The second percentage and the first percentage may differ or be the same. If the first hard stop and the second hard stop are sensed in the same close action of the master grips, the first hard stop is controlling to lock the wrist and the end effectors. If the second hard stop is sensed in a different close action of the master grips when the wrist and end effectors are locked, the wrist and the end effectors are unlocked and the robotic surgical system returns to a lock sensing mode.

The optional mode selection switch 2702, when activated, alternatively signals the lock mode state machine 2712 to enter the lock mode to reduce the number of degrees of freedom in the robotic surgical instrument.

As illustrated in FIG. 27, the modes/states of the lock mode state machine 2712 are coupled to the controller(s) of the slave end effectors and the wrist to respectively control the locking and unlocking of the end effectors and the wrist of the robotic surgical tool.

Referring now to FIG. 25A, modes/states of the lock mode state machine 2712 are illustrated for one configuration. In a normal mode/state 2501, the wrist and the end effectors are unlocked and operated normally with the robotic surgical tool having all available degrees of freedom. If a double click 2511A is sensed by the double clicking sensing process 2710, the lock mode state machine 2712 changes from a normal mode/state 2501 to a lock sensing mode/state 2502. If no double click is sensed, the lock mode state machine 2712 remains in the normal mode/state 2501 and continues the double click sensing process as illustrated by return arrow 2510.

In the lock sensing mode/state 2502 if a hard stop 2514A is sensed by the hard stop sensing process 2711, the lock mode state machine 2712 switches or changes from a lock sensing mode/state 2502 to a lock mode/state 2503. If no hard stop is sensed, the lock mode state machine 2712 remains in the lock sensing mode/state 2502 and continues the hard stop sensing process as illustrated by return arrow 2512. In the lock mode/state 2503, both the wrist 402 and the end effectors 414A-414B may be locked in one implementation. That is, in the lock mode/state the lock mode state machine 2712 switchably reduces the number of degrees of freedom in the robotic surgical tool in response to the detection of a double click in the master grips and a hard stop in the movement of the control input mechanism. In the lock mode/state, the lock mode state machine further switchably holds a gripping force of one or more end effectors of the robotic surgical tool in response to the detection of a hard stop in the movement of the master grips. If another hard stop is detected in the movement of the master grips, the lock mode state machine releases a constant gripping force of one or more end effectors.

If in the lock mode/state 2503 the second hard stop 2514B is sensed by the hard stop sensing process 2711, the lock mode state machine switches or changes back to the lock sensing mode/state 2502 and the wrist 402 and the end effectors 414A-414B are both unlocked in one implementation. If no second hard stop 2514B is sensed, the lock mode state machine 2712 remains in the lock mode/state 2503 and continues the hard stop sensing process as illustrated by return arrow 2513.

If in the lock sensing mode/state 2502 a double click 2511B is sensed by the double clicking sensing process 2710, the lock mode state machine 2712 changes back from the lock sensing mode/state 2502 to the normal mode/state 2501. In the normal mode/state 2501, the lock mode state machine 2712 continues the double click sensing process as illustrated by return arrow 2510.

Referring now to FIG. 25B, modes/states of the lock mode state machine 2712 are illustrated for another configuration. In a normal mode/state 2520, the wrist is unlocked and operated normally with the robotic surgical tool having all available degrees of freedom. If a double click 2521A is sensed by the double clicking sensing process 2710, the lock mode state machine 2712 changes from a normal mode/state 2520 to a locked wrist mode/state 2523. If no double click is sensed, the lock mode state machine 2712 remains in the normal mode/state 2520 and continues the double click sensing process as illustrated by return arrow 2522.

If in the locked wrist mode/state 2523 and a double click 2521B is sensed by the double clicking sensing process 2710, the lock mode state machine 2712 changes from the locked wrist mode/state 2523 to the normal mode/state 2520. If in the locked wrist mode/state 2523 and no double click is sensed by the double clicking sensing process 2710, the lock mode state machine 2712 remains in the locked wrist mode/state 2523 and continues the double click sensing process as illustrated by return arrow 2524.

If in normal unlocked mode (full dexterity), a double-click signature within the lock mode threshold time causes the robotic system to enter the reduced dexterity mode (lock mode) for the respective robotic surgical tool. Another double-click signature within the lock mode threshold time causes the robotic system to exit the reduced dexterity mode and go back to the full dexterity mode. The surgeon, in this manner, can easily switch back and forth between a sealing procedure and a dissection procedure.

Referring now to FIG. 25C, modes/states of the lock mode state machine 2712 are illustrated for another configuration. In a normal mode/state 2530, the grip/end effectors are unlocked and operated normally with the robotic surgical tool having all available degrees of freedom. If a full hard stop 2534A is sensed by the hard stop sensing process 2711, the lock mode state machine 2712 changes from a normal mode/state 2530 to a locked grip mode/state 2535. If no hard stop is sensed, the lock mode state machine 2712 remains in the normal mode/state 2530 and continues the hard stop sensing process as illustrated by return arrow 2531.

If in the locked grip mode/state 2535 and a hard stop 2534B is sensed by the hard stop sensing process 2711, the lock mode state machine 2712 changes from the locked grip mode/state 2535 to the normal mode/state 2530. If in the locked grip mode/state 2535 and no hard stop is sensed by the hard stop sensing process 2711, the lock mode state machine 2712 remains in the locked grip mode/state 2535 and continues the hard stop sensing process as illustrated by return arrow 2536.

Alternate Tool Mode

While a lock sensing mode and a lock mode have been described herein, the user interface of the robotic surgical system may instead respectively provide an alternate tool sensing mode and an alternate tool mode. The functionality of the alternate tool mode may be programmed in response to the type of tool coupled to the robotic surgical system. The alternate tool sensing mode and the alternate tool mode may be entered in various ways through sensing alternate user inputs. The alternate user inputs to initiate the alternate sensing mode and/or alternate tool mode may not be normally sensed or looked for during normal tool operation. The state machine 2712 may be modified to enter the alternate sensing mode and/or alternate tool mode in response to one or more alternate user inputs.

Referring now to FIG. 25D, another configuration of states of a state machine of a user interface for a robotic surgical system is illustrated. The robotic surgical system includes a sensing mechanism to sense and detect alternate types of user input, such as a foot pedal, a button or a switch at the surgeon's console or grip combinations of the master grips at the surgeon's console such as a double click described herein.

In a normal tool mode/state 2540, the robotic surgical tool operates normally within a surgical site. A sensing mechanism/process senses for a predetermined alternate user input 2544A to change the robotic surgical system to operate in an alternate tool mode/state 2545. If the predetermined alternate user input 2544A is not sensed by the sensing mechanism/process, the mode state machine remains in the normal tool mode/state 2540 and continues the sensing process as illustrated by return arrow 2541.

If in the alternate tool mode/state 2545 a predetermined alternate user input 2544B is sensed by the sensing mechanism/process, the mode state machine changes from the alternate tool mode/state 2545 to the normal tool mode/state 2540. If in the alternate tool mode/state 2545 and no predetermined alternate user input is sensed by the sensing mechanism/process, the mode state machine remains in the alternate tool mode/state 2545 and continues the sensing process as illustrated by return arrow 2546.

Referring now to FIG. 25E, a functional block diagram of yet another configuration of states of a state machine 2550 of a user interface for a robotic surgical system is illustrated. The robotic surgical system includes one or more sensing mechanisms coupled to the state machine to sense and detect alternate types of user input, such as a foot pedal, a button or a switch at the surgeon's console or grip combinations of the master grips at the surgeon's console such as a double click described herein.

In a normal tool mode/state 2540, the robotic surgical tool operates normally within a surgical site. A first sensing mechanism/process senses for a first alternate user input 2554A to cause the robotic surgical system to enter an alternate sensing mode/state 2555. If the first alternate user input 2554A is not sensed by the sensing mechanism/process, the mode state machine remains in the normal tool mode/state 2540 and continues the sensing process as illustrated by return arrow 2541. If the robotic surgical system enters the alternate sensing mode/state 2555, a second sensing mechanism/process senses for a second alternate user input 2558A to cause the robotic surgical system to enter an alternate tool mode/state 2545. The first sensing mechanism/process continues to sense for the first alternate user input 2554B again to cause the robotic surgical system to exit the alternate sensing mode/state 2555 and go back to the normal tool mode 2540.

If in the alternate tool mode/state 2545 and a second alternate user input 2558B is sensed by the second sensing mechanism/process, the mode state machine changes from the alternate tool mode/state 2545 back to the alternate sensing mode/state 2555. If in the alternate tool mode/state 2545 no predetermined alternate user input is sensed by the second sensing mechanism/process, the mode state machine remains in the alternate tool mode/state 2545 and continues the second sensing process as illustrated by return arrow 2546.

If the robotic surgical system returns to the alternate sensing mode/state 2555, the first sensing mechanism/process senses for the first alternate user input 2554B to go back to the normal tool mode 2540 and the second sensing mechanism/process senses for the second alternate user input 2558A to return to the alternate tool mode/state 2545.

In the alternate tool mode/state 2545, a number of alternate operational modes in the robotic surgical system may be activated. In one implementation, a gripping force applied by end effectors of the robotic surgical tool is decreased so that delicate tissue may be manipulated appropriately by the end effectors. In another implementation, a wrist torque applied at the wrist of the robotic surgical tool is decreased so that a softer wrist is provided to appropriately manipulate delicate tissue. In still another implementation, the alternate tool mode/state 2545, locks the wrist but without applying any additional force to the end effectors. In another implementation of the alternate user mode, the grips or end effectors are locked together while maintaining the wrist motion in the robotic surgical tool. In yet another implementation, when in the alternate tool mode/state 2545 an alternate view from another camera or a different view angle of a camera may be selected. In another implementation, the alternate tool mode/state 2545 may bring up an overlay onto the stereo video screens at the surgeon's console so that a surgeon is provided additional on-screen information. In still another implementation, the alternate tool mode/state 2545 may lock other axes of rotation such as to lock the outer pitch 215A, yaw 215B, and insertion 257 along pivotal axes of a robotic surgical arm 158 (see FIG. 2B) with a robotic surgical tool 101A. In another implementation, entry into the alternate tool mode/state 2545 may start a data logger to log certain data received or generated by the robotic surgical tool. Exiting the alternate tool mode/state may end the data logging of the data logger. In still another implementation, entry into the alternate tool mode/state 2545 may start a video capture of frames of video data from one or more cameras to record a video of the surgical site. Exiting the alternate tool mode/state may end the vide capture and the recording of the video. In yet another implementation, the entry into the alternate sensing mode/state 2555 may open a down drop menu from which a user could subsequently select using the second alternate user input to enter the alternate tool mode. This may be used when a robotic surgical instrument has additional capabilities that may not be controlled or selected by the limited number of normally available user inputs. For example, an additional servo motor may be controlled in the alternate tool mode to provide another degree of freedom, a force sensing instrument may be controlled in the alternate tool mode, or a thermal sensing instrument may be controlled in the alternate tool mode.

Double Click User Interface Method

Referring now to FIG. 26A, a method of using the double click user interface is now described.

At block 2601, the jaws (end effectors) of the robotic surgical tool are calibrated.

At block 2603, the lock sensing mode is entered by double clicking the master grips of the touch sensitive handle. The lock sensing mode may also be entered into by a mode selection switch.

At block 2605, the master grips of touch sensitive handle are squeezed to a full hard stop to enter a lock mode for the robotic surgical tool.

At block 2607, the master grips of the touch sensitive handle are squeezed to a full hard stop for a second time to exit the lock mode for robotic surgical tool, thereby re-entering the lock sensing mode.

At block 2609, a determination is made as to whether or not lock sensing mode is to be exited. If so, the method goes to block 2610. If not, the method goes to block 2603 and repeats blocks 2603, 2605, 2607, 2609.

At block 2610, the lock sensing mode is exited by double clicking the master grips of the touch sensitive handle. Alternatively, the lock sensing mode may be exited through the mode selection switch.

Referring now to FIG. 26B, a method of operation of the double click user interface is now described.

At block 2631, the lock mode state machine is initialized.

At block 2633, sensing of the double clicking of the master grips of the touch sensitive handle or sensing for another mode selection signal by another mechanism is performed to enter lock sensing mode. Then, the process goes to block 2635.

At block 2635, a determination is made as to whether the double click or other selection signal has been activated to enter the lock sensing mode. If not, the process returns back to block 2633 to continue sensing for a double clicking of the grips. If the double click or other selection signal has been activated to enter the lock sensing, the process goes to block 2637 and block 2644 which are performed in parallel.

At block 2637, sensing for a full hard stop of the master grips of the touch sensitive handle is performed to enter the lock mode for the robotic surgical tool. Then the process goes to block 2639.

At block 2639, a determination is made as to whether a full hard stop occurred to enter the lock mode for a robotic surgical tool. If not, the process returns to block 2637 to continue sensing for a full or predetermined percentage of a hard stop of the master grips to enter the lock mode. If so, the surgery may be performed with the robotic surgical tool in the lock mode and the process goes to block 2640.

At block 2640, sensing for a full or predetermined percentage of a hard stop of the master grips of the touch sensitive handle is again performed to exit the lock mode for the robotic surgical tool. In this case, the surgeon may have completed the task and desires to exit the lock mode to have full dexterity of the robotic surgical tool. The process then goes to block 2642.

At block 2642, a determination is made as to whether another full or predetermined percentage of a hard stop occurred to exit the lock mode for the robotic surgical tool. If so, the process goes to block 2644. If not, the process goes back to block 2640 and continues to sense for the next full or predetermined percentage of a hard stop in the master grips of the touch sensitive handle.

At block 2644, sensing for another double clicking of the master grips of the touch sensitive handle or other mode selection signal is performed to exit the lock sensing mode. Then, the process goes to block 2646.

At block 2646, a determination is made as to whether the double click or other selection signal has occurred to exit the lock sensing mode. If not, the process returns to block 2644 and sensing continues for a double clicking of the master grips. If so, the process returns to block 2633 and senses for a double click of the grips to enter the lock sensing mode.

With a double click user interface, the robotic surgical tool 400 may be used for dual purposes including vessel sealing with reduced (e.g., three) degrees of freedom and dissection with full (e.g., six) degrees of freedom. The double-click user interface allows a surgeon to more efficient quickly switching between vessel sealing and normal operation without taking his head out of the master control console or using a foot pedal switch with other control functions. The double click user interface and the lock modes may reduce development time by leveraging an existing architecture for a robotic surgical system. The double click user interface and the lock modes may reduce surgical procedure time by saving an instrument change. Furthermore, the click user interface and the lock modes may reduce instrument costs for vessel sealing procedures in a robotic surgical system.

CONCLUSION

One or more elements may be implemented in software to execute on a processor of a computer system. When implemented in software, the elements of the embodiments of the invention are essentially the code segments to perform the necessary tasks. The program or code segments can be stored in a processor readable medium or transmitted by a computer data signal embodied in a carrier wave over a transmission medium or communication link. The "processor readable medium" may include any medium that can store or transfer information including an optical medium, semiconductor medium, and magnetic medium. Processor readable medium examples include an electronic circuit; a semiconductor device, a semiconductor memory device, a read only memory (ROM), a flash memory, an erasable programmable read only memory (EPROM); a floppy diskette, a CD-ROM, an optical disk, a hard disk, a fiber optic medium, a radio frequency (RF) link, etc. The computer data signal may include any signal that can propagate over a transmission medium such as electronic network channels, optical fibers, air, electromagnetic, RF links, etc. The code segments may be downloaded via computer networks such as the Internet, Intranet, etc.

While certain exemplary implementations have been described and shown in the accompanying drawings, it is to be understood that such implementations are merely illustrative of and not restrictive to the specific constructions and arrangements shown and described. For example, implementations were particularly described with reference to master grips of a robotic surgical tools but are applicable to other control input mechanisms in the robotic surgical system used to control a robotic surgical tool.

What is claimed is:

1. A user interface system for a robotic surgical instrument having a number of degrees of freedom of movement, the user interface system comprising:
   a double click sensing process to detect a predetermined number of actions of a control input mechanism within a predetermined period of time;
   a hard stop sensing process to detect a predetermined percentage of a hard stop in the movement of the control input mechanism, the hard stop being a closed position of the control input mechanism; and
   a state machine operationally in communication with the double click sensing process and the hard stop sensing process, the state machine to switchably reduce the number of degrees of freedom of movement in the robotic surgical instrument in response to two closure cycles of the control input mechanism within the predetermined period of time and movement of the control input mechanism exceeding the predetermined percentage of the hard stop.

2. The user interface system of claim 1, wherein the predetermined number of actions is two closure cycles of the control input mechanism.

3. The user interface system of claim 1, wherein the state machine to further increase a gripping force of one or more end effectors of the robotic surgical instrument in response to movement of the control input mechanism exceeding the predetermined percentage of the hard stop.

4. The user interface system of claim 1, wherein
the state machine to further hold a gripping force of one or more end effectors of the robotic surgical instrument in response to movement of the control input mechanism exceeding the predetermined percentage of the hard stop.

5. The user interface system of claim 1, wherein
the control input mechanism is a master grip of a touch sensitive handle in a master control console.

6. The user interface system of claim 1, wherein
the predetermined period of time is a lock mode threshold time.

7. The user interface system of claim 1, further comprising:
a mode selection switch in communication with the state machine, the mode selection switch to signal the state machine to switchably reduce the number of degrees of freedom in the robotic surgical instrument.

8. The user interface system of claim 1, wherein
the elements of the system are controlled by instructions stored on a computer readable medium and performed by a processor.

9. A method for a robotic surgical instrument comprising:
entering a lock sensing mode for a robotic surgical instrument; and
in the lock sensing mode,
　switchably reducing degrees of freedom of movement in the robotic surgical instrument in response to movement of the control input mechanism exceeding a predetermined percentage of a hard stop,
　switchably clamping one or more end effectors of the robotic surgical instrument,
　increasing a gripping force of one or more end effectors of the robotic surgical instrument in response to the reduced degrees of freedom of movement in the robotic surgical instrument, and
wherein one or more of the entering, the switchably reducing, the switchably clamping, and the increasing are controlled by instructions stored on a computer readable medium and performed by a processor.

10. The method of claim 9, wherein
the lock sensing mode is entered by double clicking master grips of a touch sensitive handle.

11. The method of claim 9, wherein
the lock sensing mode is entered by selecting a mode selection switch.

12. A method for a robotic surgical instrument comprising:
entering a lock sensing mode for a robotic surgical instrument; and
in the lock sensing mode,
　switchably reducing degrees of freedom of movement in the robotic surgical instrument, wherein the degrees of freedom of movement in the robotic surgical instrument are switchably reduced in response to exceeding a predetermined percentage of a hard stop position of a control input mechanism, the hard stop position being a closed position of the control input mechanism; and
　switchably clamping one or more end effectors of the robotic surgical instrument;
wherein one or more of the entering, the switchably reducing, and the switchably clamping are controlled by instructions stored on a computer readable medium and performed by a processor.

13. The method of claim 12, wherein
the one or more end effectors of the robotic surgical instrument are switchably clamped in response to exceeding the predetermined percentage of the hard stop position in the control input mechanism.

14. The method of claim 12, wherein
the control input mechanism is a pair of master grips.

15. A method for a robotic surgical instrument comprising:
entering a lock sensing mode for a robotic surgical instrument; and
in the lock sensing mode,
　switchably reducing degrees of freedom of movement in the robotic surgical instrument, and
　switchably clamping one or more end effectors of the robotic surgical instrument, wherein the one or more end effectors of the robotic surgical instrument are clamped in response to exceeding a first predetermined percentage of a hard stop position in a control input mechanism, the hard stop position being a closed position of the control input mechanism;
wherein one or more of the entering, the switchably reducing, and the switchably clamping are controlled by instructions stored on a computer readable medium and performed by a processor.

16. The method of claim 15, wherein
the one or more end effectors of the robotic surgical instrument are released in response to exceeding a second predetermined percentage of a hard stop position in the control input mechanism.

17. The method of claim 16, wherein
the control input mechanism is a pair of master grips.

18. A user interface system for a robotic surgical system, the user interface system comprising:
a normal tool mode, including a first alternate sensing process to detect a first alternate user input of a control input mechanism;
an alternate sensing mode including a second alternate sensing process to detect a second alternate user input of the control input mechanism, the second alternate user input is not detectable in the normal tool mode; and
an alternate tool mode and a state machine operationally in communication with the first alternate sensing process and the second alternate sensing process, the state machine to control a robotic surgical tool in an alternate manner in response to the alternate tool mode,
wherein the first alternate user input toggles the user interface system between the normal tool mode and the alternate sensing mode and the second alternate user input toggles the user interface system between the alternate sensing mode and the alternate tool mode;
wherein the alternate manner in which the state machine is to control the robotic surgical tool is one or more of
　decreasing, a gripping force applied by end effectors of the robotic surgical tool to manipulate delicate tissue;
　decreasing a wrist torque applied at a wrist of the robotic surgical tool to provide a softer wrist to manipulate delicate tissue;
　locking the wrist of the robotic surgical tool without applying additional force on the end effectors;
　locking the end effectors together without locking the wrist of the robotic surgical tool;
　selecting video from an alternate camera in the robotic surgical system to view on a monitor;
　selecting a different view angle from a camera in the robotic surgical system to view a different field of view; and
　overlaying information onto a monitor of the robotic surgical system to provide additional on-screen information.

19. The user interface system of claim 18, wherein the control input mechanism is a master grip of a touch sensitive handle in a master control console.

20. The user interface system of claim 18, wherein the control input mechanism is a mode selection switch.

21. The user interface system of claim 18, wherein one or more elements of the system are controlled by instructions stored on a computer readable medium and performed by a processor.

* * * * *